(12) United States Patent
 Peters

(10) Patent No.: US 10,174,495 B2
(45) Date of Patent: Jan. 8, 2019

(54) OIL LEAK DETECTION CIRCUIT AND BLOCKING MECHANISM FOR USE IN A STORM WATER DRAINAGE SYSTEM

(71) Applicant: FABCO INDUSTRIES INC., Farmingdale, NY (US)

(72) Inventor: Kevin Charles Peters, Manorville, NY (US)

(73) Assignee: Fabco Industries Inc., Farmingdale, NY (US)

( * ) Notice: Subject to any disclaimer, the term of this patent is extended or adjusted under 35 U.S.C. 154(b) by 87 days.

(21) Appl. No.: 15/585,895

(22) Filed: May 3, 2017

(65) Prior Publication Data

US 2017/0321412 A1 Nov. 9, 2017

Related U.S. Application Data

(60) Provisional application No. 62/450,303, filed on Jan. 25, 2017, provisional application No. 62/332,753, filed on May 6, 2016.

(51) Int. Cl.
 *E03F 5/04* (2006.01)
 *C02F 1/00* (2006.01)
 (Continued)

(52) U.S. Cl.
 CPC ........ *E03F 5/0411* (2013.01); *B01D 17/0208* (2013.01); *B01D 17/12* (2013.01);
 (Continued)

(58) Field of Classification Search
 CPC ..... B01D 17/0208; B01D 17/12; C02F 1/001;
 C02F 1/008; C02F 1/40; C02F 2101/32;
 C02F 2103/001; C02F 2201/005; C02F
 2201/006; C02F 2209/42; C02F 2301/04;
 C02F 2301/08; C02F 9/00; E03F 1/00;
 E03F 5/0404; E03F 5/041; E03F 5/0411;
 E03F 5/16; G01N 27/10; G01N 33/1833;
 G05D 7/0635
 See application file for complete search history.

(56) References Cited

U.S. PATENT DOCUMENTS 5,935,449 A * 8/1999 Buehler ............... B01D 17/005
                                                    210/742
6,042,721 A    3/2000 Peters, Jr. et al. ............. 210/85
 (Continued)

*Primary Examiner* — Terry K Cecil
(74) *Attorney, Agent, or Firm* — Bodner & O'Rourke, LLP; Gerald T. Bodner; Christian P. Bodner

(57) ABSTRACT

A device for detecting the presence of hydrocarbon fluid in runoff water includes an outer canister and a cartridge situated within the outer canister. The cartridge includes a pre-filter, at least one containment vessel, a diffuser/separator member situated within the containment vessel, a hydrocarbon fluid accumulator and an electronic circuit. The diffuser/separator member slows the flow of runoff water entering the containment vessel so that oil in the runoff water separates from and rises to the surface of the water where it accumulates in the hydrocarbon fluid accumulator. A sensor situated in the hydrocarbon fluid accumulator detects the accumulated oil and sends a signal to the electronic circuit which, in turn, closes a valve and prevents water from flowing through an egress opening in the outer canister.

22 Claims, 33 Drawing Sheets

(51) Int. Cl.
    *C02F 9/00*         (2006.01)
    *G01N 33/18*      (2006.01)
    *G01N 27/10*      (2006.01)
    *G05D 7/06*         (2006.01)
    *B01D 17/02*      (2006.01)
    *B01D 17/12*      (2006.01)
    *E03F 1/00*         (2006.01)
    *E03F 5/16*         (2006.01)
    *C02F 103/00*     (2006.01)
    *C02F 101/32*     (2006.01)
    *C02F 1/40*         (2006.01)

(52) U.S. Cl.
    CPC ............... *C02F 1/008* (2013.01); *C02F 9/00* (2013.01); *E03F 1/00* (2013.01); *E03F 5/041* (2013.01); *E03F 5/0404* (2013.01); *E03F 5/16* (2013.01); *G01N 27/10* (2013.01); *G01N 33/1833* (2013.01); *G05D 7/0635* (2013.01); *C02F 1/001* (2013.01); *C02F 1/40* (2013.01); *C02F 2101/32* (2013.01); *C02F 2103/001* (2013.01); *C02F 2201/005* (2013.01); *C02F 2201/006* (2013.01); *C02F 2209/42* (2013.01); *C02F 2301/04* (2013.01); *C02F 2301/08* (2013.01)

(56) References Cited

U.S. PATENT DOCUMENTS

| | | | |
|---|---|---|---|
| 6,080,307 A | 6/2000 | Morris et al. | 210/163 |
| 6,485,639 B1 | 11/2002 | Gannon et al. | 210/164 |
| 6,503,390 B1 | 1/2003 | Gannon | 210/164 |
| 6,841,077 B2 | 1/2005 | Gannon et al. | 210/692 |
| 7,160,444 B2 | 1/2007 | Peters, Jr. et al. | 210/163 |
| 7,332,091 B2 | 2/2008 | Peters, Jr. et al. | 210/690 |
| 7,837,869 B2 | 11/2010 | Peters, Jr. et al. | 210/164 |
| 8,012,346 B2 | 9/2011 | Peters, Jr. et al. | 210/170.03 |
| 8,168,064 B2 | 5/2012 | Peters, Jr. et al. | 210/163 |
| 8,438,731 B2 | 5/2013 | Peters, Jr. et al. | 29/890.14 |
| 8,623,203 B2 | 1/2014 | Peters, Jr. et al. | 210/170.03 |
| 8,986,822 B2 | 3/2015 | Gupta et al. | 428/220 |
| 9,017,552 B2 | 4/2015 | Peters, Jr. et al. | 210/282 |
| 9,045,891 B2 | 6/2015 | Peters, Jr. et al. | |
| 9,097,390 B1* | 8/2015 | Ward | F17D 1/08 |
| 9,195,238 B2* | 11/2015 | Roden | G05D 9/00 |
| 2004/0222159 A1 | 11/2004 | Peters, Jr. et al. | 210/688 |
| 2005/0211620 A1* | 9/2005 | Owen | B01D 17/005 210/301 |
| 2014/0008283 A1 | 1/2014 | Mabe et al. | 210/282 |

\* cited by examiner

OIL LEAK DETECTION CIRCUIT AND BLOCKING MECHANISM FOR USE IN A STORM WATER DRAINAGE SYSTEM

CROSS-REFERENCE TO RELATED APPLICATIONS

This application is related to U.S. Provisional Patent Application Ser. Nos. 62/332,753 and 62/450,303, filed on May 6, 2016 and Jan. 25, 2017, respectively, each entitled "Oil Leak Detection Circuit and Blocking Mechanism For Use in A Storm Water Drainage System", the disclosure of each of which is hereby incorporated by reference and on which priority is hereby claimed.

BACKGROUND OF THE INVENTION

Field of the Invention

The present invention generally relates to storm water drainage and waste water filtration systems, and more particularly relates to containment apparatus and systems incorporated into such storm water drainage systems and operable in the presence of oil or other hydrocarbons.

Description of the Prior Art

Storm water drainage systems are commonly used in streets, highways, parking lots and other paved surfaces throughout the United States and in foreign countries, especially in urban developments, to remove water accumulating on the surfaces thereof. Most people would recognize the presence of such drainage systems from the heavy metal grates mounted flush in parking lots or streets. Under the grate is usually found a concrete, fiberglass or metal catch basin, which is connected to a conduit that channels the storm water away from the area, to a relatively large water collection reservoirs, or to a river, stream or other body of water.

Filtration apparatus and devices are often incorporated in such catch basins to remove debris, sediment, chemicals, hydrocarbons and other pollutants from the water runoff before it is released into collection reservoirs or bodies of water. For example, U.S. Pat. No. 7,837,869 (Peters, Jr., et al.), which is assigned of record to Fabco Industries, Inc., discloses a system for filtering storm water which includes a storm sewer insert having a filter bag fabricated from a woven geotextile, mesh material and which is mounted beneath the sewer grate such that storm water passing through the grate will enter the filter bag and be filtered by the mesh material. Another example of such a filtering device is found in U.S. Pat. No. 8,012,346 (Peters, Jr., et al.), which is also assigned to Fabco Industries, Inc. The '346 patent discloses a storm sewer insert for filtering and treating storm water which includes four filtering layers, the first being a geotextile fabric for filtering coarse materials from storm water that collects within the collection basin, a second layer of anti-microbial polymeric material that is used for killing microorganisms in the storm water, a third layer of treatment material that is designed to remove hydrocarbons, chlorinated solvents, PCBs, organic solvents, pesticides and biocides, and organically bound metals from the storm water, and a fourth layer which includes zeolite, which is a porous crystal material that has an ion exchange capacity. All of the above-mentioned systems work well in removing debris and pollutants from storm water, and hydrocarbons in relatively low concentrations.

A problem exists, however, in managing hydrocarbon contamination of storm water in high concentrations, which may flow into storm water drainage systems not designed to contain or filter such contamination. Electric utility transformers, oil storage tanks and other sources of high concentrations of hydrocarbons may be situated in parking lots or on paved surfaces where such storm water drainage systems are found. Usually, such utility transformers and oil storage tanks are located in containment areas that are supposed to be sufficient to contain any leaks or spills. However, if such containment areas are clogged or filled with rain water, oil or other hydrocarbons spilled or leaking due to a failure of the transformer housing or storage tank may flow beyond the containment area and into a nearby storm water drainage system, or may be mixed with rain water that flows into the drainage system. Another possible scenario is where a utility transformer, or oil tank, is on fire, and water is used to douse the flames. High volumes of water, mixed with the escaping oil from the transformer or storage tank, may flow into nearby drainage systems. A further possible occurrence of hydrocarbon contamination is when an oil transportation truck overturns, spilling its contents. Conventional water drainage systems are not designed to handle such high concentrations of hydrocarbons caused by oil spills from failed utility transformers, storage tanks and the like.

Efforts have been made to address this problem, but such known efforts come with disadvantages. For example, C.I. Agent Storm-Water Solutions LLC in Louisville, Ky. uses multiple socks filled with a clotting agent which allows rain water to pass through but solidifies when oil contacts it rendering it an impervious barrier to the flow of water and hydrocarbons (see the ciagent.com/about website). Such a clotting agent is disclosed in U.S. Pat. No. 8,986,822.

Another example is disclosed in U.S. Pat. No. 6,485,639 (Gannon, et al.), which is assigned of record to Solidification Products International, Inc. In the '639 patent, a device using filtration media employing polymeric absorbents is disclosed. The filtration media form a plug when contacted by an excessive amount of hydrocarbons which prevents the discharge of the hydrocarbon containing liquid.

The clotting agents and filtration media work passively but are relatively expensive. Once used, they need to be replaced, as such clotting agents and polymeric absorbents have solidified and may not be reused.

OBJECTS AND SUMMARY OF THE INVENTION

It is an object of the present invention to provide an oil leak detection circuit and blocking mechanism for use in a storm water drainage system.

It is another object of the present invention to provide a mechanically and electrically active device for detecting hydrocarbons in storm water and blocking the flow of water containing such hydrocarbons through a storm water drainage system.

It is still another object of the present invention to provide an oil leak detection circuit and blocking mechanism incorporated in a catch basin of a storm water drainage system, which can communicate wirelessly with other leak detection circuits and blocking mechanisms situated in nearby catch basins to prevent drainage of water through those catch basins when an oil leak is detected.

It is a further object of the present invention to provide a hydrocarbon detection circuit and blocking mechanism for use in a storm water drainage system which may be easily reset after triggering and reused multiple times.

It is yet a further object of the present invention to provide an oil leak detection circuit and blocking mechanism for use in a storm water drainage system which is relatively inexpensive to manufacture and easy to install in a catch basin of a drainage system.

It is still another object of the present invention to provide an oil leak detection circuit and blocking mechanism for use in a storm water drainage system which will prevent the flow of oil laden water through the drainage system and into the environment.

It is still a further object of the present invention to provide a hydrocarbon leak detection circuit and blocking mechanism for use in a storm water drainage system which overcomes the inherent disadvantages of known devices and filtration systems.

In accordance with one form of the present invention, a device which electrically detects a high level of hydrocarbons in water, such as caused by a leak from an electric utility transformer or oil storage tank, and mechanically blocks the flow of water through the drainage system is placed below a storm water collection grate within a catch basin of the drainage system. The device includes a cylindrical housing defining an interior cavity in which the mechanism for blocking the flow of water through the device and into the drainage system is located. The housing has a series of water inlet slots formed through the thickness of the side wall thereof A debris filter medium is positioned in alignment with the water inlet slots to catch any debris contained in the water and also to slow the flow of water through the device. A non-woven absorbent material may be placed on the inside bottom surface of the housing to absorb any pollutants or low concentrations of hydrocarbons in the water which are not enough to trigger the blocking mechanism.

The water flows within the device under a weir. The weir is essentially a downwardly extending wall which not only helps provide a laminar flow of water through the device but also defines, with an angled baffle plate next to it, a pocket or chamber which allows oil, which is lighter than water, to separate from the laminar water flow and rise upwardly and accumulate within the pocket. In the upper regions of the pocket, where the separated oil will accumulate, there is located at least one resistance sensor which is connected to an electronic circuit. The sensor will measure a change in resistance when it is contacted by oil, as opposed to water, and this change of resistance is detected by the electronic circuit.

Also within the interior cavity of the housing is a flapper valve which is positioned over a valve seat situated on one open axial end of a water outlet. The flapper valve is connected to an activation chain on which is situated a magnet. A solenoid is positioned within the interior cavity of the housing in alignment with the magnet on the flapper valve chain. The solenoid, also having a magnet, is connected to the electronic circuit of the device.

Water flows through the inlet slots and debris filter and into the internal cavity of the housing, and below the weir. If no or low levels of hydrocarbons are present, the water will continue to flow through the device, past the raised flapper valve and through the water outlet of the device. However, if high levels of oil are carried by the water, the oil will separate and accumulate in the oil detection pocket, and will be sensed by the resistance sensor and electronic circuit of the device. The electronic circuit will trigger the solenoid to magnetically decouple from the magnet mounted on the activation chain, releasing the flapper valve to drop from its raised position to a lowered position where it rests on the valve seat and closes the open end of the water outlet. Thus, when high levels of oil are detected, the device of the present invention will prevent the flow of water, laden with oil, through the outlet and into the water drainage system.

In another form of the present invention, the device is constructed as an assembly which includes a "smart cartridge", which detects the presence of a high concentration of hydrocarbons in runoff water, and an elongated tubular canister in which the smart cartridge is situated. The tubular canister includes a housing with a cylindrical side wall, a bottom wall and an open top side. The canister is placed within a catch basin of a water drainage system, and the canister housing is attachable to a water drainage outflow pipe.

Water, which may be mixed with oil or other hydrocarbon-containing fluid, flows through the open top end of the canister housing, through a pre-filter of the smart cartridge, and out the pre-filter side wall. The water then flows along the interior sides of the canister housing, and is diverted radially inwardly between two spaced apart top and bottom plates, forming part of the smart cartridge. The turbulent flow of water then passes through a central opening formed through the bottom plate whereupon it enters a chamber defined by an inner cylindrical containment vessel forming part of the smart cartridge, in which the flow of the water slows to allow a hydrocarbon-containing fluid (e.g., oil or gas) to separate therefrom. As in the previous embodiment, situated within this chamber are one or more pockets in which any separated oil or gas may accumulate and trigger a sensor situated within each pocket. A puck-like diffuser or separator situated within this chamber helps slow the turbulent flow of water so that the hydrocarbon-containing fluid may separate therefrom.

The water exits the chamber through a plurality of openings formed in the cylindrical side wall of the inner containment vessel of the smart cartridge near the bottom thereof, and passes upwardly between the side wall of the inner containment vessel and the cylindrical side wall of an outer containment vessel encircling the inner containment vessel. The water flows upwardly between the inner and outer containment vessel walls and passes through a plurality of openings formed in the side wall of the outer containment vessel, near the top thereof, whereupon it flows downwardly between the outer containment vessel wall and the canister housing side wall.

Situated at the bottom of the cartridge, between the canister housing side wall and the side wall of the outer containment vessel of the smart cartridge, is a ring-shaped post filter member, formed from an open-cell material, to catch any fine debris carried by the water that is not caught by the pre-filter.

The water then exits a plurality of holes formed in a first bottom plate of the assembly, and is diverted to flow towards the water outlet by a second, lower bottom plate of the assembly.

A gate valve, situated between the second, lower bottom plate and the canister bottom wall, has a movable plate which, when the valve is actuated automatically when hydrocarbons are detected, or manually, slides diametrically across the bore of the water outlet to cut off water flow into the drainage system to which the canister and smart cartridge are connected. Electronic circuitry within the smart cartridge activates the gate valve when hydrocarbons are detected by the sensors in the accumulator pockets and closes the valve automatically.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

Figure 1:
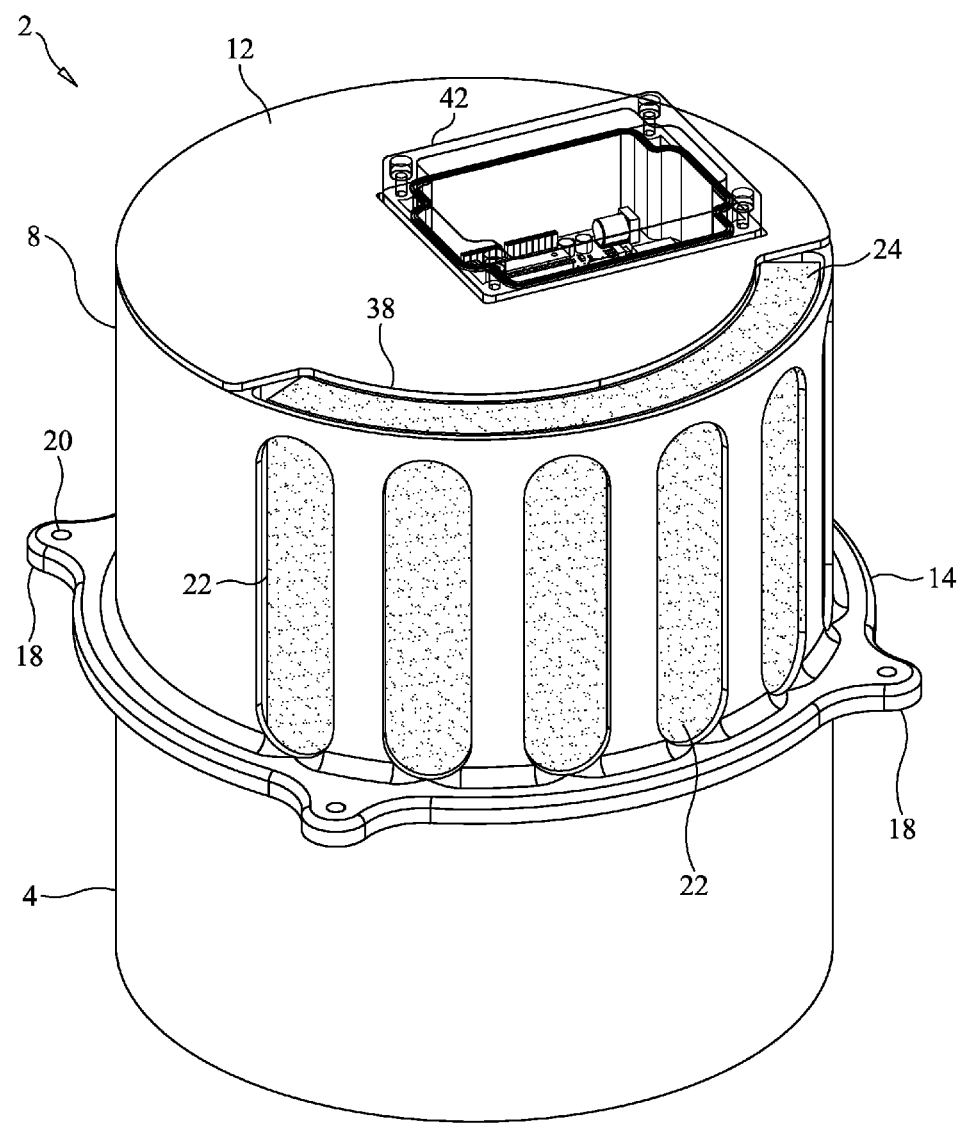
FIG. 1 is a perspective view of a device (i.e., a "smart cartridge") formed in accordance with the present invention for use with a storm water drainage system which detects high levels of hydrocarbons in water and which mechanically blocks the flow of water through the drainage system when such is detected.
Figure 2:
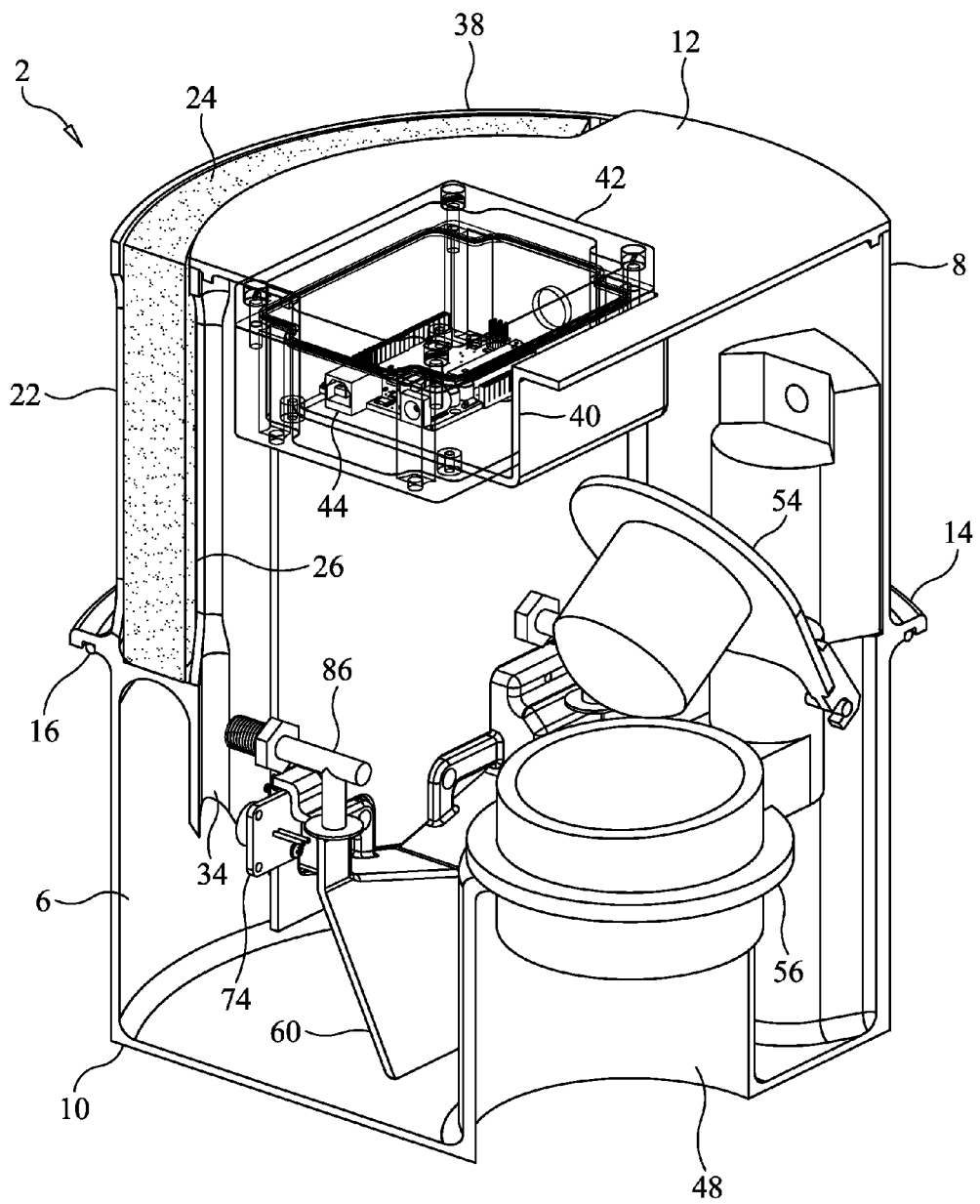
FIG. 2 is a perspective view of the device of the present invention with the housing broken away to illustrate the internal components thereof.
Figure 3:
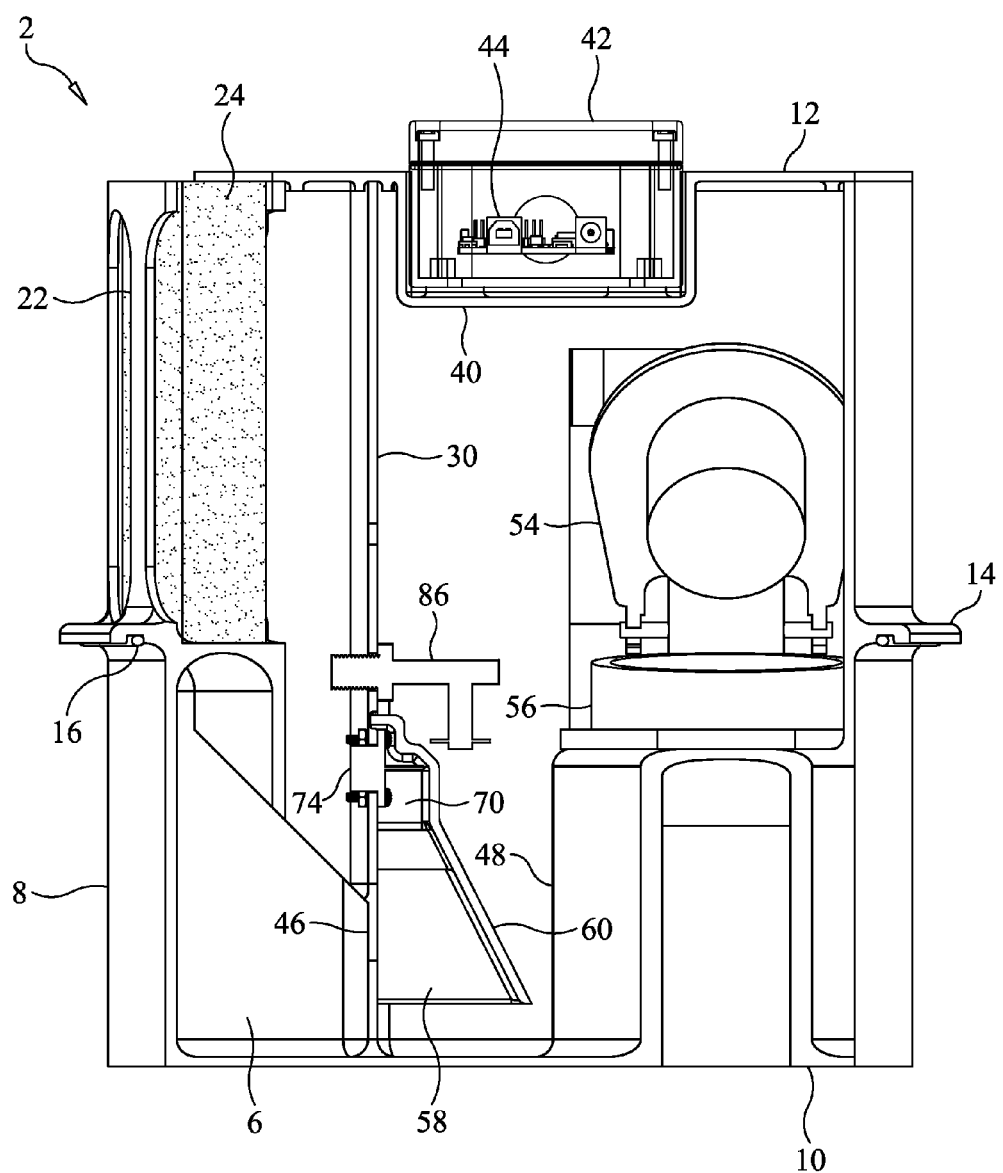
FIG. 3 is a perspective view of the device of the present invention with the housing broken away to illustrate the internal components thereof and taken from a different angle from that of FIG. 2.
Figure 4:
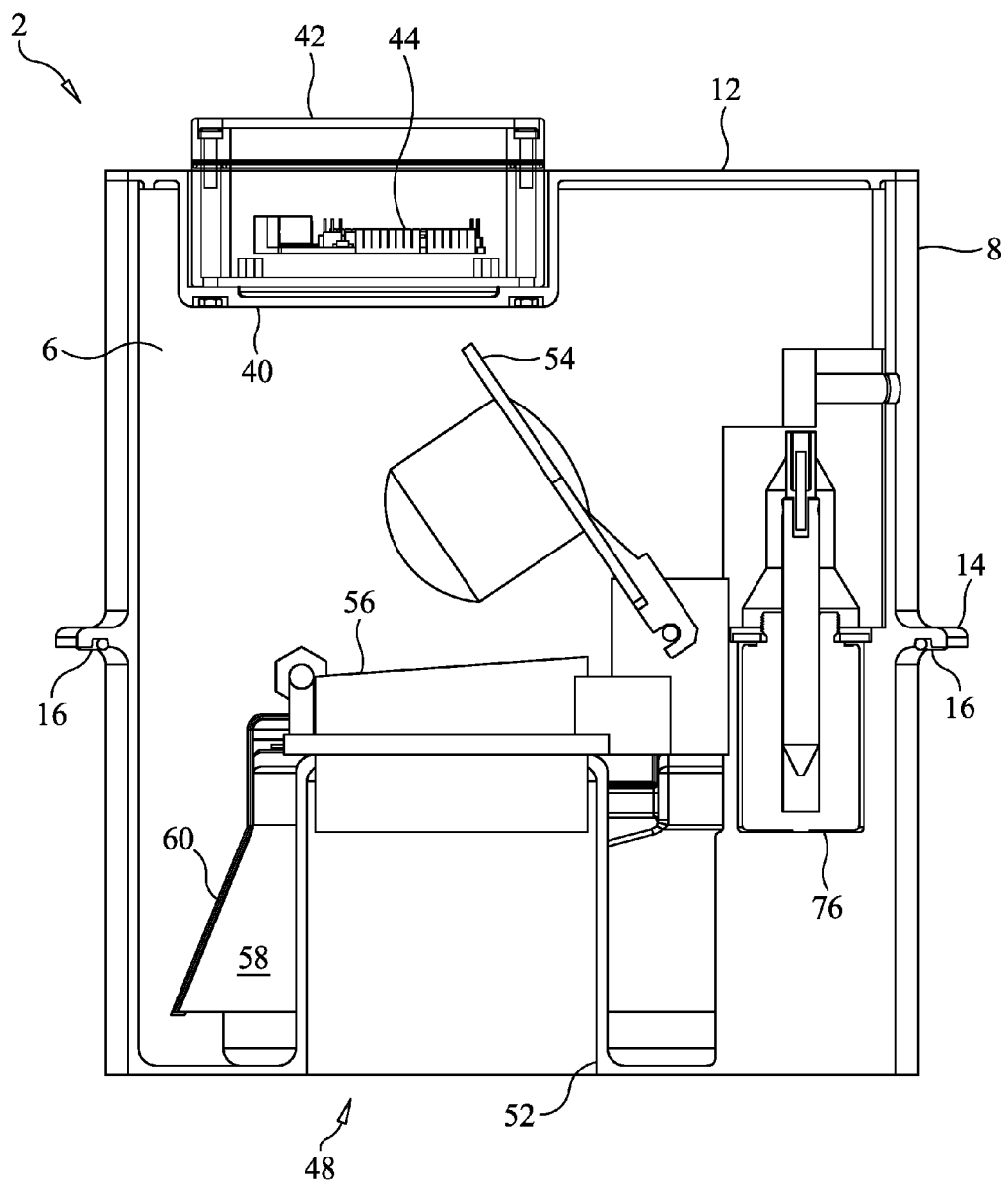
FIG. 4 is a perspective view of the device of the present invention with the housing broken away to illustrate the internal components thereof and taken from a different angle from that of FIGS. 2 and 3.
Figure 5:
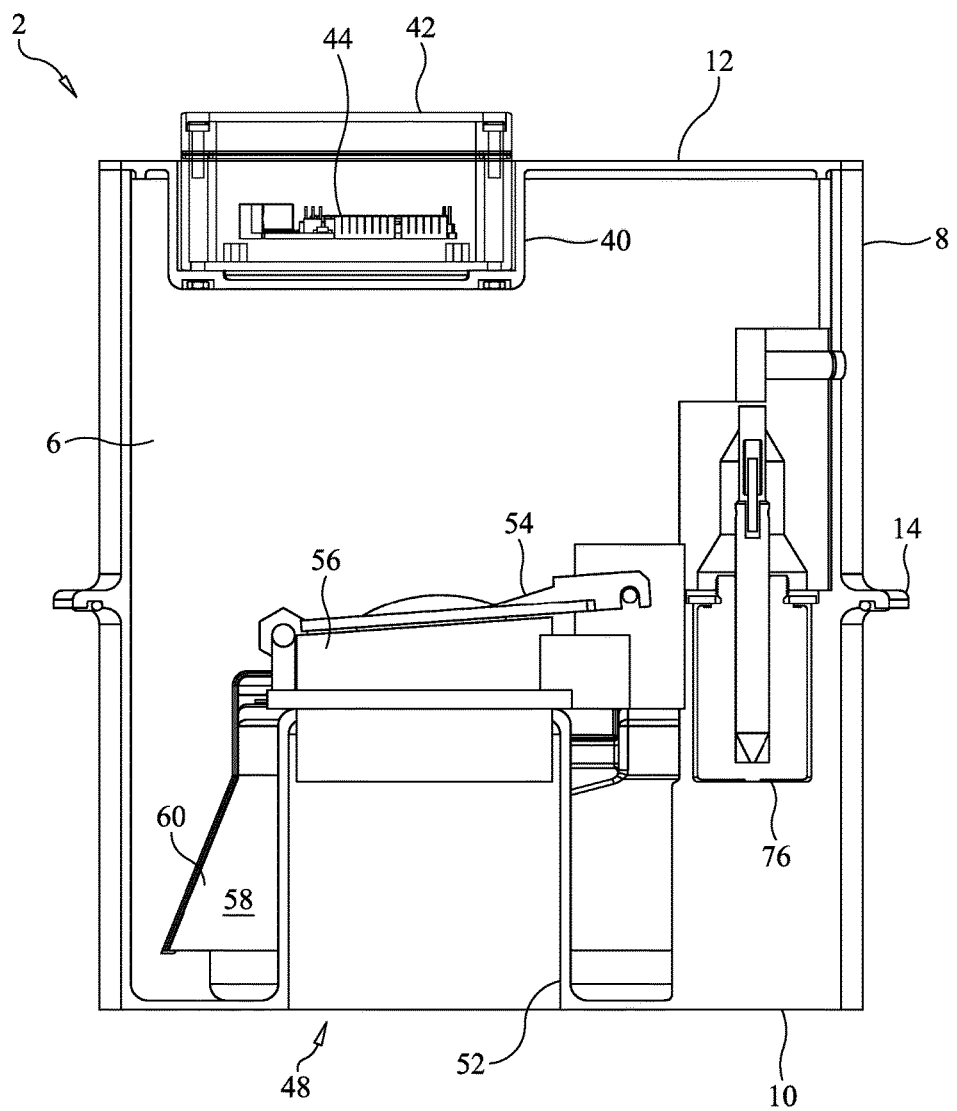
FIG. 5 is a perspective view of the device of the present invention with the housing broken away to illustrate the internal components thereof and taken from a different angle from that of FIGS. 2 and 3, and illustrating the flapper valve of the device in a closed position.
Figure 6:
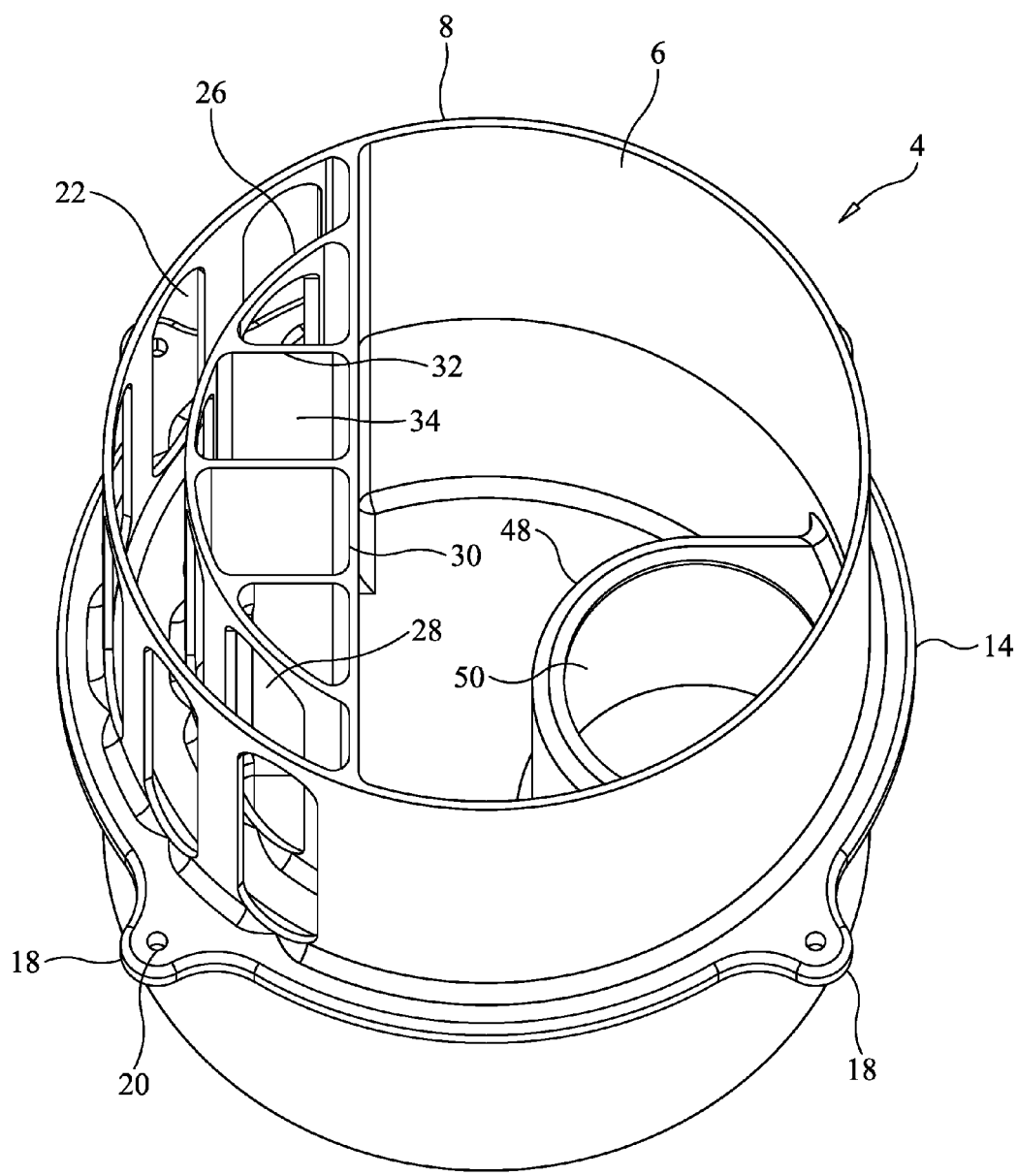
FIG. 6 is a top perspective view of a portion of the housing of the device of the present invention with the other components of the device omitted for clarity.
Figure 7:
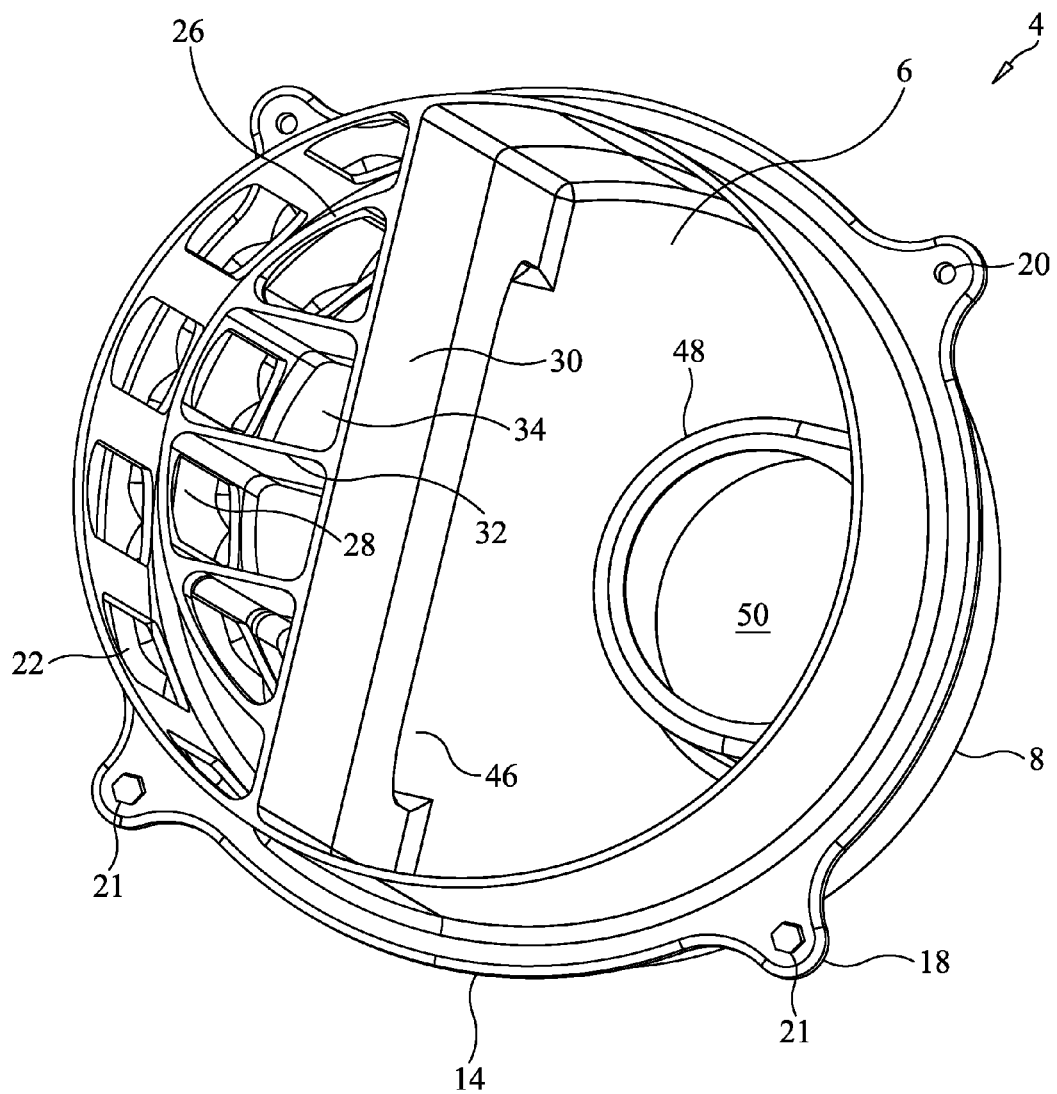
FIG. 7 is a top perspective view of a portion of the housing of the device of the present invention with the other components of the device omitted for clarity, and viewed at a different angle from that of FIG. 6.

FIGS. 1-14, which should be referred to initially, illustrate the mechanical components of the device 2 constructed in accordance with the present invention which is used in a storm water drainage system and which electrically detects a high level of hydrocarbons, such as oil, in the water and mechanically blocks the flow of water through the drainage system. Preferably, and as can be seen from the drawings, the device 2 includes a cylindrical housing 4 or canister defining an interior cavity 6 in which additional components of the device 2, both electrical and mechanical, are situated. The housing 2 is dimensioned to be substantially the size of other filtration cartridges manufactured by Fabco Industries, Inc. of Farmingdale, N.Y. and may be used in place of such filtration cartridges. Alternatively, the device 2 of the present invention may be used in conjunction with such Fabco filtration cartridges and connected in series with such cartridges so that storm water without a high concentration of hydrocarbons will freely pass through the device 2 of the present invention and may enter a Fabco filtration cartridge connected thereto such that the water may be treated for toxic chemicals, pathogens, bacteria, nutrients, sediments and other debris, as well as lower levels of hydrocarbons.

The housing 4 has a generally cylindrical side wall 8, a bottom wall 10 integrally formed with the side wall 8, and a preferably removable disc-shape plate 12 that functions as the top wall of the housing 4. A mounting flange 14 extends radially outwardly from the side wall 8 of the housing 4 and is positioned generally midway on the axial length of the housing 4. The flange 14 is used for mounting the housing 4 in a catch basin and below a storm water collection grate in a manner similar to the way other Fabco filtration cartridges are mounted.

On the underside of the mounting flange 14 is provided an oil resistant O-ring 16 to help seal the housing 4 against a support flange within the catch basin of the drainage system in which it is mounted. Also, circumferentially spaced apart protruding portions 18 of the mounting flange 14 are provided and have formed through the thickness thereof holes 20 for receiving screws or machine bolts 21 for securing the device 2 to the support bracket within the catch basin and to some degree permit the leveling of the device 2 within the catch basin relative to the support bracket on which it is mounted.

Over at least a section of the circumference of the cylindrical side wall 8 of the housing 4 is formed a plurality of water inlet slots 22. The water inlet slots 22 are spaced apart from each other a predetermined distance and are formed through the thickness of the side wall 8 of the housing 4. Storm water may enter the interior cavity 6 of the housing 4 through these slots 22.

Situated adjacent the water inlet slots 22 is a debris filter 24. The debris filter 24 is a synthetic, open pore mesh material used for filtering coarse materials (debris, stones, branches, leaves and sediment) carried by storm water. The debris filter 24 also reduces any turbulent flow of water entering the device 2.

The housing 4 further includes an inner radial wall 26, having slots 28 formed through the thickness thereof and positioned on the inner side of the debris filter 24, a chordal wall 30 spaced inwardly from the inner radial wall 26 and a plurality of spaced apart separator walls 32 joined to and extending transversely between the inner radial wall 26 and the chordal wall 30. The separator walls 32, inner radial wall 26 and chordal wall 30 define a series of flow through channels 34, in communication with not only the slots 28 formed in the inner radial wall 26 but also the debris filter 24 and the water inlet slots 22 formed in the side wall 8 of the housing 4. Water entering the water inlet slots 22 will pass through the debris filter 24 and the slots 28 formed in the inner radial wall 26, and will be directed to flow downwardly, through the flow channels 34, towards the bottom of the housing 4 within the interior cavity 6 thereof.

The inner chordal wall 30 also defines a weir 31 which, in combination with the water flow channels 34, creates a laminar flow of water along the bottom of the housing 4 within the interior cavity 6 thereof A non-woven oil absorbent padding 36 may be affixed to the interior surface of the bottom wall 10 of the housing 4 over which the water flows to absorb and entrap pollutants and hydrocarbons of low concentrations carried by the storm water. Such absorbent padding 36 may be woven or non-woven and may be formed from the materials set forth in U.S. Pat. No. 8,012,346, mentioned previously, the disclosure of which is incorporated herein by reference.

Returning again to FIGS. 1 and 2 of the drawings, it can be seen that the top cover plate 12, which defines the top wall of the housing 4, is formed with a cutout portion 38 along a section of its circumferential periphery. This cutout portion 38 is situated in alignment with the debris filter 24 to facilitate access to the debris filter 24 so that the filter 24, when clogged with debris or sediment, may be easily removed through the cutout portion 38 of the top cover plate 12 without the need to disassemble the entire device 2 or remove the device 2 from the catch basin in which it is mounted. Furthermore, a rectangular (or some other shape) recessed portion 40 of the top cover plate 12 is formed therein to receive a waterproof enclosure 42 for housing the electronic circuitry 44 of the device 2. This waterproof enclosure 42 preferably extends slightly above the top surface of the cover plate 12, and may be easily accessed and/or removed therefrom for replacement or repair, or to change the batteries of the electronic circuitry 44 within the enclosure 42. Also, as will be described in greater detail, the position of the electronic circuit enclosure 42, on the top cover plate 12 of the housing 4, allows the circuit 44 to communicate wirelessly with other devices 2 mounted in nearby catch basins with less interference or blockage of the transmitted signals by the ground surrounding the catch basins in which the devices 2 are mounted.

Figure 8:
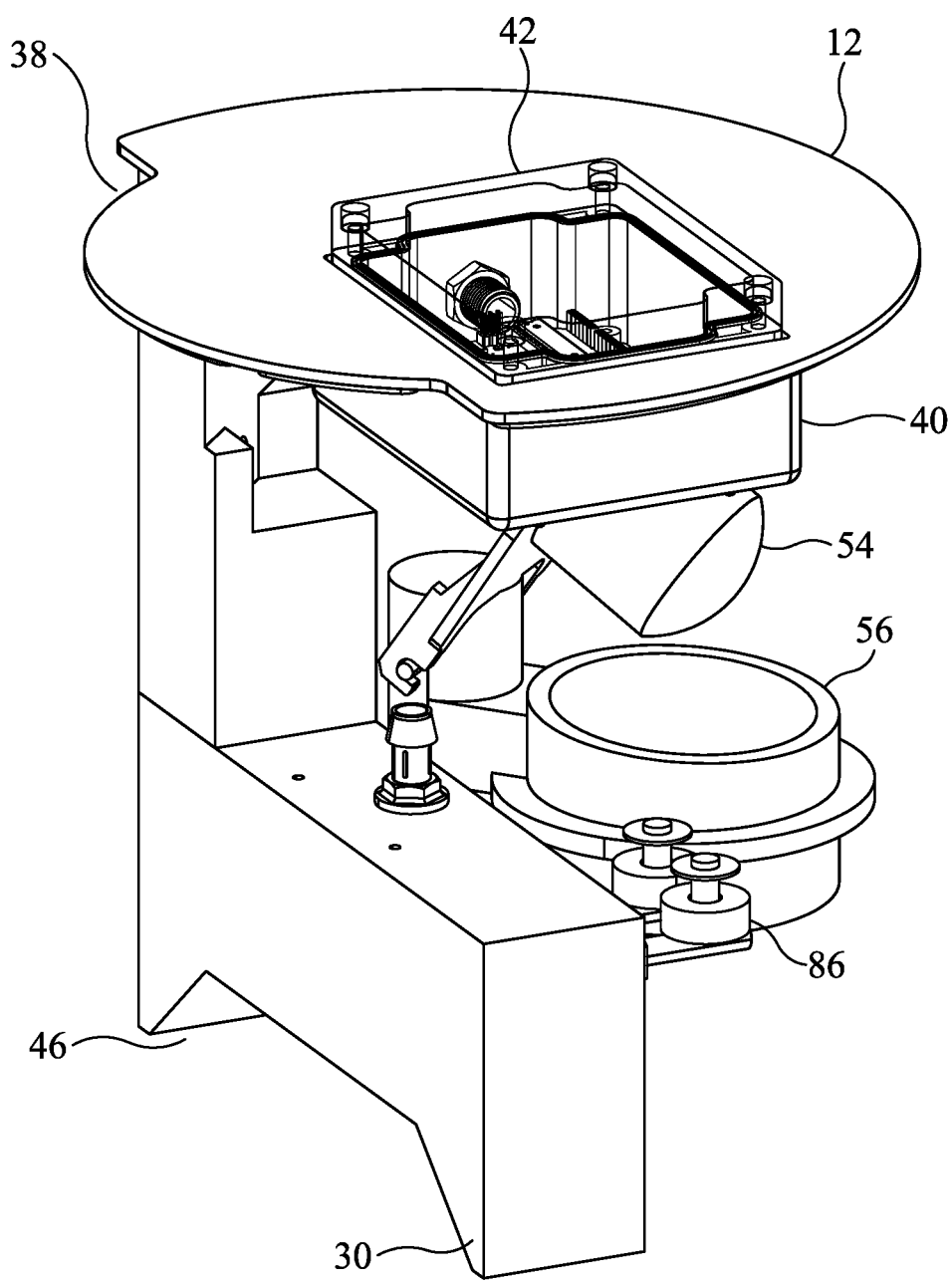
FIG. 8 is a perspective view of the device of the present invention with the housing and debris filter omitted for clarity.

As can be seen from FIG. 8 of the drawings, the inner chordal wall 30, or weir wall, defines with the bottom wall 10 of the housing 4 an opening 46 through which storm water will flow laminarly. The water will flow through this opening 46 and along the bottom wall 10 of the housing 4 within the interior cavity 6 thereof.

A tubular water outlet 48 in the form of a boss extends upwardly from the bottom wall 10 of the housing 4 and into the interior cavity 6 thereof. The tubular water outlet 48, or boss, has an open axial end 50, or orifice, which is in communication with the bore 52 of the water outlet 48. The interior surface of the water outlet 48, within the bore 52, may be threaded to accept the threaded axial end of a conduit (not shown) that is connected to other components of the storm water drainage system such as, for example, a Fabco filtration cartridge as mentioned previously, or to a main water drainage conduit. A valve assembly, which includes a pivotable flapper valve 54 and a valve seat 56, is mounted on the open end 50 or orifice of the water outlet 48. As will be explained in greater detail, the flapper valve 54 may be raised or lowered on the valve seat 56 to open or close the water outlet 48 of the device 2.

Figure 9:
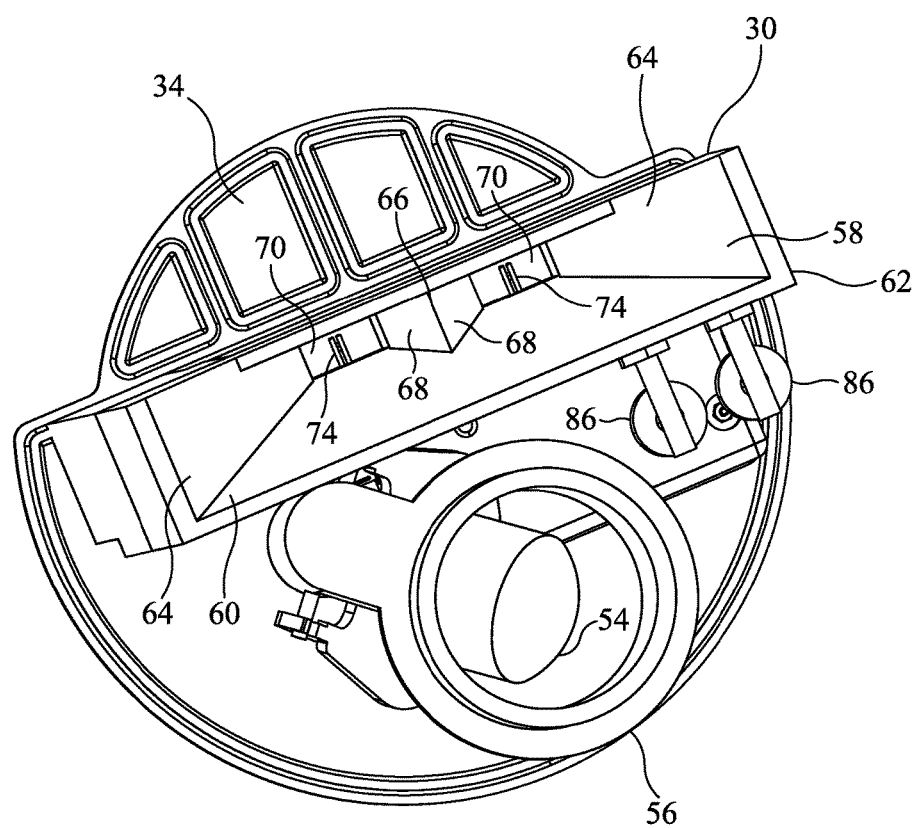
FIG. 9 is a perspective view of the device of the present invention with the housing and debris filter omitted for clarity, and viewed at a different angle from that of FIG. 8.
Figure 10:
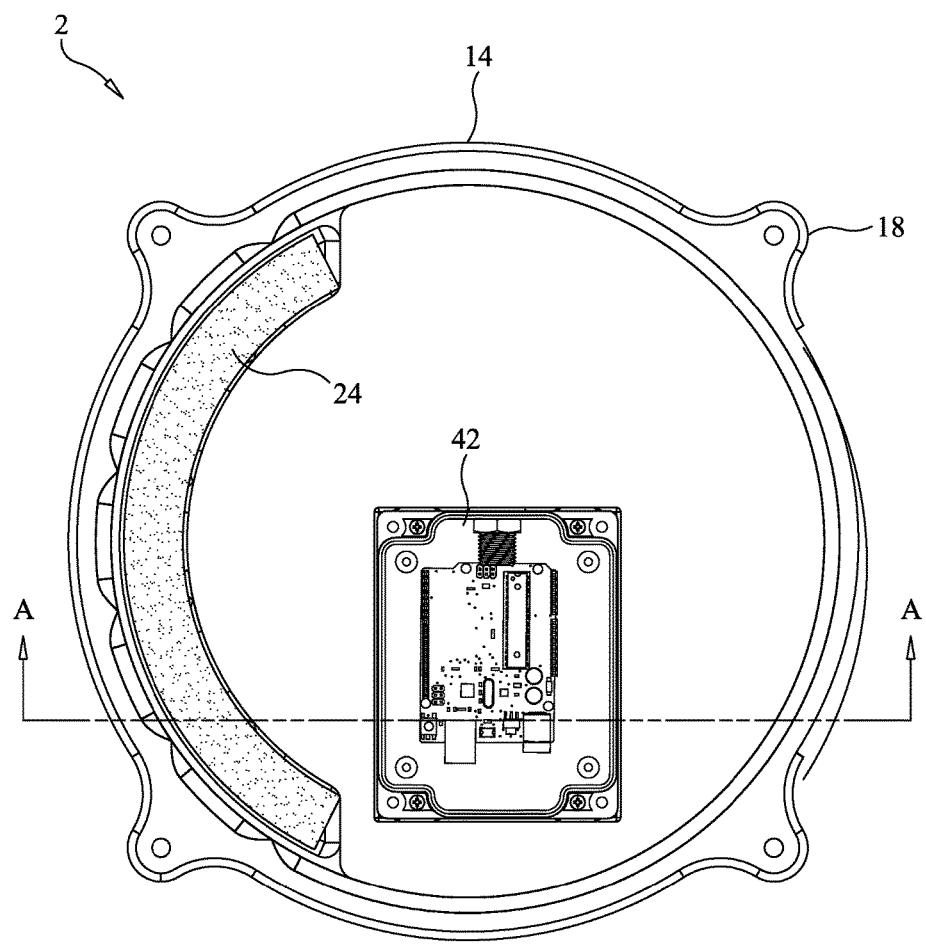
FIG. 10 is a top plan view of the device of the present invention shown in FIG. 1.
Figure 11:
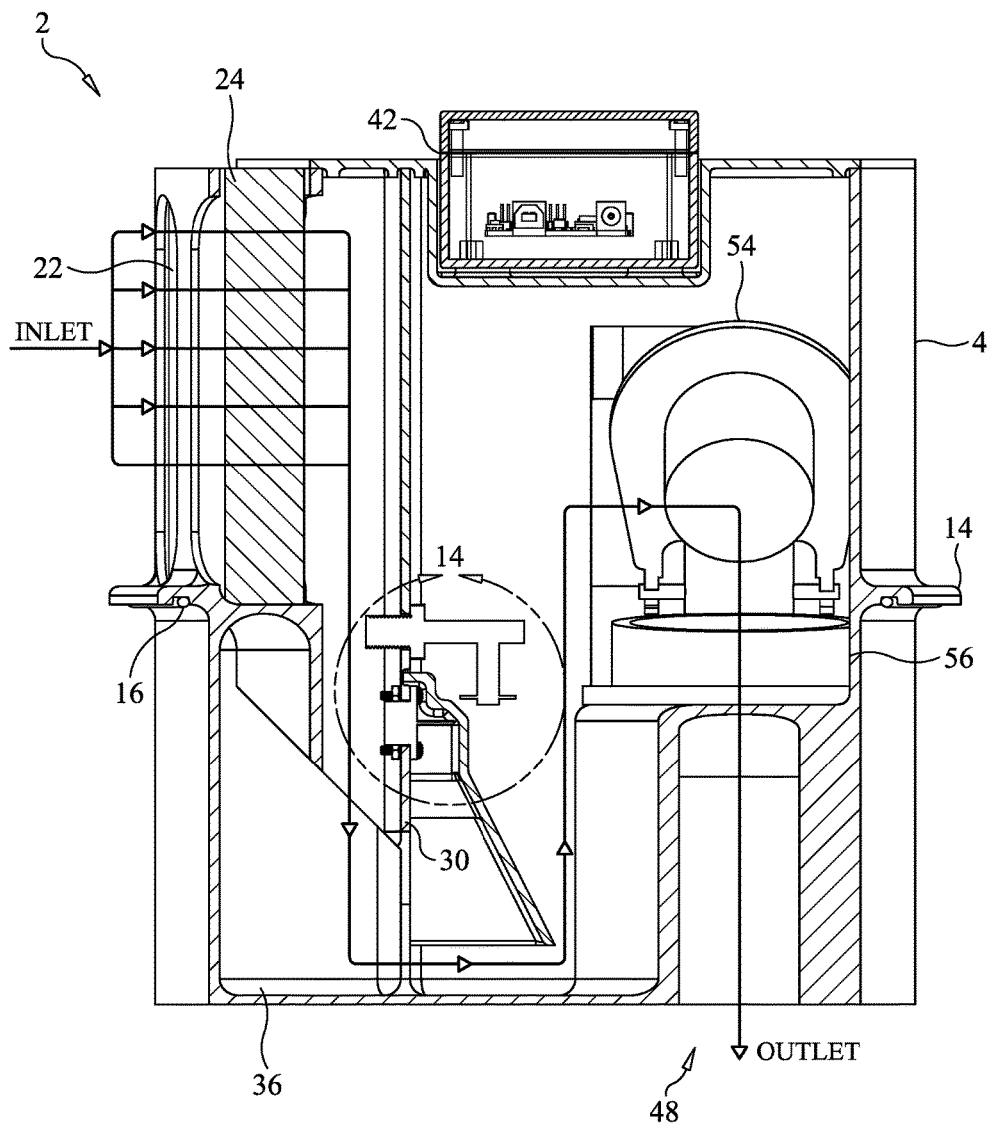
FIG. 11 is a cross-sectional view of the device of the present invention, taken along line A-A of FIG. 10, and illustrating the flow of water through the device.
Figure 12:
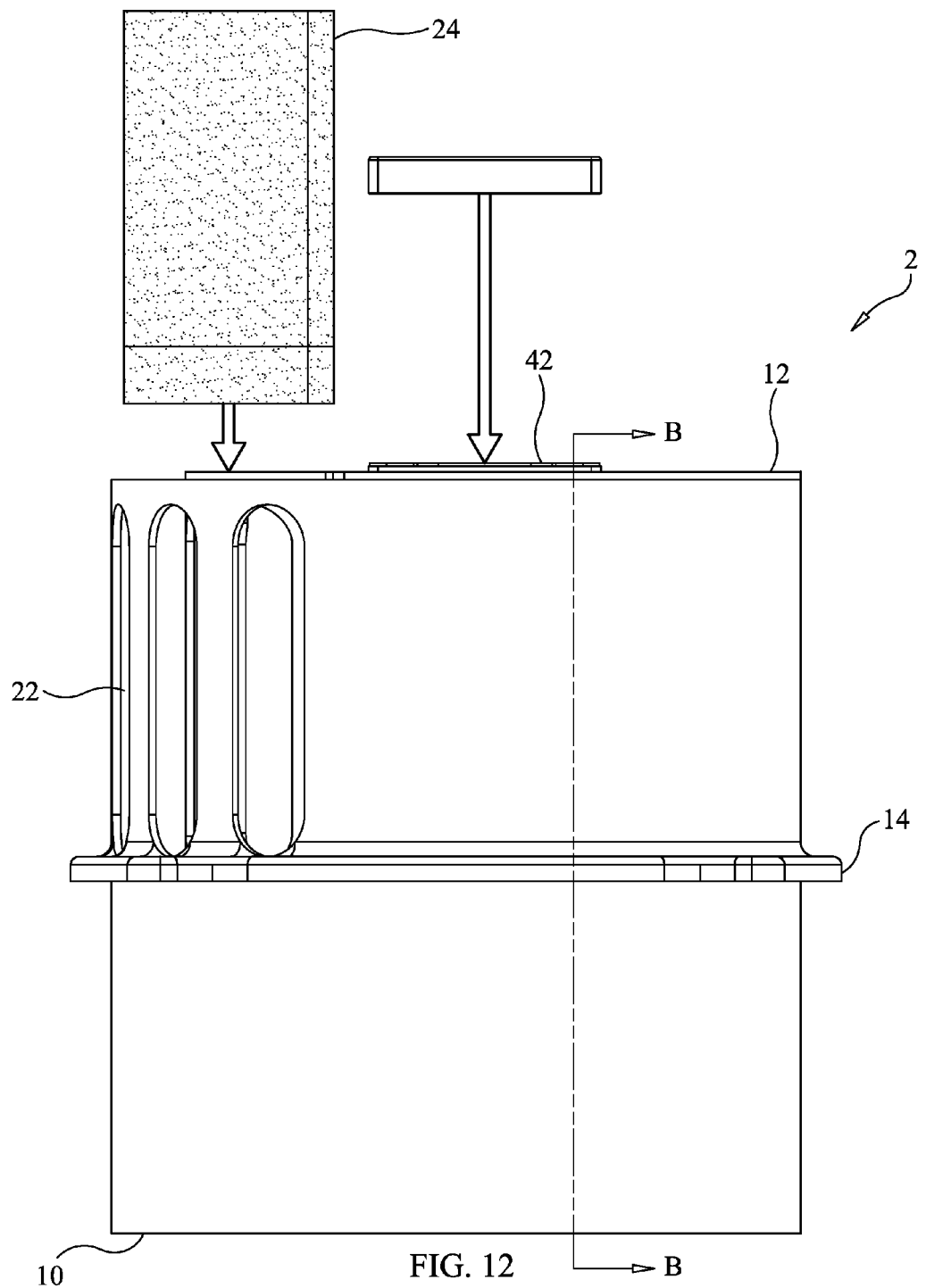
FIG. 12 is a side elevational view of the device of the present invention shown in FIG. 1.

As mentioned previously, the storm water flows through the lower opening 46 formed in the inner chordal wall 30, or weir wall, along the inner surface of the bottom wall 10 of the housing 4. It also flows into and at least partially fills a pocket 58 or chamber defined by the weir wall 30 and a baffle plate 60 which, as shown in FIG. 11 may be angularly disposed, or may be situated within a straight-walled enclosure 62 in the embodiment shown in FIGS. 8 and 9 of the drawings. In a preferred form of the device, and as shown in FIGS. 8 and 9, the pocket 58, or chamber, is preferably defined by the weir wall 30, the angled baffle plate 60, and two opposite sloping lateral side walls 64, the angled baffle plate 60 and the sloping lateral side walls 64 converging in an upward direction to define a region where oil, if present in the water, may accumulate. There is a wedge shaped separator 66 within the pocket 58 or chamber, having walls 68 which mutually diverge in an upward direction, situated midway between the sloping lateral side walls 64 of the chamber 58. Thus, the separator 66 divides the chamber 58, at its upper area, into two oil accumulator regions 70.

Within each oil accumulator region 70 of the chamber 58 is located an air escape port 72 so that air within the chamber 58 may be vented therefrom so as not to prevent oil or water flowing into the upper region 70 of the chamber 58. Also within each of the two oil accumulator regions 70 is located a pair of spaced apart probes 74 arranged side-by-side, each pair of probes 74 acting as a resistance sensor. The spaced apart probes 74 extend into the oil accumulator regions 70 and can measure the impedance or resistance of the liquid contacting the probes 74, be it water or oil. Oil will have a different resistance from that of water and such will be detected by the probes 74 of the resistance sensors.

As described above, it is preferred to have two, side-by-side, oil accumulator regions 70 formed in the chamber or pocket 58. The reason is to ensure that at least one pair of probes 74 in the pocket 58 will detect the presence of oil in the storm water, in the event that oil accumulates in one region 70 more than the other. Also, it is possible that the support bracket within the catch basin of the water drainage system is uneven and causes the housing 4 or canister of the present invention to be slightly tilted when the mounting flange 14 is resting on the support bracket. The bolts passing through the mounting flange 14 on the housing 4 may be adjusted for leveling the device 2 on the support bracket but, nevertheless, it is preferred to have two oil accumulator regions 70 with resistance sensors (probes 74) which independently detect the presence of oil in the storm water flowing through the device 2.

A continuous laminar flow of water will enter the chamber or pocket 58 and at least partially fill it, with excess water spilling under the bottom edge of the baffle plate 60 and flowing upwardly along the outer wall of the water outlet 48 and through the open end 50 or orifice thereof. This nonturbulent flow of water into the chamber or pocket 58 will allow any oil suspended in the water to separate from the water. Since oil is lighter than water (i.e., it has a lower specific gravity), the oil will float to the top surface of the water and will accumulate in one or both of the oil accumulator regions 70 of the chamber or pocket 58, if there exists a relatively substantial volume of oil entrained by the water. The accumulated oil will contact the probes 74 of the resistance sensor and affect the measured resistance between the spaced apart probes 74. As will be described in greater detail and in relation to the electronic circuit 44 shown schematically in FIG. 15 of the drawings, the resistance sensors 74 are coupled to the electronic circuit 44 of the device 2 of the present invention and will sense the change in resistance, and the electronic circuit 44 will respond accordingly.

Figure 13:
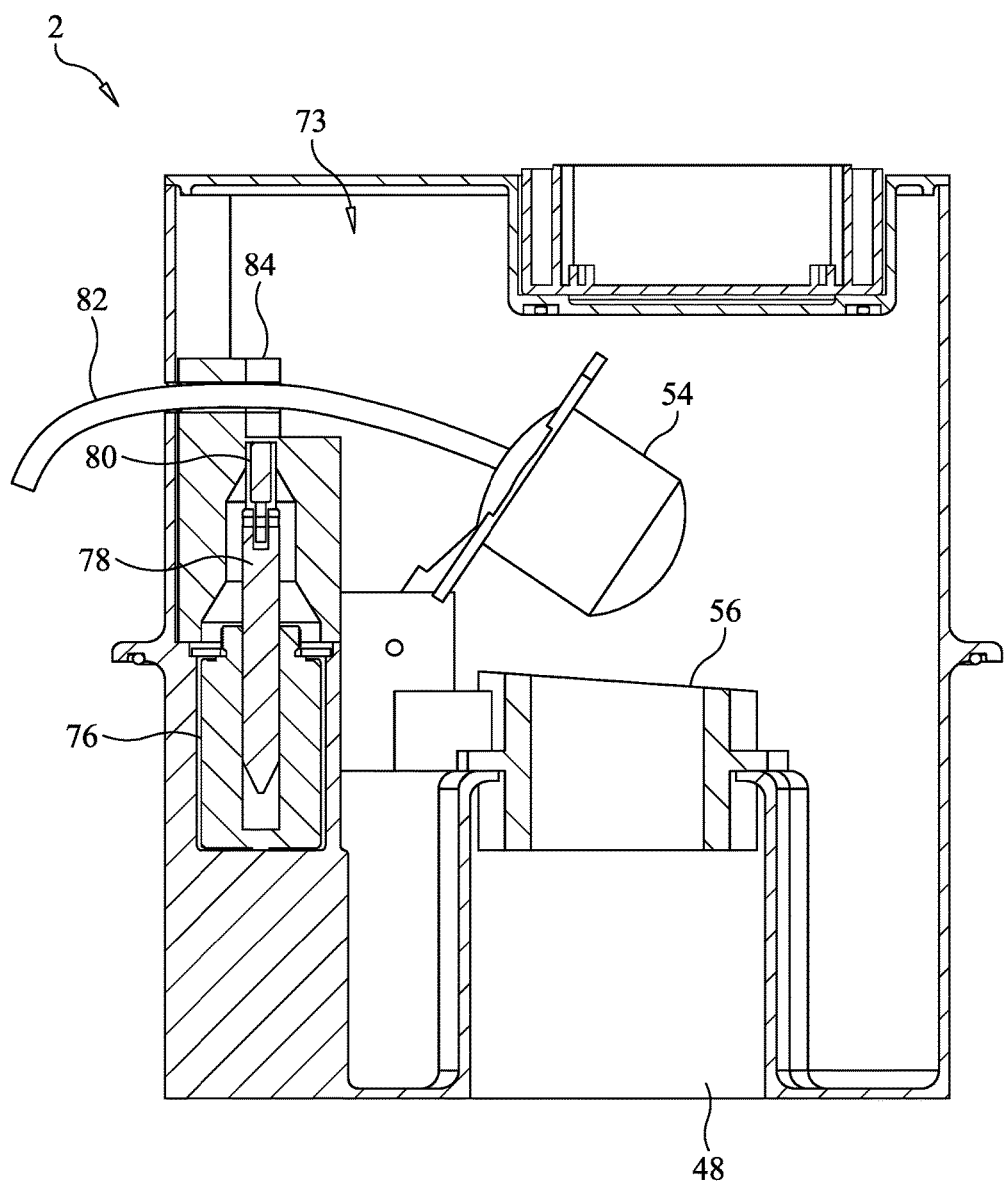
FIG. 13 is a cross-sectional view of the device of the present invention taken along line
B-B of FIG. 12.
Figure 14:
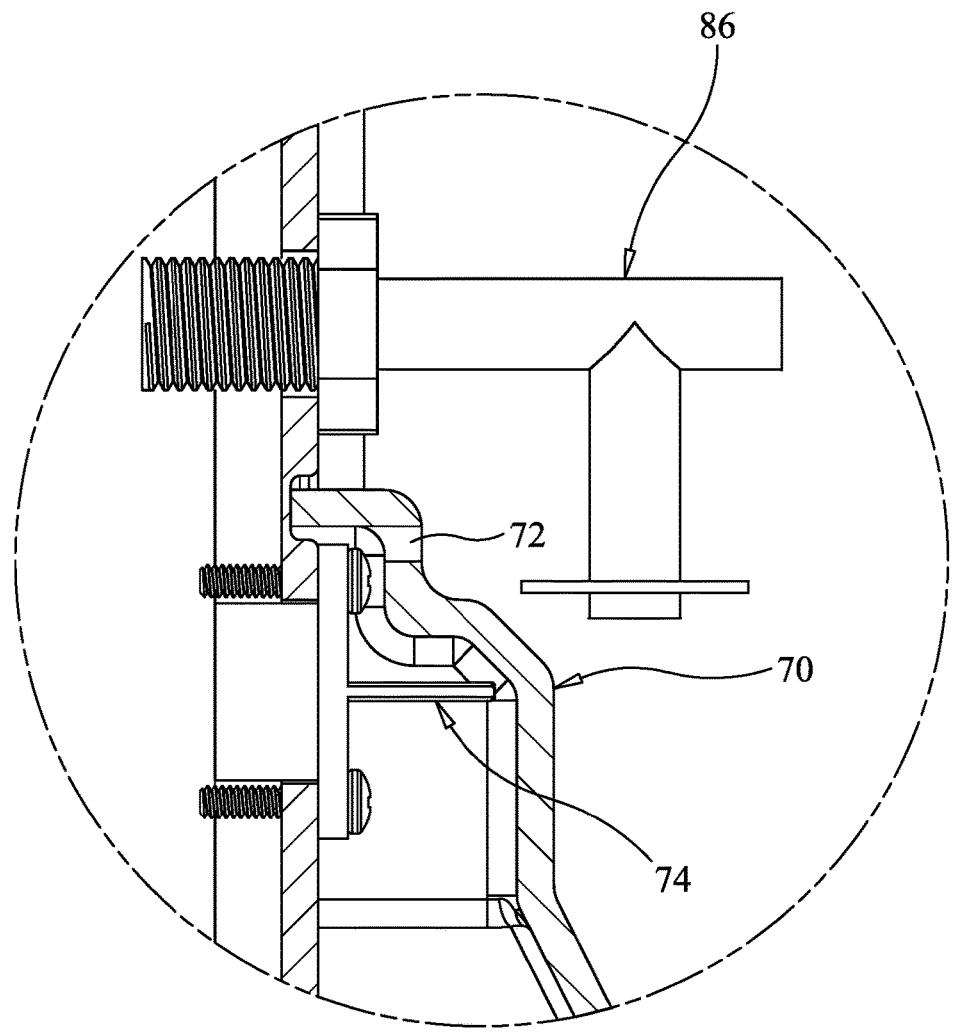
FIG. 14 is a detailed cross-sectional view of a portion of the device of the present invention shown encircled by dashed lines in FIG. 11.

The device 2 of the present invention also includes a valve mechanism 73, including a solenoid 76 whose activation is controlled by the electronic circuit 44. The solenoid 76 has a reciprocatingly moveable plunger 78 having a permanent magnet 80 affixed to the free end thereof. As shown in FIG. 13 of the drawings, the flapper valve 54 includes an activation chain 82 extending from the top surface thereof A permanent magnet 84 is affixed to the activation chain 82 at a predetermined distance from the flapper valve 54. The magnet 84 on the activation chain 82 is magnetically coupled to the magnet 80 on the plunger 78 of the solenoid 76 when the plunger 78 is in an outwardly extended position. This occurs when the solenoid 76 is not energized. The magnetic coupling between the magnet 84 on the activation chain 82 and the magnet 80 on the solenoid plunger 78 is sufficient to maintain the flapper valve 54 in a raised position above the valve seat 56 so that the orifice or open end 50 of the water outlet 48 is open and water entering the device 2 may flow outwardly therethrough. The flapper valve 54 is maintained in this raised position when no excessive oil is detected by the resistance sensors 74 in the oil accumulator regions 70 of the chamber or pocket 58.

However, if oil is detected, then the electronic circuit 44 will energize the solenoid 76 and pull the plunger 78 and magnet 80 affixed to the end thereof away from the magnet 84 mounted on the activation chain 82. The two magnets 80, 84 will decouple and release the flapper valve 54. The flapper valve 54 will fall either by gravity, spring action or water flow pressure from its raised position to its lowered position against the valve seat 56, closing the open end 50 or orifice of the water outlet 48 to prevent water from flowing therethrough.

Preferably, the device 2 of the present invention also includes a pair of redundant but independent float sensors 86 mounted outside the chamber 58 but within the interior cavity 6 of the housing 4. The float sensors 86 will detect the presence of water within the interior cavity 6 of the housing 4. The float sensors 86 are connected to the electronic circuit 44 of the device 2 which, in response to signals from the float sensors 86, will determine, based also on signals from the resistance sensors 74, whether or not to release the flapper valve 54.

More specifically, the reason for having two float sensors 86 and two resistance sensors 74 is for redundancy and to prevent failures. Furthermore, the reason for having both the float sensors 86 and the resistance sensors 74 used together to determine whether the flapper valve 54 should be released is to distinguish between storm water, oil and air.

The electronic circuit 44 of the device 2 monitors both float sensors 86. If either float sensor 86 is in the up position, the electronic circuit 44 checks the resistance in both resistance sensors 74 using voltage divider circuits. If the resistance in either resistance sensor 74 is relatively high, and either float sensor 86 is in an up position, the electronic circuit 44 will energize the solenoid 76 which releases (closes) the valve 54. If the resistance is relatively low in both resistance sensors 74, the electronic circuit 44 will continue to monitor the resistance sensors 74.

Even more specifically, the electronic circuit 44 needs to see the equivalent of two logic HIGH signals from at least one resistance sensor 74 and at least one float sensor 86 before it will close the valve 54. The float sensors 86 distinguish between liquid flow and air. The resistance sensors 74 distinguish between high resistivity (air and oil) and low resistivity (water).

If only air is present in the interior cavity 6 of the device 2, and there is no water flow, the float sensors 86 will be in the down position and provide the equivalent of a LOW logic signal to the electronic circuit 44, the resistance sensors 74 will provide the equivalent of a HIGH logic signal to the electronic circuit 44, and as a result, the electronic circuit 44 will maintain the valve 54 in an open position.

If storm water is flowing through the device 2, one or both of the float sensors 86 will provide the equivalent of a HIGH logic signal to the electronic circuit 44, one or both of the resistance sensors 74 will provide the equivalent of a LOW logic signal to the electronic circuit 44, and as a result, the electronic circuit 44 will maintain the valve 54 in the open position.

However, if oil is present in the water, one or both of the float sensors 86 will be in an up position and provide the equivalent of a HIGH logic signal to the electronic circuit 44, one or both of the resistance sensors 74 will provide the equivalent of a HIGH logic signal to the electronic circuit 44, and as a result, the electronic circuit 44 will energize the solenoid 76 to release the valve 54 and close the water outlet 48.

The housing 4 of the device 2 of the present invention is preferably about twelve inches in diameter, and the bore 52 of the water outlet 48 is about three inches in diameter. This permits approximately one hundred gallons of water to flow per minute through the device 2, which is about ten times greater than prior art devices which remove hydrocarbons from storm water, the storm water typically flowing therethrough at a rate of about ten gallons per minute.

Figure 15:
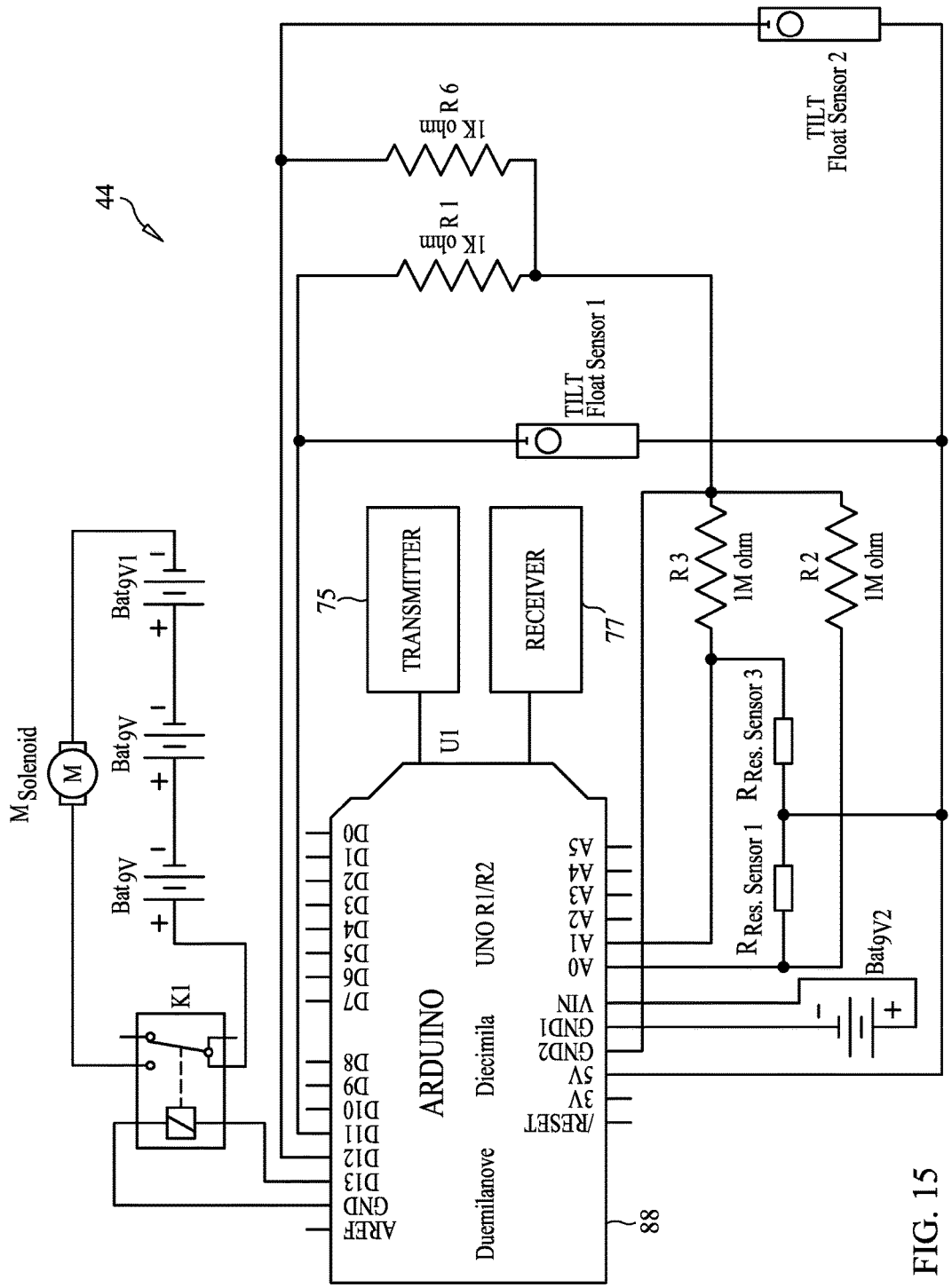
FIG. 15 is a schematic diagram of an electronic circuit used in the device of the present invention.
Figure 16:
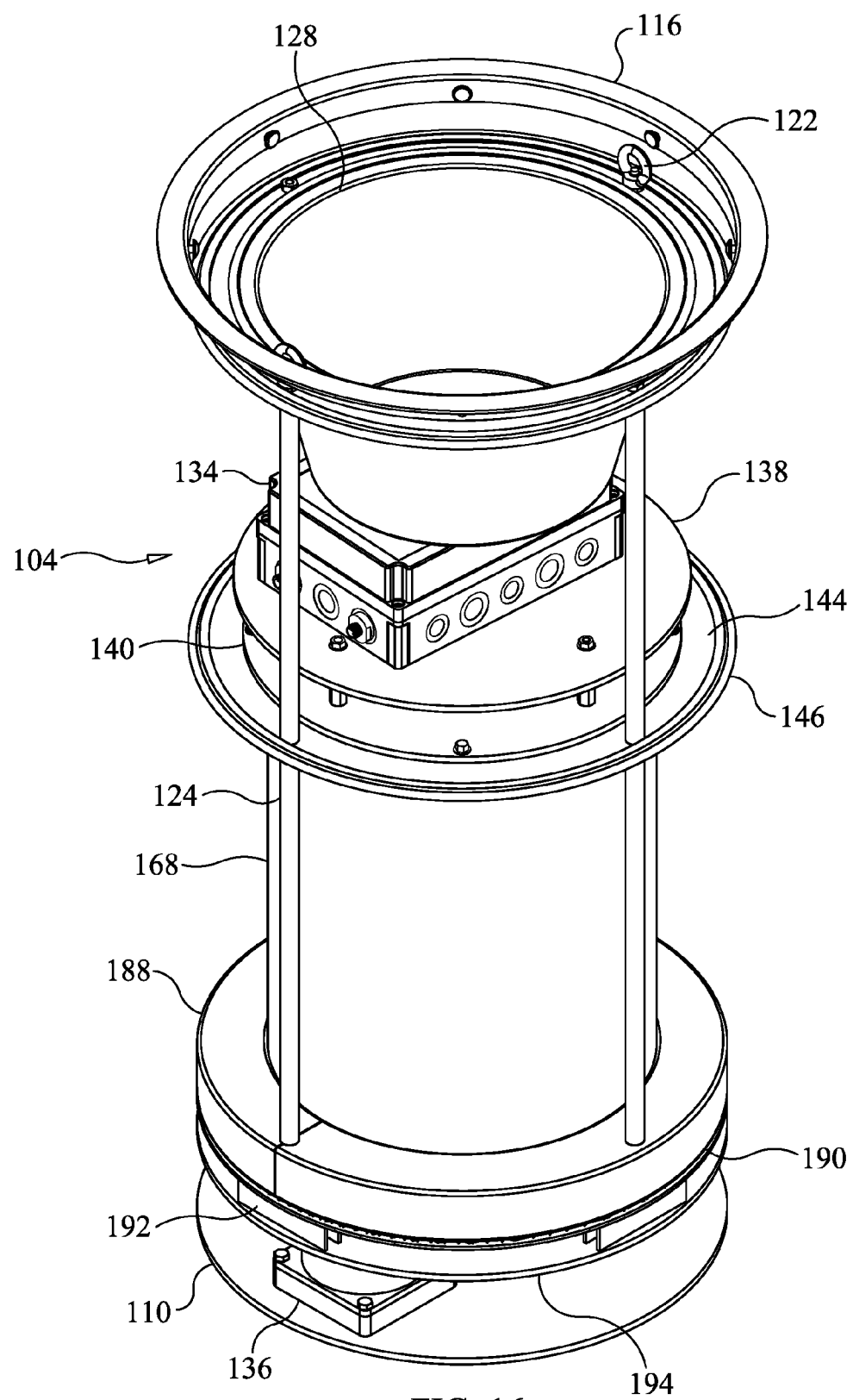
FIG. 16 is a perspective view of a second form of a "smart cartridge" of the present invention.

A preferred form of the electronic circuit 44 used in the device 2 of the present invention is shown in FIG. 15 of the drawings. The circuit 44 is preferably based on an Arduino™ microcontroller-based kit 88, and more preferably, the Arduino Diecimila™, Uno™ or Duemilanove™ kit, or an Atmega™ 328 p-pu chip with an Arduino™ Uno™ Bootloader circuit. Each resistance sensor 74 (labeled Sensor 1 and Sensor 2 in FIG. 15) is connected in series with a one megohm (1 MΩ) resistor R2, R3 to define a voltage divider network on which a voltage is applied, the opposite end of each network being connected to ground. The junctions between the series connected sensors 74 (Sensor 1 and Sensor 2) and resistors R2 and R3 are connected to inputs on the Arduino™ or Atmega™ circuit 88. Thus, any change in the resistance of the sensors 74 (Sensor 1 and Sensor 2) will cause a corresponding voltage change of the voltage divider networks to which they are connected and the signals provided to the Arduino™ or Atmega™ circuit 88. If a high level of oil is detected in the storm water by one or both sensors 74 (Sensor 1 and Sensor 2), the Arduino™ or Atmega™ circuit 88 will energize the solenoid 76 (labeled as K1 in FIG. 15) to release the flapper valve 54 to close the water outlet 48 of the device 2. The two float sensors 86 (labeled Float Sensor 1 and Float Sensor 2 in FIG. 15) are also connected in series with a one kilohm (1 KΩ) resistor R1, R6 to define a voltage divider network on which a voltage is applied, the opposite end of each network being connected to ground. The junctions between the series connected sensors 86 (Float Sensor 1 and Float Sensor 2) and resistors R1 and R6 are connected to inputs on the Arduino™ or Atmega™ circuit 88. Thus, any change in the state of a float sensors 86 will affect the voltage at the junction of the voltage divider network that the sensor 86 forms part of and which is provided to the Arduino™ or Atmega™ circuit 88. The circuit 88, in response to signals from one or both float sensors 86, will determine whether there is a flow of liquid through the interior cavity 6 of the device 2 or just air being present, since the resistance sensors' output signals will be at the equivalent of a logic HIGH (high resistivity) in the presence of air or oil, and at the equivalent of a logic LOW (low resistivity) in the presence of water, as explained earlier. The electronic circuit 44 of the device 2 will either cause the flapper valve 54 to be released by the solenoid 76 to close the water outlet 48, or maintain the flapper valve 54 in a raised, open position, based on the signals received from the float sensors 86 and the resistance sensors 76.

As shown in FIG. 15 of the drawings, the electronic circuit 44 of the device 2 of the present invention may include a Bluetooth™ transmitter 75 and receiver 77 to communicate wirelessly with the electronic circuits 44 of other devices 2 in nearby catch basins. If one device 2 detects an excessive amount of oil in the storm water flowing therethrough, the electronic circuit 44 will not only close the valve 54 in that device 2 but also communicate with other devices 2 in nearby catch basins to cause those devices 2 to close their valves 54 as well. In this way, no contaminated water will drain through the catch basins within a predetermined area of the oil spill.

Reference should now be had to FIGS. 16-34, which illustrate another form of a device 100 for detecting hydrocarbons in runoff water constructed in accordance with the present invention. The device 100 is formed as an assembly which includes an elongated tubular outer canister 102 and the "smart cartridge" 104 received within the axial bore or interior cavity 103 thereof and preferably removable from the outer canister 102.

More specifically, the outer canister 102 is placed within a catch basin of a water drainage system, and has a housing 106 which is attachable to a water drainage outflow pipe. The canister housing 106 includes a cylindrical side wall 108, a bottom wall 110 joined to the side wall 108 and an open top side 112, which defines a runoff water ingress opening 113. The bottom wall 110 includes an opening 114 formed through the thickness thereof, which is attachable to an outflow pipe of the water drainage system.

The smart cartridge 104 of the present invention, which is removably fitted within the bore 103 of the outer canister housing 106, will now be described. Starting from the top and proceeding to the bottom of the smart cartridge 104, the cartridge 104 includes a circular mounting flange 116 which has a lip 118 extending radially outwardly from and perpendicularly to a circular ring segment 120, which ring segment 120 is secured by spaced apart machine bolts to the top edge of the canister housing 106, preferably on the outside of the side wall 108 thereof, such that the lip 118 extends outwardly from the canister housing 106. The mounting flange 116 thus may rest on a circular opening of comparable size forming part of the drainage system, such as within a catch basin thereof This structure allows the entire assembly 100, including the outer canister 102 and the smart cartridge 104 held therein, to be removed from the catch basin of the drainage system. Alternatively, the canister 102 may remain in place within the catch basin, but the smart cartridge 104 may be lifted axially outwardly therefrom through the open top side 112 of the canister housing 106. For this purpose, lifting rings 122 spaced apart diametrically from each other and attached to posts 124 which extend axially through the smart cartridge 104 are provided so that the smart cartridge 104 may be raised, and lowered, from and into the canister housing 106, while leaving the canister housing 106 in place within the catch basin of the water drainage system.

The mounting flange 116 defines an interior opening 126 which is in alignment with the open top side 112 of the canister housing 106 through which runoff water may flow.

Figure 17:
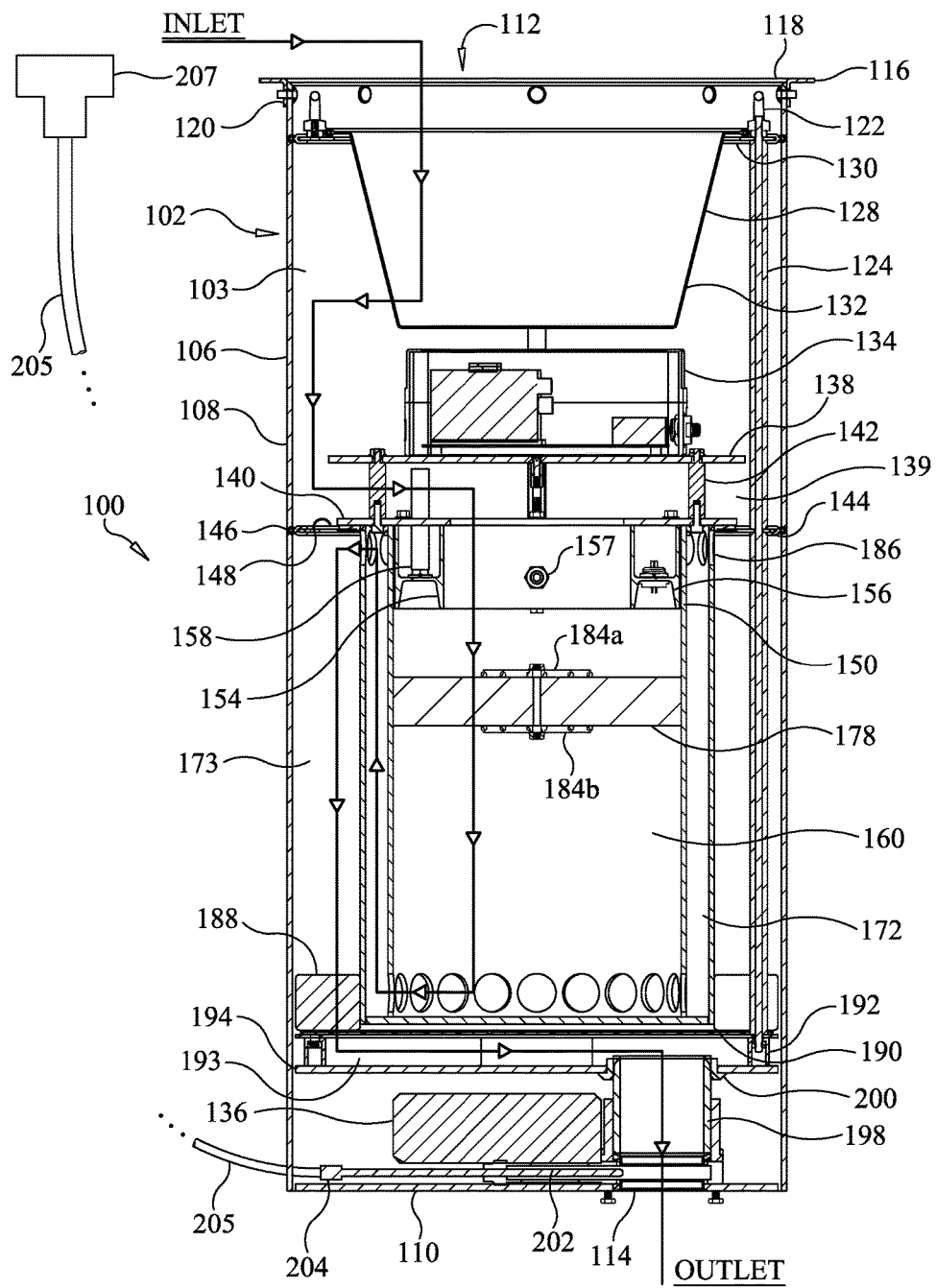
FIG. 17 is a longitudinal cross-sectional view of an assembly comprising the smart cartridge shown in FIG. 16 and a canister in which the smart cartridge is mounted, and illustrating the flow of water therethrough by arrows and lines.
Figure 18:
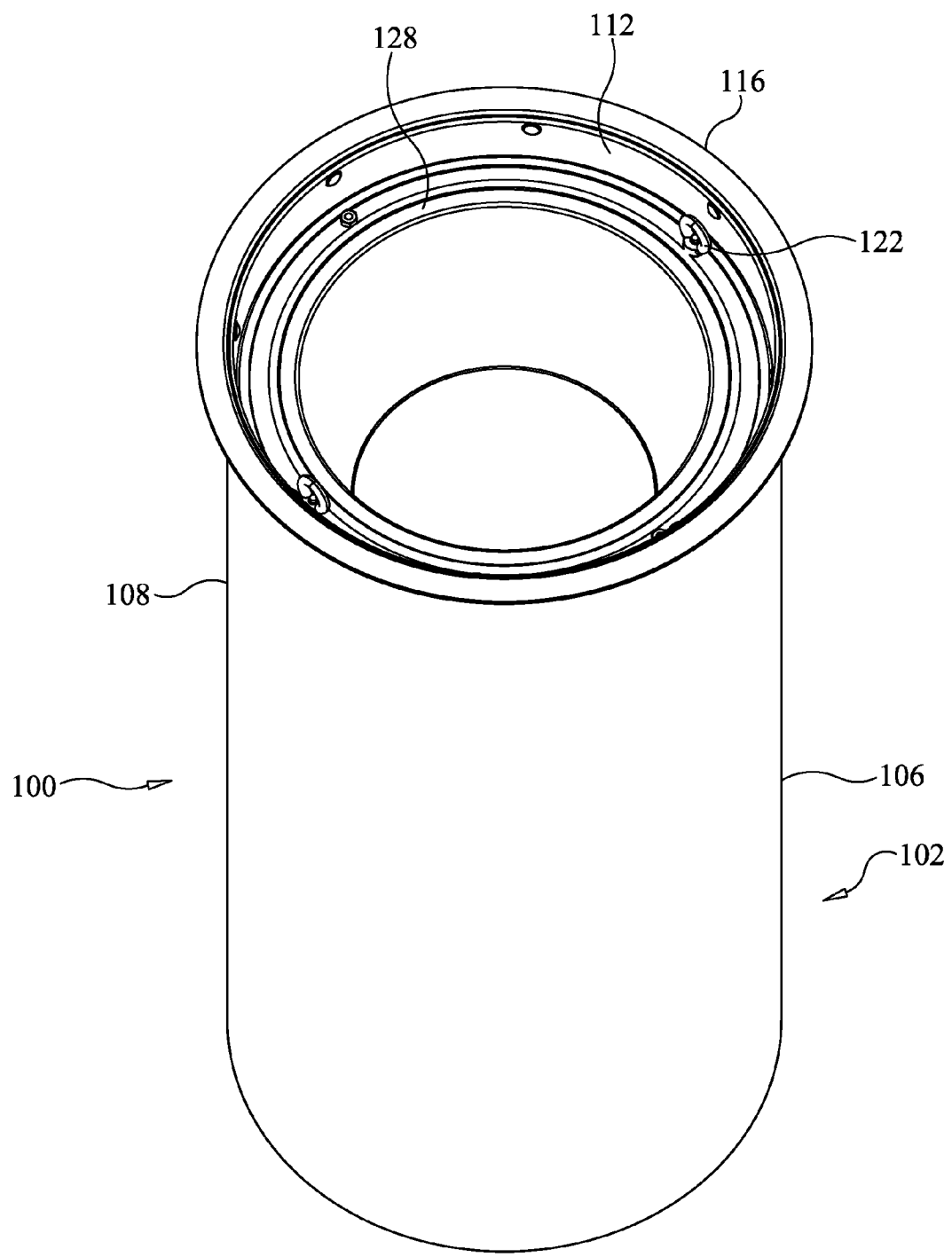
FIG. 18 is a top perspective view of the device of the present invention shown in FIGS. 16 and 17.
Figure 19:
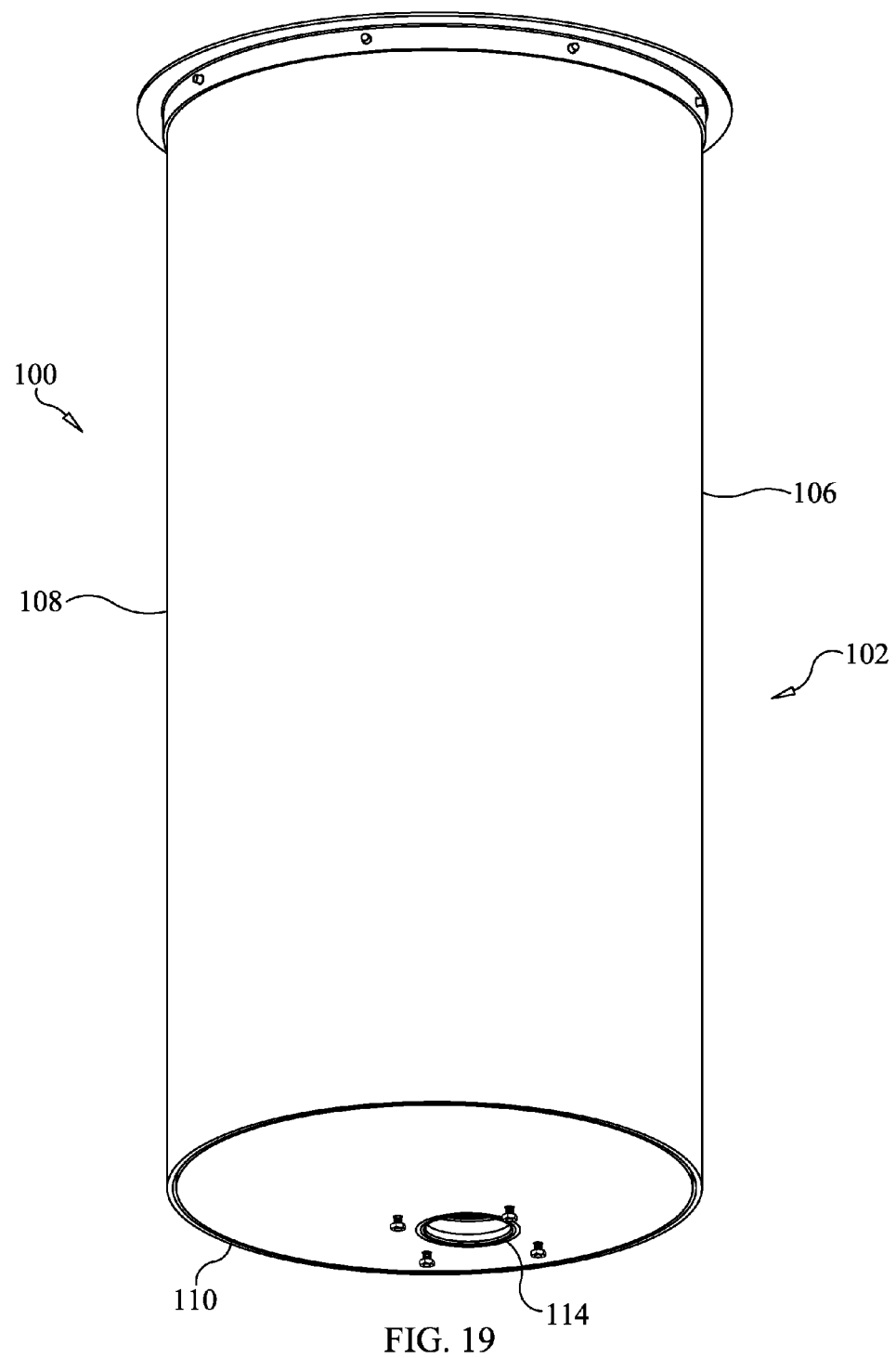
FIG. 19 is a bottom perspective view of the device of the present invention shown in FIG. 18.
Figure 20:
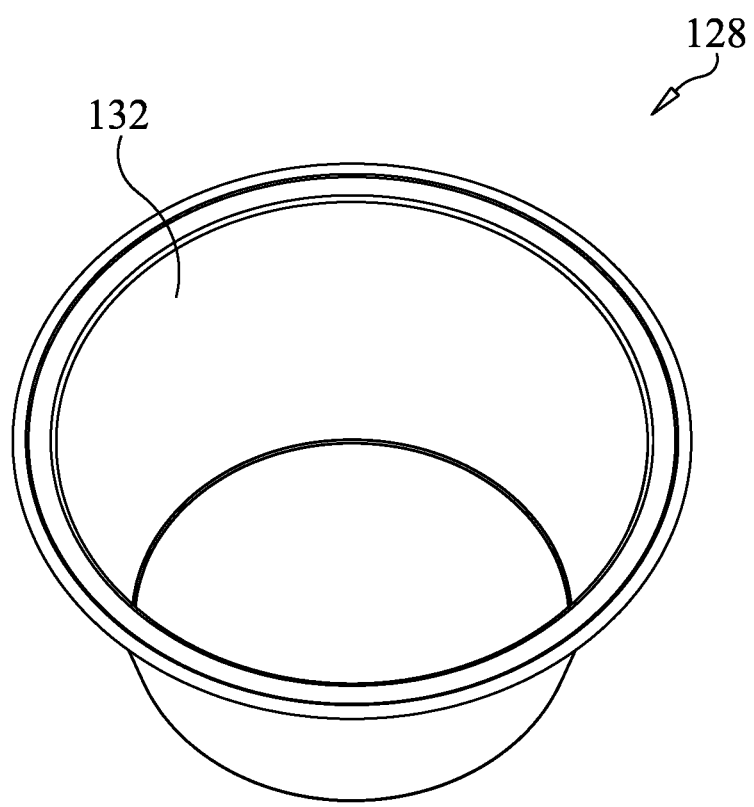
FIG. 20 is a perspective view of a pre-filter used in the device of the present invention shown in FIGS. 16-19.
Figure 21:
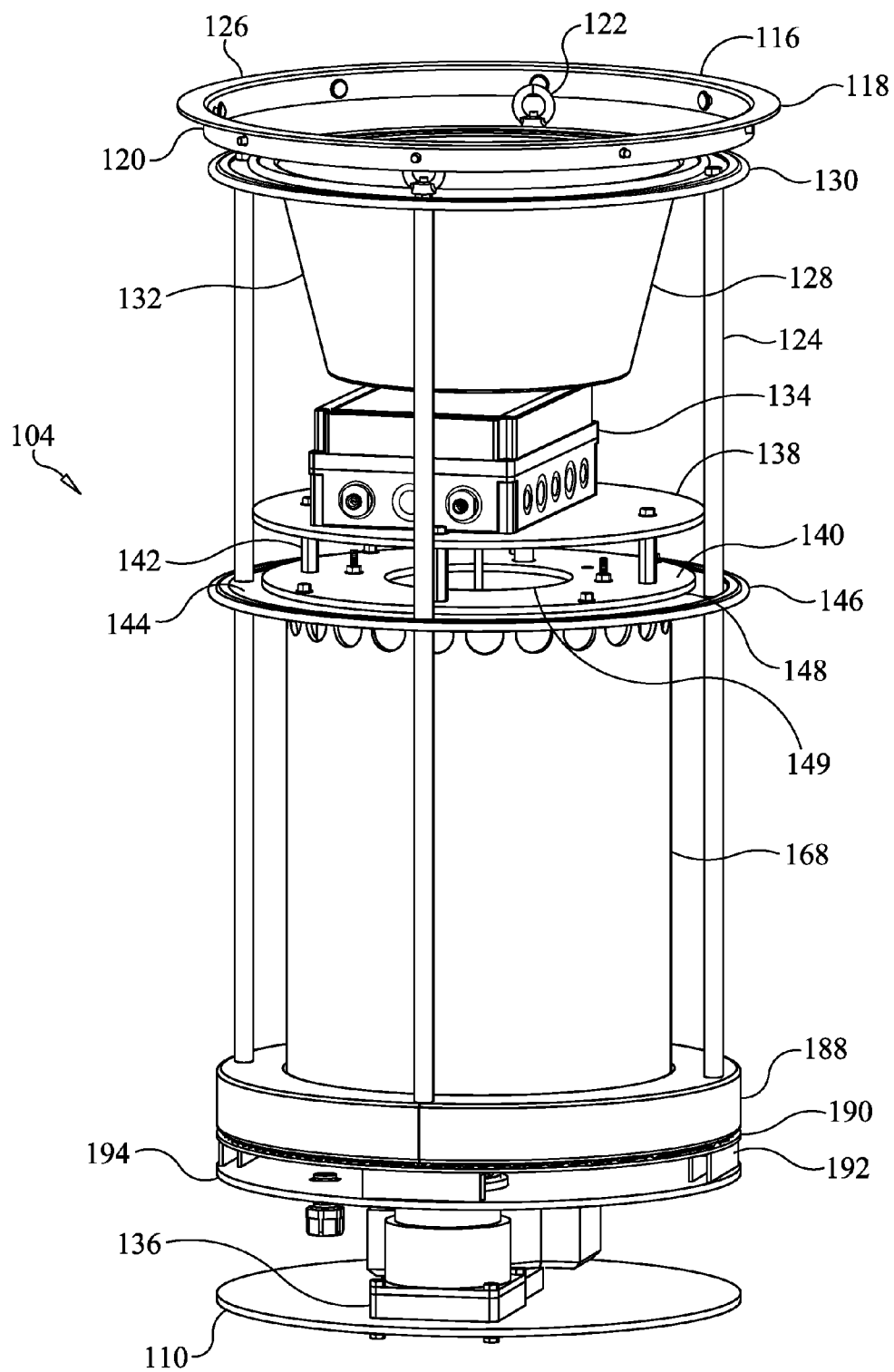
FIG. 21 is a top perspective view of the device of the present invention shown in FIGS. 16-19, with the cylindrical side wall of the outer canister housing omitted therefrom.
Figure 22:
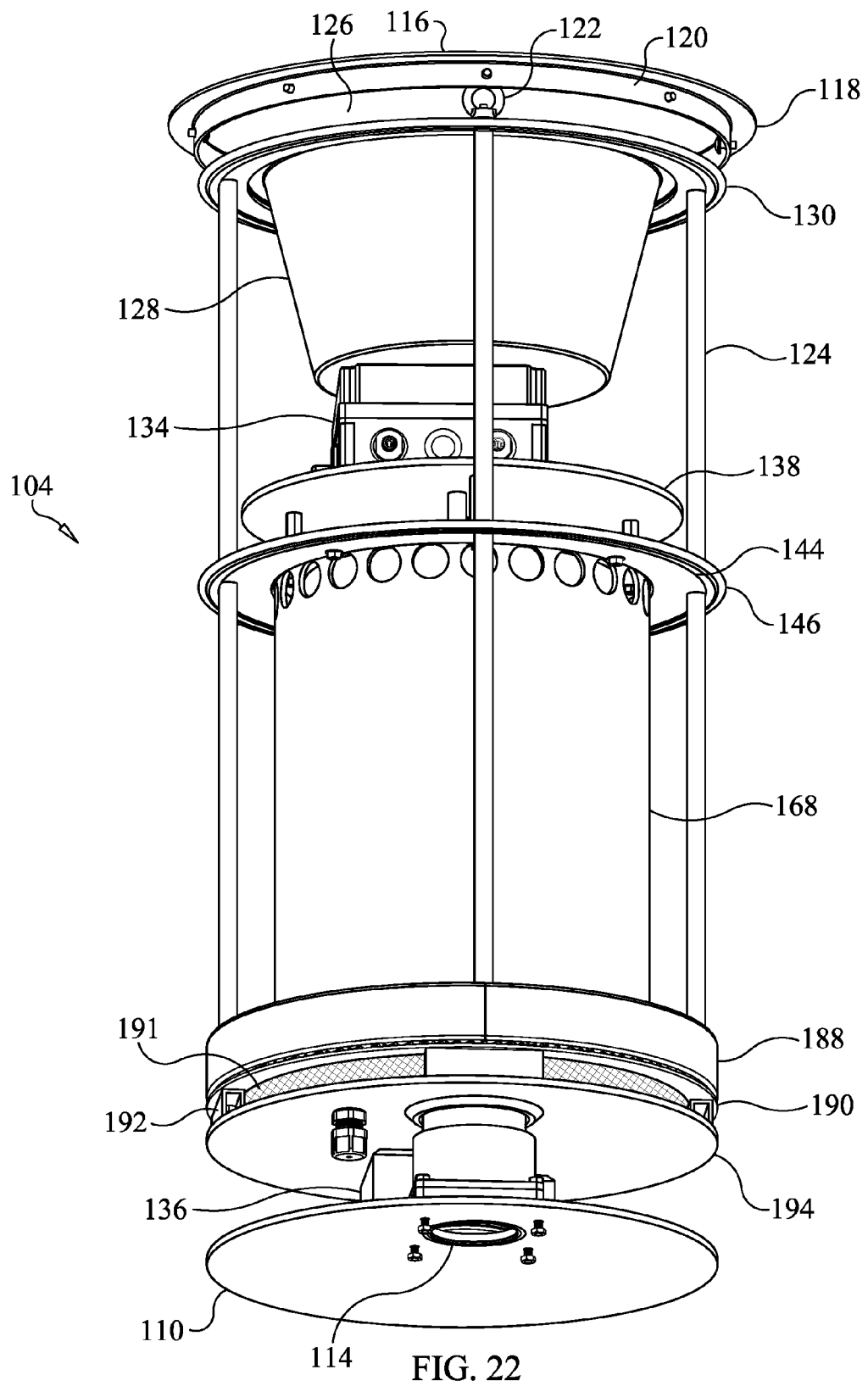
FIG. 22 is a bottom perspective view of the device of the present invention shown in FIGS. 16-21, with the cylindrical side wall of the outer canister housing omitted therefrom.
Figure 23:
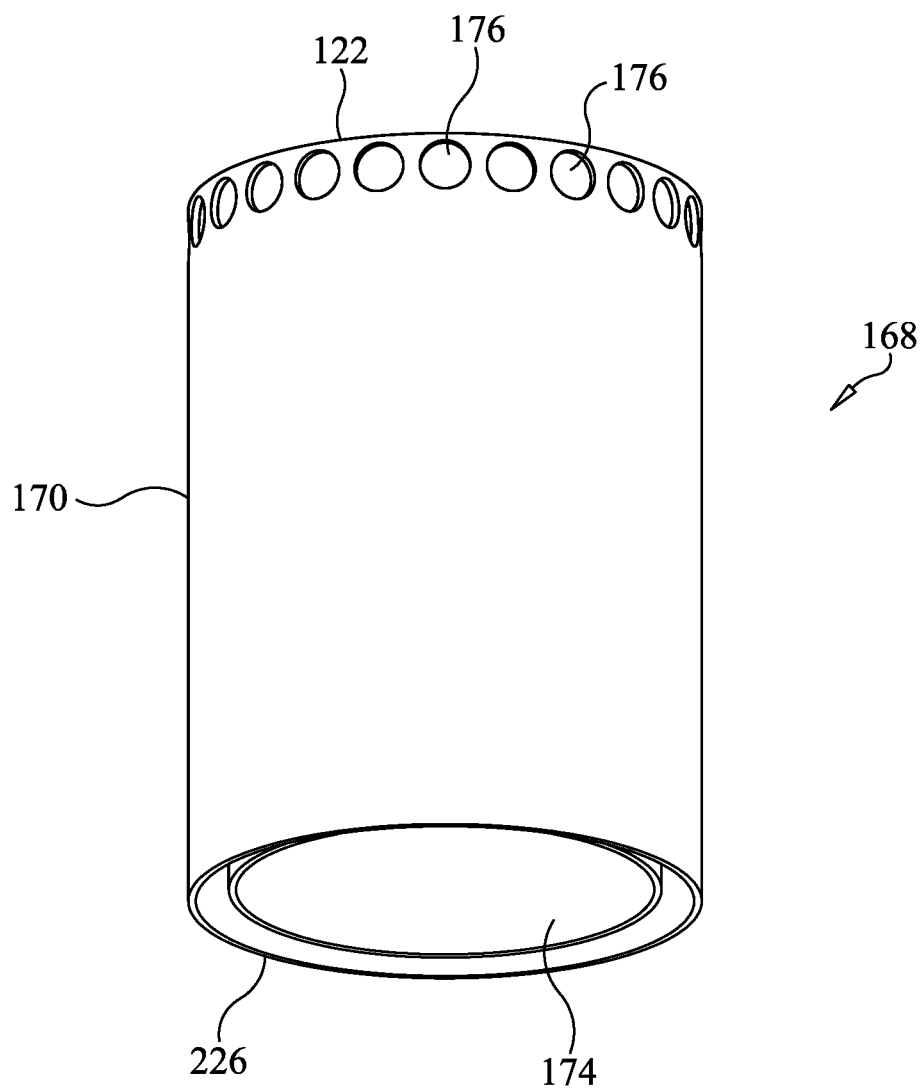
FIG. 23 is a bottom perspective view of the outer containment vessel used in the device of the present invention shown in FIGS. 16-22.
Figure 24:
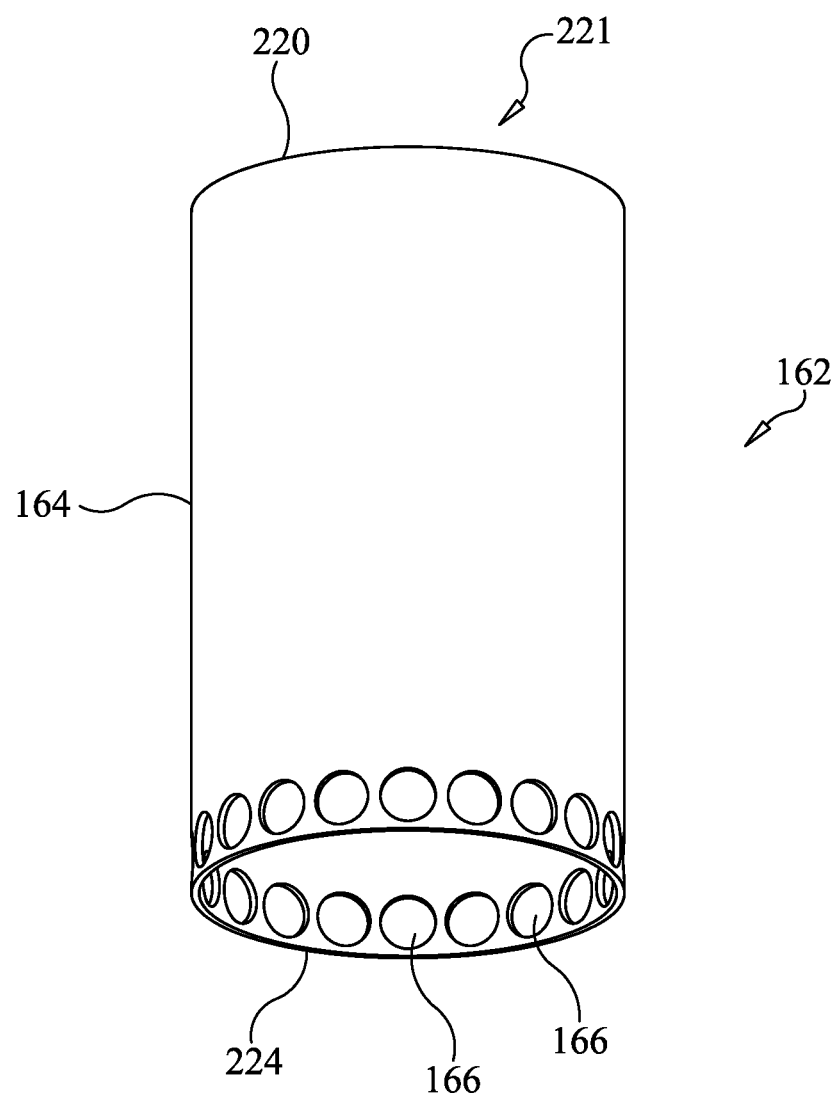
FIG. 24 is a bottom perspective view of the inner containment vessel used in the device of the present invention shown in FIGS. 16-23.
Figure 25:
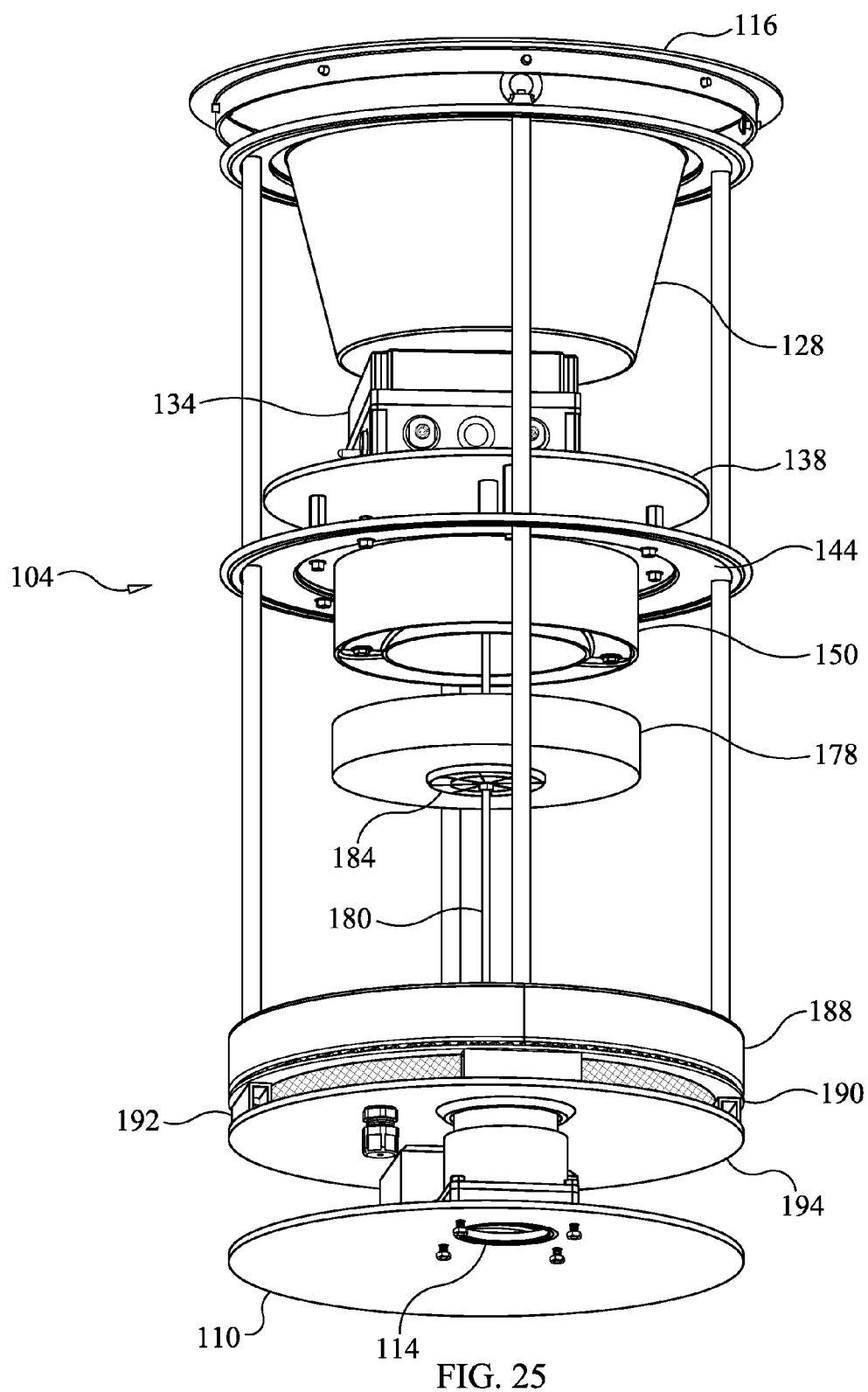
FIG. 25 is a bottom perspective view of the device of the present invention shown in FIGS. 16-24, with the inner and outer containment vessels and the outer canister side wall omitted therefrom.
Figure 26:
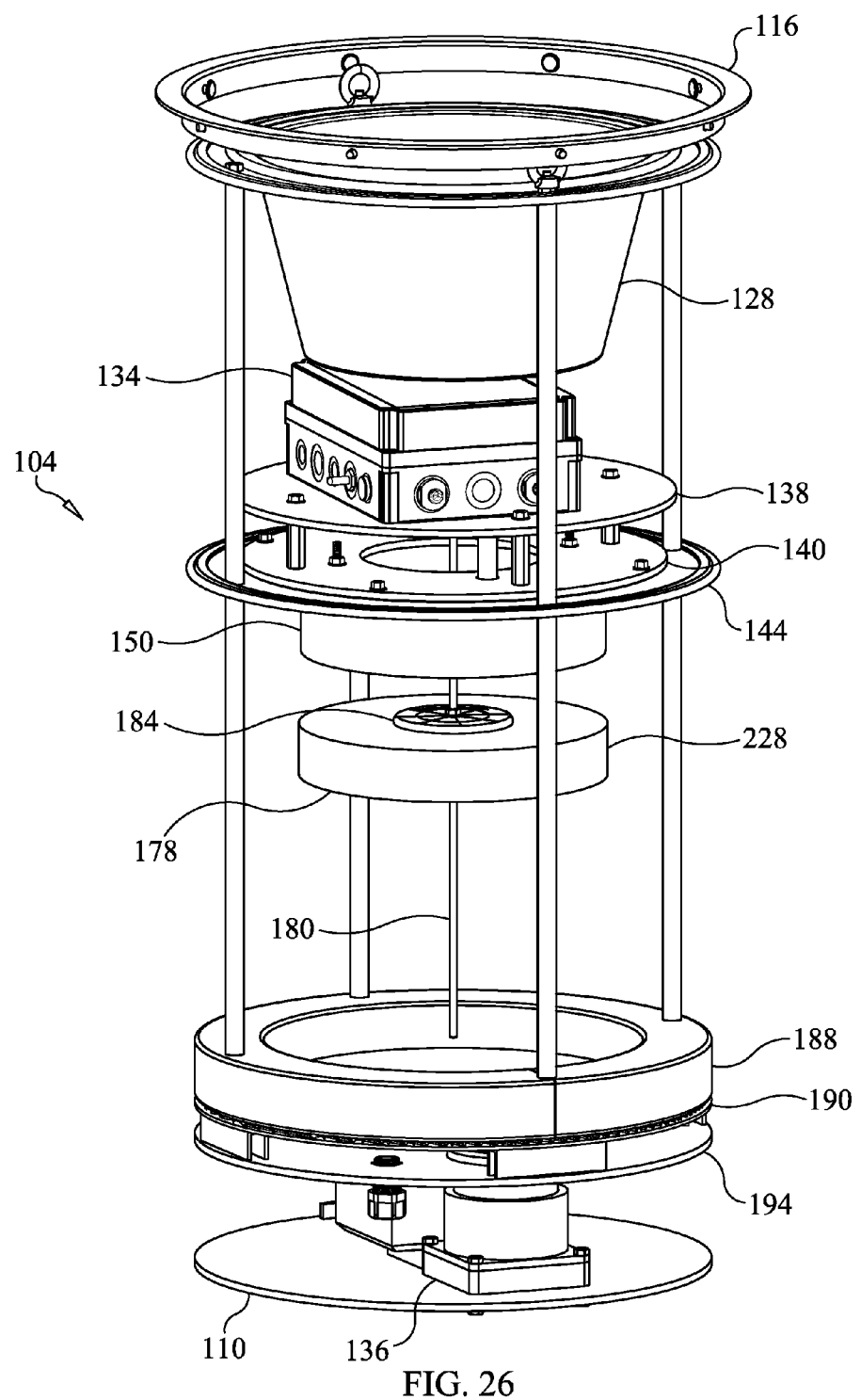
FIG. 26 is a top perspective view of the device of the present invention shown in FIGS. 16-25 with the inner and outer containment vessels and the outer canister side wall omitted therefrom.
Figure 27:
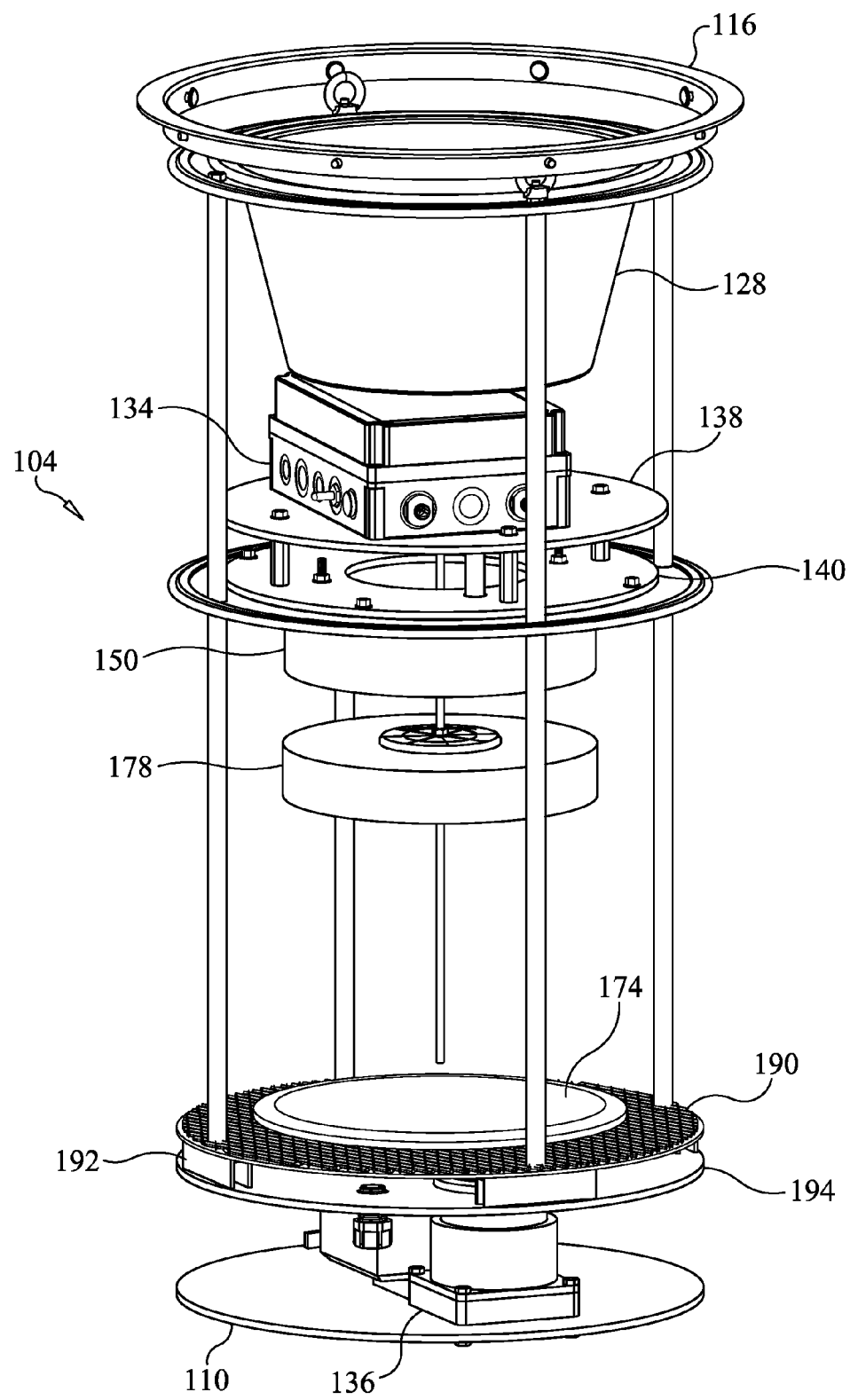
FIG. 27 is a top perspective view of the device of the present invention shown in FIGS. 16-26, with the inner and outer containment vessels, outer canister side wall and post filter member omitted therefrom.
Figure 28:
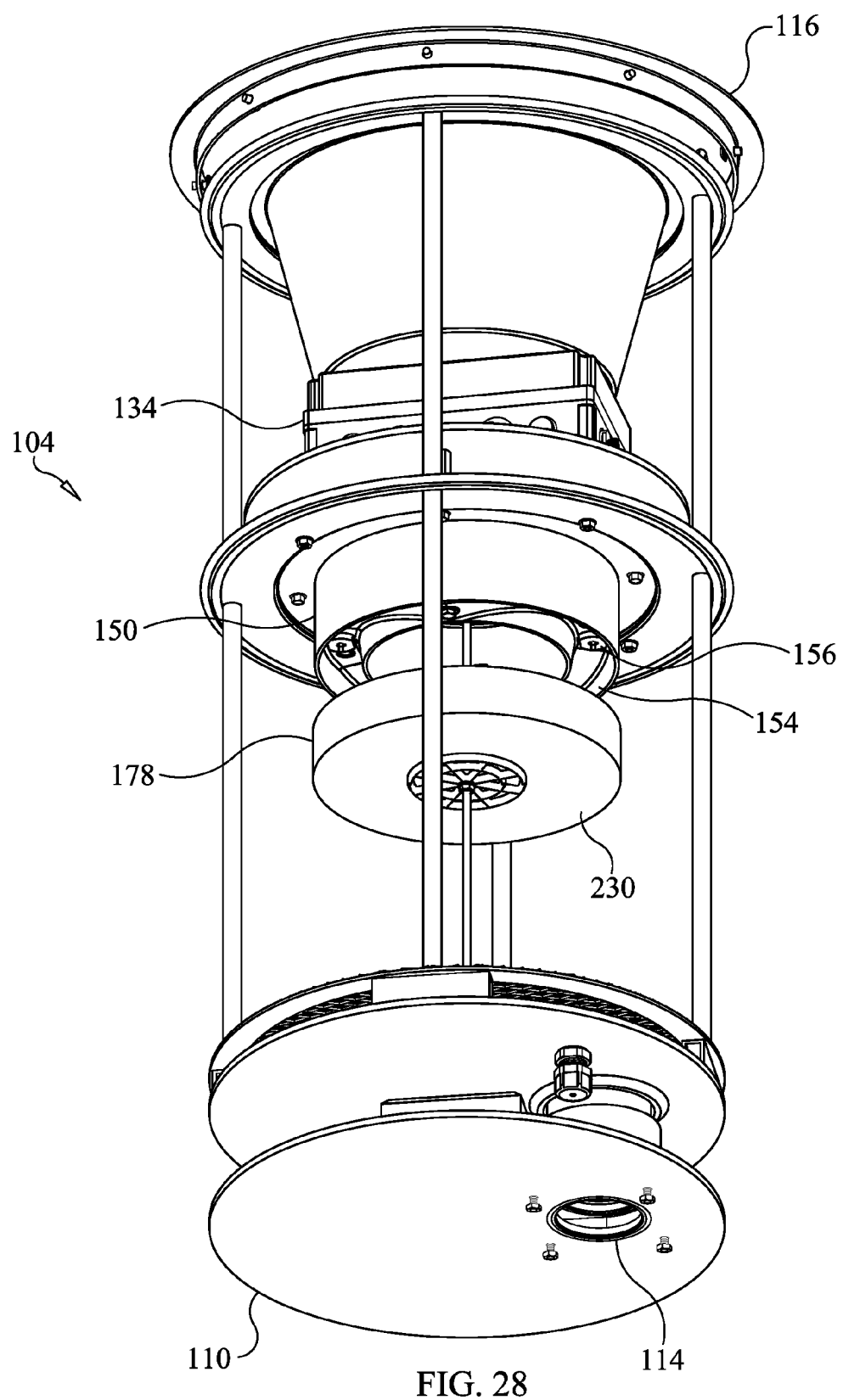
FIG. 28 is a bottom perspective view of the device of the present invention shown in FIGS. 16-27, taken from a different angle from that of FIG. 27, and illustrating the device with the inner and outer containment vessels, outer canister side wall and post filter member omitted therefrom.

A pre-filter 128, having an inverted frusto-conical shape, which is preferably formed as a geotextile sack, rests on a ring-shaped plate 130 situated at the upper portion of the smart cartridge 104 and having a rather substantial central opening through which the pre-filter 128 is placed and on which radial edge of the filter 128 may rest, to provide support for the pre-filter 128 and to allow the pre-filter 128 to be easily removed through the open top side 112 of the canister housing 106 for replacement or cleaning. Runoff water enters through the mounting flange 116 and the open top side 112 of the canister housing 106 and flows into the pre-filter 128, passing through the side wall 132 thereof, as illustrated by FIG. 17 of the drawings. The water then flows downwardly along the interior surface of the cylindrical side wall 108 of the canister housing 106.

The smart cartridge 104 further includes a watertight enclosure 134 which houses the electronic circuitry for automatically closing a valve 136 to prevent water from exiting the outflow pipe of the drainage system when a significant quantity or volume of hydrocarbons in the runoff water is detected thereby. The electronics enclosure 134 rests on the top surface of an upper circular plate 138 forming part of the smart cartridge 104. The diameter of the upper circular plate 138 is less than that of the canister housing 106 measured across the interior bore thereof so that the water may flow between the side wall 108 of the canister housing 106 and the peripheral edge of the upper plate 138.

The smart cartridge 104 of the present invention includes a lower circular plate 140 situated below the upper circular plate 138 and spaced apart from the upper circular plate 138 a predetermined distance by a plurality of spaced apart standoffs 142. The spacing 139 between the upper circular plate 138 and the lower circular plate 140 is important, as it controls the flow of water into the interior of the smart cartridge 104, and the spacing 139 should be selected in anticipation of the volume of runoff water falling into the catch basin where the smart cartridge assembly 100, or multiple smart cartridge assemblies 100, are situated.

The spacing 139 between the upper circular plate 138 and the lower circular plate 140 defines a high velocity inlet for receiving water flow through the bore of the canister housing 106 and the pre-filter 128, and into the smart cartridge 104. Water flowing at this point is turbulent in nature. The lower circular plate 140, like the upper circular plate 138, has a diameter which is preferably less than the interior diameter of the canister housing 106, but, its outer peripheral edge portion rests on a circular ring-shaped flange 144 that extends to and engages the interior surface of the cylindrical side wall 108 of the canister housing 106. This ring-shaped flange 144 has an elastic or rubberized peripheral edge 146, and at least an elastic or rubberized top surface 148 on which the lower circular plate 140 rests, to provide a watertight seal between the canister housing side wall 108 and the lower circular plate 140. This seal 146, 148 causes the runoff water which flows into the canister housing bore along the side wall 108 of the housing 106 to be diverted radially inwardly between the upper circular plate 138 and the lower circular plate 140. The ring-shaped flange 144 defines a central opening through which portions of the smart cartridge 104 are received and supported thereby. The lower circular plate 140 also includes a central opening 149 through which the high velocity, turbulent flow of water may pass into the interior of the smart cartridge 104.

Secured to the underside of the lower circular plate 140 of the smart cartridge 104 is a hydrocarbon fluid accumulator and sensor assembly 150. The accumulator housing 151 is in the form of a circular hub having a central opening 152 which is aligned with the central opening formed in the lower circular plate 140 so that water may pass freely therethrough and into the interior of the smart cartridge 104. As will be explained in greater detail, the purpose of the accumulator 150, as its name implies, is to accumulate any hydrocarbon fluid, such as oil or gas, which has separated from the runoff water flowing into the device 100 of the present invention. The accumulator housing 150 defines two pockets 154 for accumulating hydrocarbon fluids, each pocket 154 having a sensor 156 situated therein for detecting accumulated hydrocarbon fluids which have separated from the water. The sensors 156 are connected to the electrical circuitry within the electronics enclosure 134, and provide a signal to the electrical circuitry when separated hydrocarbon fluid contacts a sensor 156. Within each pocket 154 and extending downwardly therein is an air release tube 158 provided for the purpose of removing any air trapped within each pocket 154 that could prevent the hydrocarbon fluid from rising upwardly into the pockets 154 to contact the sensors 156 therein. A liquid sensor 157 is also mounted on the accumulator housing 150 to detect the presence of water within the chamber 160 and, therefore, to prevent a false hydrocarbon detection signal, as described previously with respect to the first embodiment of the device of the present invention.

The central opening 152 formed in the accumulator housing 150 leads to an interior chamber 160 defined by a double-walled cylindrical structure. More specifically, an inner water containment vessel 162, having a cylindrical side wall 164, defines a low velocity water flow chamber 160 within the interior cavity 165 thereof. The inner containment vessel 162 has an open axial top end 220 defining a water receiving opening 221 which communicates with the interior cavity 165 thereof. The inner containment vessel 162 has a first diameter measured interiorly of the cylindrical side wall 164 thereof. The upper portion of the inner containment vessel 162 surrounds the accumulator housing 150, and the lower portion of the inner containment vessel 162 includes a plurality of openings 166 formed through the thickness of and circumferentially about the side wall 164 thereof to allow water to flow therethrough and out of the low velocity chamber 160.

Encircling the inner containment vessel 162 is an outer water containment vessel 168 having a cylindrical side wall 170 and further having a second diameter measured interiorly, within the interior cavity 169 thereof in which the inner water containment vessel 162 resides, which is greater than the first diameter of the inner containment vessel 162 so as to provide a space 172 between the first and second vessels 162, 168 through which water may flow, as shown in FIG. 17 of the drawings. This second, outer containment vessel 168 is open at the top but engages the underside of the upper circular plate 138 of the smart cartridge 104 to form a seal therewith, and includes a closed bottom wall 174, which engages and forms a seal with the lower edge of the side wall 164 of the inner containment vessel 162. The outer containment vessel 168 includes a plurality of openings 176 formed through the thickness of the side wall 170 thereof at the upper portion thereof about the circumference of the side wall 170 to allow water to flow therethrough, again as can be seen from FIG. 17 of the drawings.

Thus, high velocity water having a turbulent flow enters between the upper circular plate 138 and the lower circular plate 140 of the smart cartridge 104 and passes through the central openings formed through the lower circular plate 140 and the accumulator housing 150, and into the low velocity chamber 160 defined by the interior of the inner containment vessel 162. There, the flow of water slows and becomes less turbulent so that any hydrocarbon fluids, such as gas or oil, can separate from the runoff water and rise to the surface of the water, accumulating in the chamber 160 and in one or both of the pockets 154 of the accumulator 150 in which the sensors 156 reside. The water within the chamber 160 then flows through the plurality of openings 166 formed in the bottom of the inner containment vessel 162 and into the space 172 between the cylindrical side wall 164 of the inner containment vessel 162 and the cylindrical side wall 170 of the outer containment vessel 168, and upwardly therethrough, as can be seen from FIG. 17 of the drawings. The water then flows through the plurality of openings 176 formed in the upper portion of the outer containment vessel 168 and then downwardly again through the smart cartridge 104 within the space 173 between the cylindrical side wall 170 of the outer containment vessel 168 and the cylindrical side wall 108 of the canister housing 106.

To help slow the flow of water within the chamber 160 and, thus, to help separate any hydrocarbon fluids from the water entrained thereby, a diffuser or separator medium 178 may be used. The diffuser or separator medium 178 is a puck-like member formed of a porous material that slows the flow of water therethrough and through the chamber 160. The diffuser or separator medium 178 is mounted on a rod 180 that is suspended centrally through the chamber 160 from the upper circular plate 138, the rod 180 being attached to the upper circular plate 138 at the upper axial end thereof by a turnbuckle or other fastening device 182 which may permit the diffuser or separator medium 178 to be positioned at various axial locations within the low velocity chamber 160. The diffuser or separator medium 178 is further held in place within the low velocity chamber 160 on the rod 180 by upper and lower circular holding plates 184a, 184b positioned on opposite axial sides of the medium 178, which holding plates 184a, 184b may be adjustably mounted on the rod 180 to allow positioning of the diffuser or separator medium 178 axially within the low velocity chamber 160. The diffuser or separator medium 178 has a diameter which is substantially equal to the interior diameter of the chamber 160 in which it is located so that water must flow through the diffuser or separator medium 178 as it passes through the low velocity chamber 160.

Preferably, the annular space between the inner containment vessel side wall 164 and the outer containment vessel side wall 170 essentially defines an inverted weir, at 186 especially, adjacent to the plurality of openings 176 formed in the outer containment vessel side wall 170 where the still waters spills out of the openings 176. This inverted weir, at 186, maintains a constant water height within the low velocity chamber 160 by controlling the flow of still water through the plurality of openings 176 in the outer containment vessel 168. In this regard, reference should be had to FIGS. 32-34 of the drawings.

A ring-shaped post filter member 188 is situated near the bottom portion of the smart cartridge 104 between the side wall 108 of the canister housing 106 and the cylindrical side wall 170 of the outer containment vessel 168. This post filter member 188 is preferably formed from an open cell foam to allow water to pass therethrough but to filter out any fine debris or contaminants carried by the water that is not caught by the pre-filter 128. The post filter member 188 rests on the upper surface of a circular perforated plate 190 extending diametrically across the interior bore of the canister housing 106 and including at least a portion 191 thereof formed with perforations. Thus, water flowing between the side wall 108 of the canister housing 106 and the cylindrical side wall 170 of the outer containment vessel 168 will pass through the post filter member 188 and through the perforated plate 190. The perforated plate 190 also supports the outer containment vessel 168 and the inner containment vessel 162 therewithin, as the bottom wall 174 of the outer containment vessel 168 rests on the upper surface of the perforated plate 190.

Spaced below the perforated plate 190 and separated therefrom and attached thereto by a plurality of spaced apart standoffs 192 is the bottom plate 194 of the smart cartridge 104. The bottom plate 194 defines with the perforated plate 190 a channel 193 through which water may flow to the water outlet opening 114 of the canister housing 106. This bottom plate 194 is solid except for an opening 196 situated at a particular location in which a tube 198 is mounted in a watertight fashion thereto using an elastic or rubberized seal 200. The tube 198 is situated axially in alignment with the opening 114 formed in the bottom wall 110 of the canister housing 106 to which the water drainage outflow pipe is attachable. The diameter of the bottom plate 194 is substantially the same as or slightly less than the interior diameter of the canister housing 106 so that water flowing between the canister housing 106 and the side wall 170 of the outer containment vessel 168 and through the post filter member 188 will be diverted radially inwardly through the channel 193 and toward the water outlet tube 198 connected to the bottom plate 194 of the smart cartridge 104, as can be seen from FIG. 17 of the drawings.

The device of the present invention further includes an electronically actuated, or manually actuated, gate valve 136. The gate valve 136 is situated between the bottom plate 194 of the smart cartridge 104 and the bottom wall 110 of the canister housing 106 in which the smart cartridge 104 is mounted. The gate valve 136 includes a sliding plate 202 that may slide diametrically across the open bottom end of the outlet tube 198 and the water outlet opening 114 formed in the bottom wall 110 of the canister housing 106 to selectively prevent any flow of water passing therethrough and into the water drainage outflow pipe of the drainage system. The gate valve 136 is activated electronically by the electrical circuit situated within the electronics enclosure 134 of the smart cartridge 104 when a volume of hydrocarbon fluid, separated from the water runoff, is detected by the sensors 156 situated in the accumulator 150. The gate valve 136 further includes a valve handle 204 which may be connected to a cable 205 passing upwardly through the smart cartridge 104 and the interior bore of the canister housing 106 and having a grab handle 207 situated at the opposite end thereof near the open top side 112 of the canister housing 106, which grab handle is graspable by a person to effect the manual shut off of water flow and closure of the valve 136.

Figure 29:
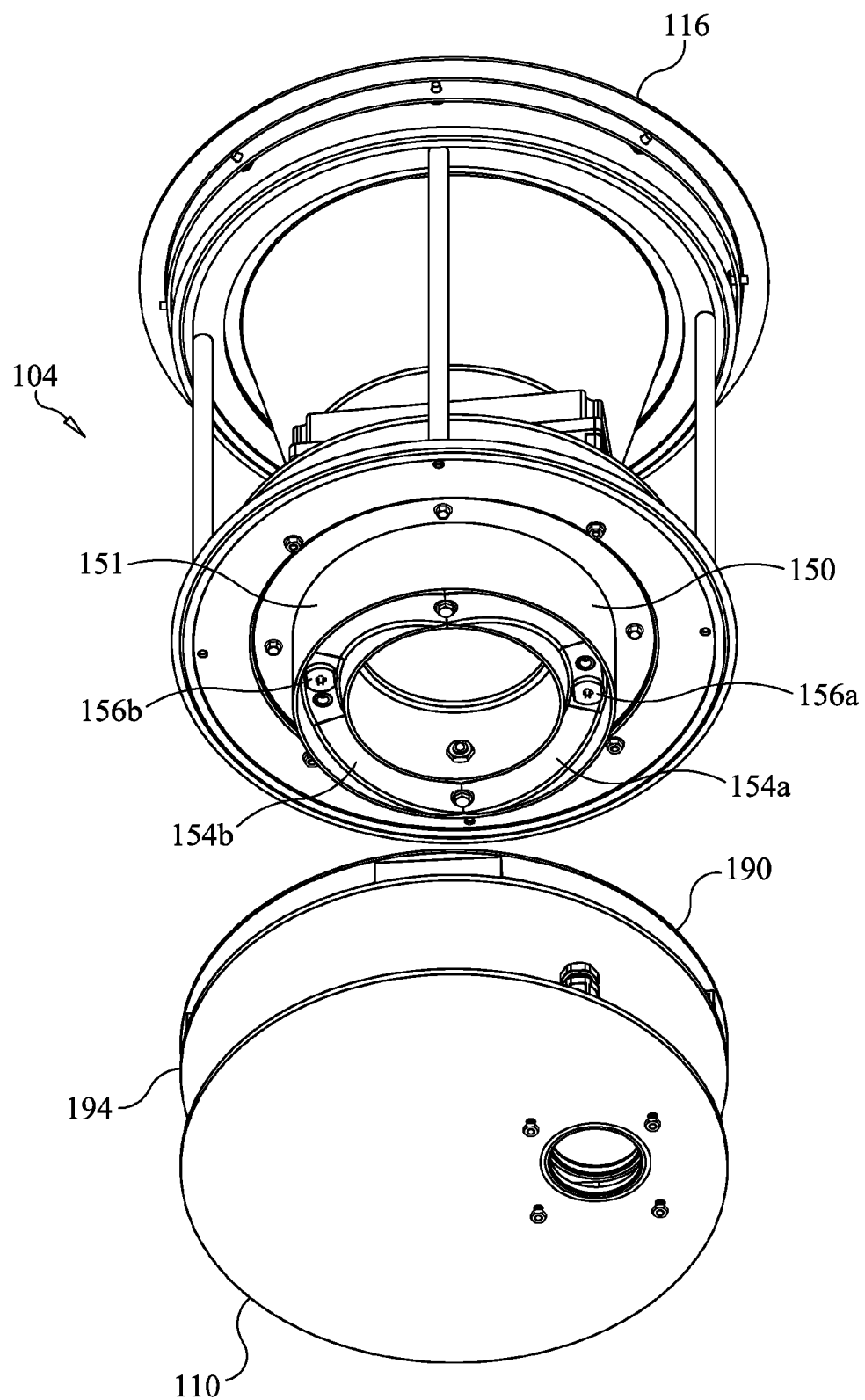
FIG. 29 is a bottom perspective view of the device of the present invention shown in FIGS. 16-28, with several components thereof being omitted from the figure to illustrate the hydrocarbon accumulator and sensors.
Figure 30:
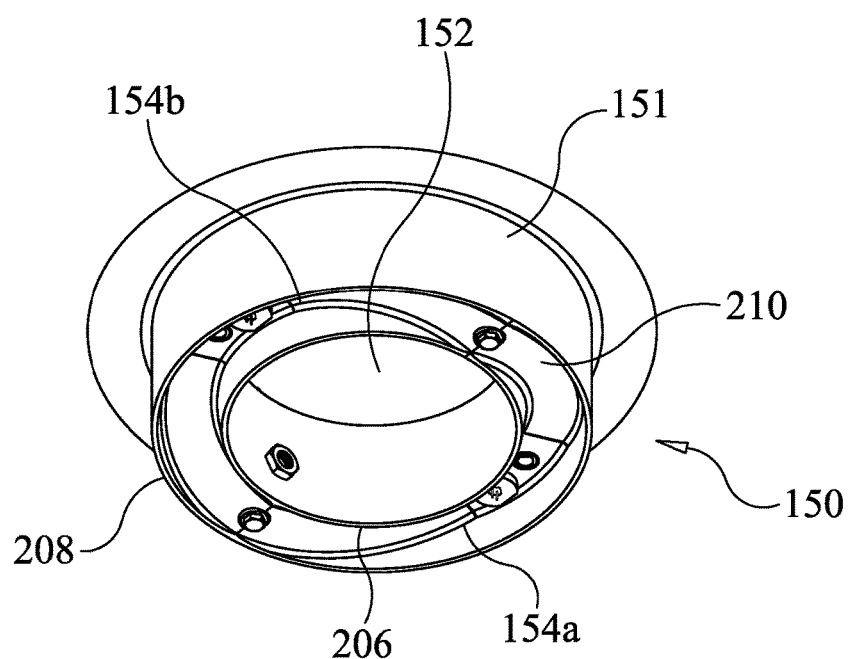
FIG. 30 is a bottom perspective view of the hydrocarbon accumulator used in the device of the present invention shown in FIGS. 16-29.
Figure 31:
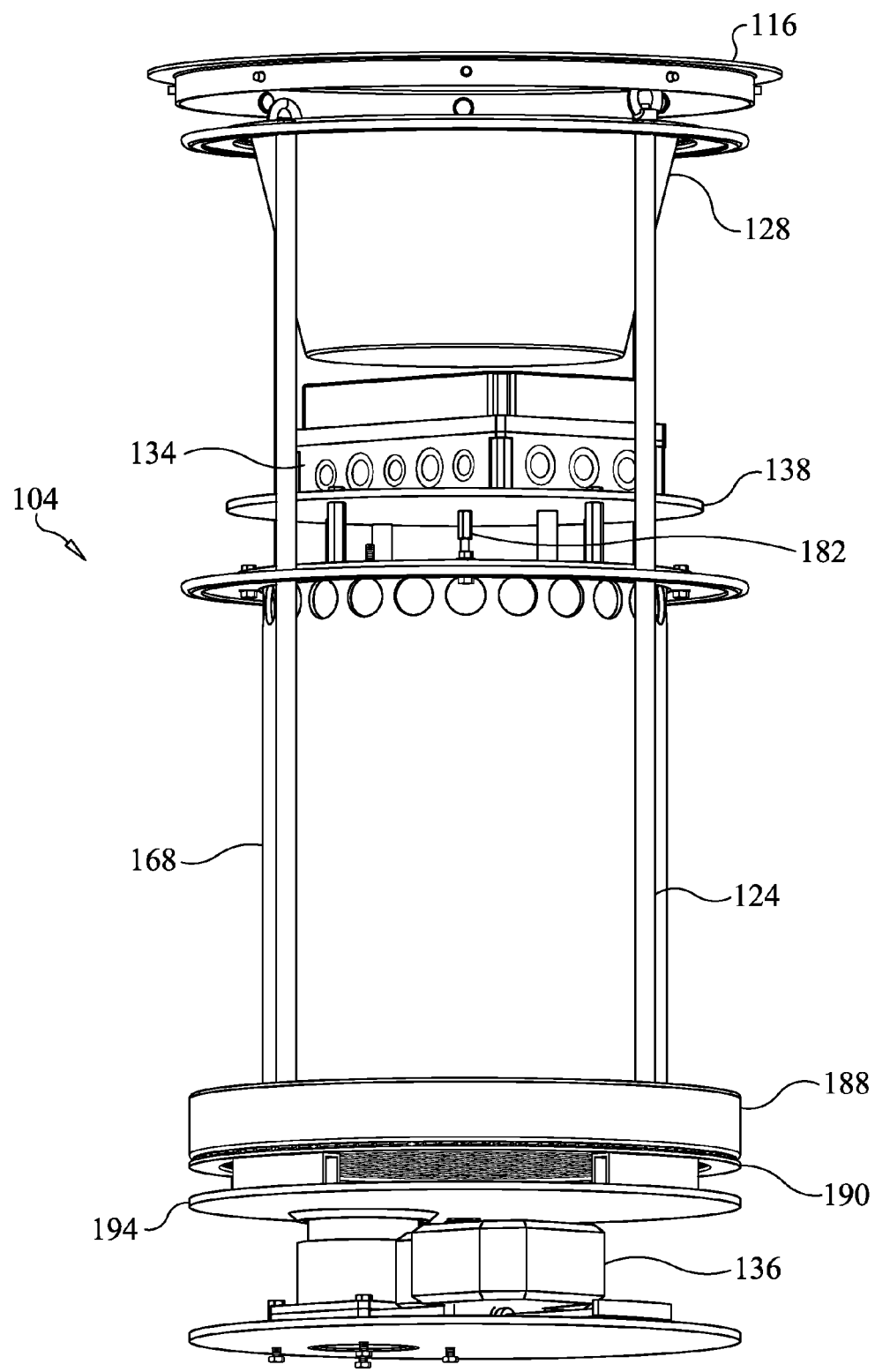
FIG. 31 is another perspective view of the device of the present invention shown in FIGS. 16-30, with the outer canister side wall omitted therefrom to illustrate the actuated gate valve used in the device.
Figure 32:
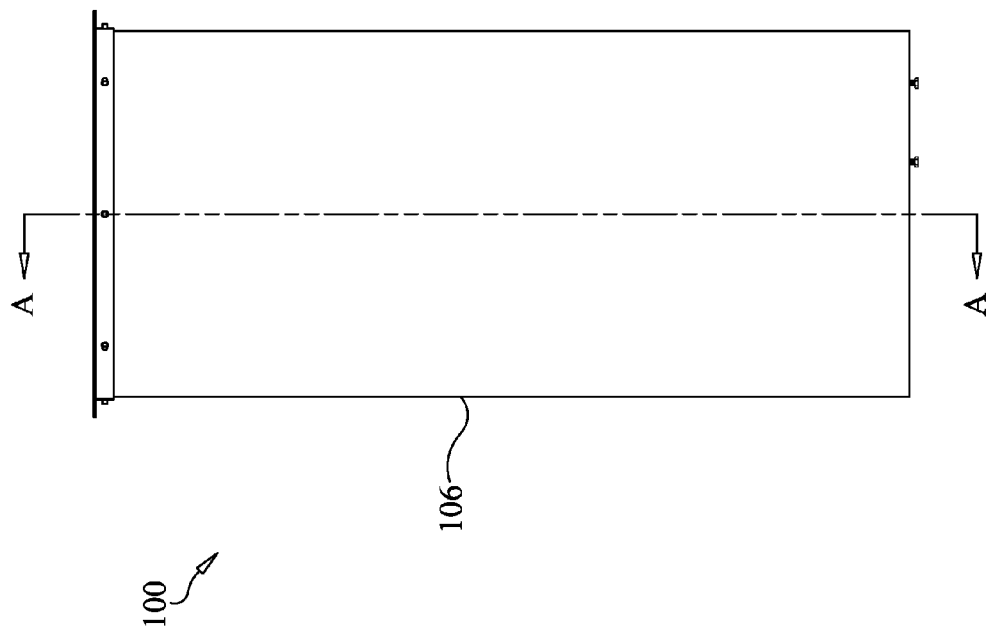
FIG. 32 is a side view of the assembly of the present invention shown in FIG. 17, which includes the outer canister and the smart cartridge mounted therein.
Figures 33, 34:
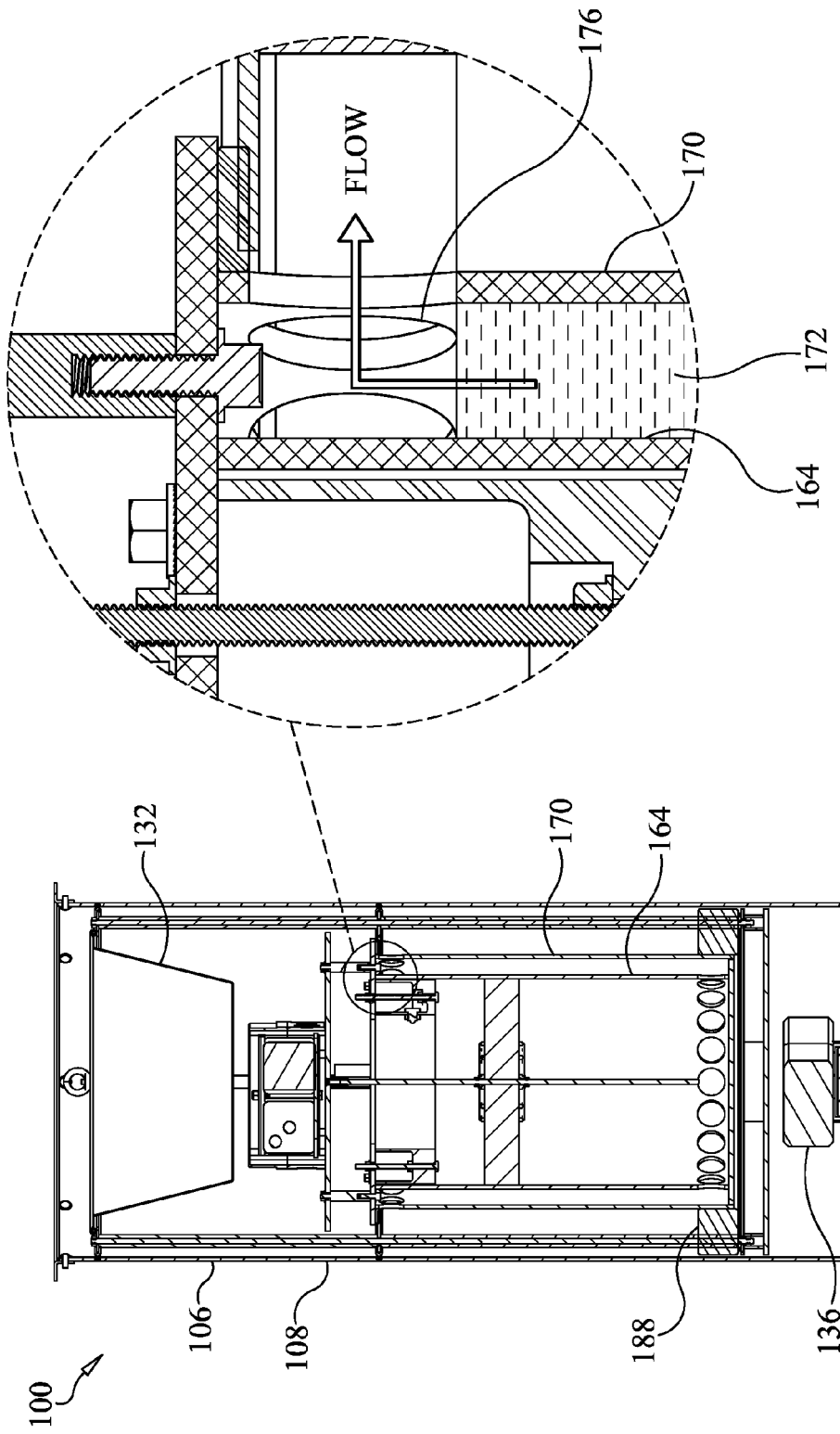
FIG. 33 is a cross-sectional view of the assembly of the present invention shown in FIG. 32, taken along line A-A of FIG. 32.
FIG. 34 is a detailed, cross-sectional view of a portion of the assembly of the present invention shown encircled with broken lines in FIG. 33.

As can be seen from FIGS. 29 and 30 of the drawings, the hydrocarbon fluid accumulator 150 has a hub-shaped housing 151 with concentrically arranged inner and outer radial walls 206, 208 on the bottom side thereof. The inner and outer walls 206, 208 extend to a variably sloping transverse top wall 210 which varies in depth relative to the bottom edge 209 of the inner and outer walls 206, 208 to define two diametrically opposed pockets 154 or chambers in which hydrocarbon fluids may accumulate. At the deepest point in each pocket 154 and mounted to the transverse top wall 210 is situated a sensor 156 which can detect the presence of a hydrocarbon fluid within the pocket 154 when the fluid rises to a level to contact the sensor 156 contained therein. The sensors 156 are connected electrically to the electrical circuit within the electronics enclosure, and provide a signal to the electrical circuit when a hydrocarbon fluid is detected. As a result, the electrical circuit may activate the gate valve 136 to close the water outlet 114 of the device 100 and prevent water flow into the water drainage outflow pipe to which the device 100 of the present invention is connected. In this regard, the electrical circuit of the smart cartridge 104 operates in a manner described previously with respect to the first embodiment of the present invention and shown in FIGS. 1-15 of the drawings.

As mentioned previously, the smart cartridge 104 of the present invention may be removed from the canister 102 in which it is mounted. The exposed lifting rings 122, mentioned previously, are connected to vertical posts 124 which extend axially through the bore of the canister housing 106, the axial ends of which are attached to the bottom plate 194 of the smart cartridge 104 so that the smart cartridge 104, as a unit, may be easily raised through the open top side 112 of the canister housing 106 for maintenance, or replacement of the pre-filter 128 or post filter member 188, or to gain to access to the gate valve 136 situated at the bottom wall 110 of the canister 102.

The apparatus and cartridge of the present invention for detecting the presence of hydrocarbon fluid in runoff water will now be further described.

The apparatus 100 includes an outer canister 102. The outer canister 102 has a housing 106, the housing having a top axial end 112 and a bottom axial end 110 situated opposite the top axial end 112 and a side wall 108 extending between the top axial end 112 and the bottom axial end 110. The canister housing 106 defines an interior cavity 103 and includes a water ingress opening 113 situated in proximity to the top axial end 112 and a water egress opening 114 situated in proximity to the bottom axial end 110. The outer canister 102 further has a valve 136 situated in proximity to the bottom axial end 110, the valve 136 being in communication with the water egress opening 114 and selectively closing the water egress opening 114 in response to a control signal received thereby.

The apparatus 100 further includes a cartridge 104, the cartridge 104 being situated in the interior cavity 103 of the housing 106 of the outer canister 102. The cartridge 104 includes a pre-filter 128, the pre-filter 128 being in fluid communication with the water ingress opening 113 of the canister housing 106 and receiving therein water flowing through the water ingress opening 113. The pre-filter 128 is at least partially water permeable and outputs therefrom pre-filtered water in response to water received thereby flowing through the water ingress opening 113.

The cartridge 104 also includes a water diverter plate 140, the water diverter plate 140 having an opening 149 formed through the thickness thereof The water diverter plate 140 is situated in fluid communication with the pre-filter 128 and thereby receives any pre-filtered water outputted from the pre-filter 128. The water diverter plate 140 diverts the flow of pre-filtered water from the pre-filter 128 so that the pre-filtered water passes through the opening 149 in the water diverter plate 140.

The cartridge 104 further includes an inner containment vessel 162 and an outer containment vessel 168. The inner containment vessel 162 and the outer containment vessel 168 include vessel defining walls 164, 170, the vessel defining walls 164, 170 further defining each of the inner containment vessel 162 and the outer containment vessel 168 with an interior cavity 165, 169. The inner containment vessel 162 is disposed within the interior cavity 169 of the outer containment vessel 168. The vessel defining wall 170 of the outer containment vessel 168 is spaced inwardly from the side wall 108 of the housing 106 of the outer canister 102 and defines a space 173 therebetween for receiving the flow of pre-filtered water therethrough. The vessel defining wall 164 of the inner containment vessel 162 is spaced inwardly of the vessel defining wall 170 of the outer containment vessel 168 and defines a space 172 therebetween for receiving the flow of pre-filtered water therethrough. Each of the inner containment vessel 162 and the outer containment vessel 168 includes an upper axial end 220, 222 and a lower axial end 224, 226 situated opposite the upper axial end 220, 222. The upper axial end 220 of the inner containment vessel 162 is disposed axially in proximity to the upper axial end 222 of the outer containment vessel 168, and the lower axial end 224 of the inner containment vessel 162 is disposed axially in proximity to the lower axial end 226 of the outer containment vessel 168. The vessel defining wall 164 of the inner containment vessel 162 has at least one water flow port 166 formed through the thickness thereof and situated in proximity to the lower axial end 224 thereof to allow the flow of pre-filtered water to pass therethrough and into the space 172 defined by the vessel defining walls 164, 170 of the inner containment vessel 162 and the outer containment vessel 168. The vessel defining wall 170 of the outer containment vessel 168 has at least one water flow port 176 formed through the thickness thereof and situated in proximity to the upper axial end 222 thereof to allow the flow of pre-filtered water in the space 172 between the vessel defining walls 164, 170 of the inner containment vessel 162 and the outer containment vessel 168 to pass therethrough and into the space 173 defined by the vessel defining wall 170 of the outer containment vessel 168 and the side wall 108 of the housing 106 of the outer canister 102. The upper axial end 220 of the inner containment vessel 162 has an opening 221 formed therein to allow the flow of pre-filtered water received through the opening 149 of the water diverter plate 140 to pass therethrough and into the interior cavity 165 of the inner containment vessel 162. The interior cavity 165 of the inner containment vessel 162 defines a chamber 160 in which hydrocarbon liquid carried by the flow of pre-filtered water is at least partially separated from the pre-filtered water.

The cartridge 104 further includes a diffuser/separator member 178 situated within the interior cavity 165 of the inner containment vessel 162, the diffuser/separator member 178 being at least partially permeable to the flow of pre-filtered water therethrough. The diffuser/separator member 178 has a first axial side 228 which is in fluid communication with the opening 221 formed in the upper axial end 220 of the inner containment vessel 162, and a second axial side 230 situated opposite the first axial side 228 and which is in fluid communication with the at least one water flow port 166 of the inner containment vessel 162. The diffuser/separator member 178 acts to slow the flow of pre-filtered water through the interior cavity 165 of the inner containment vessel 162 and thereby helps to effect the separation of hydrocarbon liquid from the pre-filtered water. The hydrocarbon liquid rises to the surface of the pre-filtered water situated above the first axial side 228 of the diffuser/separator member 178.

The cartridge 2 further includes a hydrocarbon fluid accumulator 150, the hydrocarbon fluid accumulator 150 being positioned in fluid communication with the pre-filtered water, and any hydrocarbon liquid separated therefrom, and situated above the first axial side 228 of the diffuser/separator member 178. The hydrocarbon fluid accumulator 150 has a housing 151 defining at least one pocket 154 for accumulating hydrocarbon liquid therein which has separated from the pre-filtered water. The hydrocarbon fluid accumulator 150 further includes at least one sensor 156. The at least one sensor 156 resides in the at least one pocket 154 and detects the presence of hydrocarbon liquid accumulating within the at least one pocket 154, the at least one sensor 156 generating a sensor signal when a hydrocarbon liquid is detected thereby.

The cartridge 104 further includes a post filter member 188. The post filter member 188 is situated in fluid communication with the space 173 between and defined by the vessel defining wall 170 of the outer containment vessel 168 and the side wall 108 of the housing 106 of the outer canister 102. The post filter member 188 is at least partially water permeable and outputs therefrom post-filtered water in response to pre-filtered water received thereby flowing through the space 173 between the vessel defining wall 170 of the outer containment vessel 168 and the side wall 108 of the housing 106 of the outer canister 102. The post-filtered water selectively flows through the water egress opening 114 of the housing 106 of the outer canister 102.

The cartridge 104 further includes an electronic circuit 44, the electronic circuit 44 being in electrical communication with the at least one sensor 156 of the hydrocarbon accumulator 150. The electronic circuit 44 is responsive to the sensor signal generated by the at least one sensor 156 and generates the control signal in response thereto to cause the valve 136 to selectively close the water egress opening 114.

In another form of the present invention, an apparatus 100 for detecting the presence of hydrocarbon fluid in runoff water includes an outer canister 102, the outer canister 102 having a housing 106. The housing 106 has a top axial end 112 and a bottom axial end 110 situated opposite the top axial end 112 and a side wall 108 extending between the top axial end 112 and the bottom axial end 110. The canister housing 106 defines an interior cavity 103 and includes a water ingress opening 113 situated in proximity to the top axial end 112 and a water egress opening 114 situated in proximity to the bottom axial end 110. The outer canister 102 further has a valve 136 situated in proximity to the bottom axial end 10, the valve 136 being in communication with the water egress opening 114 and selectively closing the water egress opening 114 in response to a control signal received thereby.

The apparatus 100 further includes a cartridge 104, the cartridge 104 being situated in the interior cavity 103 of the housing 106 of the outer canister 102. The cartridge 104 includes a pre-filter 128, the pre-filter 128 being in communication with the water ingress opening 113 of the canister housing 106 and receiving therein water flowing through the water ingress opening 113. The pre-filter 128 is at least partially water permeable and outputs therefrom pre-filtered water in response to water received thereby flowing through the water ingress opening 113.

The cartridge 104 further includes at least one containment vessel 162, the at least one containment vessel 162 including a vessel defining wall 164, the vessel defining wall 164 further defining the at least one containment vessel 162 with an interior cavity 165. The interior cavity 165 of the at least one containment vessel 162 defines a chamber 160 in which hydrocarbon liquid carried by the flow of pre-filtered water is at least partially separated from the pre-filtered water. The at least one containment vessel 162 includes a first axial end 220 and a second axial end 224 situated opposite the first axial end 220. The vessel defining wall 164 of the at least one containment vessel 162 has a water input opening 221 situated in proximity to the first axial end 220 thereof to allow the flow of pre-filtered water outputted by the pre-filter 128 to pass therethrough and into the interior cavity 165 of the at least one containment vessel 162. The vessel defining wall 164 of the at least one containment vessel 162 has a water output opening 166 formed through the thickness thereof and situated in proximity to the second axial end 224 thereof to allow the flow of pre-filtered water to pass therethrough and out of the interior cavity 165 of the at least one containment vessel 162.

The cartridge 104 further includes a diffuser/separator member 178 situated within the interior cavity 165 of the at least one containment vessel 162, the diffuser/separator member 178 being at least partially permeable to the flow of pre-filtered water therethrough. The diffuser/separator member 178 has a first axial side 228 which is in fluid communication with the water input opening 221 of the at least one containment vessel 162 and a second axial side 230 situated opposite the first axial side 228 and which is in fluid communication with the water output opening 166 of the at least one containment vessel 162. The diffuser/separator member 178 acts to slow the flow of pre-filtered water through the interior cavity 165 of the at least one containment vessel 162 and thereby helps to effect the separation of hydrocarbon liquid from the pre-filtered water. The hydrocarbon liquid rises to the surface of the pre-filtered water situated above the first axial side 228 of the diffuser/separator member 178.

The cartridge 104 further includes a hydrocarbon fluid accumulator 150, the hydrocarbon fluid accumulator 150 being positioned in fluid communication with the pre-filtered water, and any hydrocarbon liquid separated therefrom, and situated above the first axial side 228 of the diffuser/separator member 178. The hydrocarbon fluid accumulator 150 has a housing 151 defining at least one pocket 154 for accumulating hydrocarbon liquid therein which has separated from the pre-filtered water. The hydrocarbon fluid accumulator 150 further includes at least one sensor 156, the at least one sensor 156 residing in the at least one pocket 154 and detecting the presence of hydrocarbon liquid accumulating within the at least one pocket 154. The at least one sensor 156 generates a sensor signal when a hydrocarbon liquid is detected thereby.

The cartridge 104 further includes an electronic circuit 44, the electronic circuit 44 being in electrical communication with the at least one sensor 156 of the hydrocarbon fluid accumulator 150. The electronic circuit 44 is responsive to the sensor signal generated by the at least one sensor 156 and generates the control signal in response thereto to cause the valve 136 to selectively close the water egress opening 114.

In a preferred form, the cartridge 104 of the apparatus 100 for detecting the presence of hydrocarbon fluid in runoff water further includes a water diverter plate 104. The water diverter plate 140 has an opening 149 formed through the thickness thereof. The water diverter plate 140 is situated in fluid communication with the pre-filter 128 and thereby receives any pre-filtered water outputted by the pre-filter 128. The water diverter plate 140 diverts the flow of pre-filtered water from the pre-filter 128 so that the pre-filtered water passes through the opening 149 in the water diverter plate 140. The water input opening 221 of the at least one containment vessel 162 is in fluid communication with the opening 149 in the water diverter plate 140.

In another preferred form, the cartridge 104 of the apparatus 100 for detecting the presence of hydrocarbon fluid in runoff water further includes an upper plate 138, the upper plate 138 being disposed axially with respect to the water diverter plate 140 and being spaced apart therefrom a predetermined distance. The upper plate 138 and the water diverter plate 140 together define a space 139 therebetween which is in fluid communication with the water input opening 221 of the at least one containment vessel 162 for directing the flow of pre-filtered water toward the water input opening 221 of the at least one containment vessel 162.

In yet another form of the present invention, the at least one containment vessel of the cartridge 104 further includes an inner containment vessel 162 and an outer containment vessel 168. The inner containment vessel 162 and the outer containment vessel 168 include a first vessel defining wall 164 and a second vessel defining wall 170, respectively. The first and second vessel defining walls 164, 170 further respectively define the inner containment vessel 162 and the outer containment vessel 168 with a first interior cavity 165 and a second interior cavity 169, the inner containment vessel 162 being disposed within the second interior cavity 169 of the outer containment vessel 168. The second vessel defining wall 170 of the outer containment vessel 168 is spaced inwardly from the side wall 108 of the housing 106 of the outer canister 162 and defines a space 173 therebetween for receiving the flow of pre-filtered water therethrough. The first vessel defining wall 164 of the inner containment vessel 162 is spaced inwardly of the second vessel defining wall 170 of the outer containment vessel 168 and defines a space 172 therebetween for receiving the flow of pre-filtered water therethrough. Each of the inner containment vessel 162 and the outer containment vessel 168 includes an upper axial end 220, 222 and a lower axial end 224, 226 situated opposite the upper axial end 220, 222. The upper axial end 220 of the inner containment vessel 162 is disposed axially in proximity to the upper axial end 222 of the outer containment vessel 168, and the lower axial end 224 of the inner containment vessel 162 is disposed axially in proximity to the lower axial end 226 of the outer containment vessel 168. The water input opening 221 is formed in the upper axial end 220 of the inner containment vessel 162 to allow the flow of pre-filtered water to pass therethrough and into the first interior cavity 165 of the inner containment vessel 162. The first interior cavity 165 of the inner containment vessel 162 defines the chamber 160 in which hydrocarbon liquid carried by the flow of pre-filtered water is at least partially separated from the pre-filtered water. The water output opening includes at least one first water flow port 166 and at least one second water flow port 176. The at least one first water flow port 166 is formed through the thickness of the first vessel defining wall 164 of the inner containment vessel 162 and situated in proximity to the lower axial end 224 thereof to allow the flow of pre-filtered water to pass therethrough and into the space 172 defined by the first and second vessel defining walls 164, 170 of the inner containment vessel 162 and the outer containment vessel 168. The at least one second water flow port 176 is formed through the thickness of the second vessel defining wall 170 of the outer containment vessel 168 and situated in proximity to the upper axial end 222 thereof to allow the flow of pre-filtered water in the space 172 between the first and second vessel defining walls 164, 170 of the inner containment vessel 162 and the outer containment vessel 168 to pass therethrough and into the space 173 defined by the second vessel defining wall 170 of the outer containment vessel 168 and the side wall 108 of the housing 106 of the outer canister 102.

Preferably, the cartridge 104 of the apparatus 100 for detecting the presence of hydrocarbon fluid in runoff water further includes a post filter member 188. The post filter member 188 is situated in fluid communication with the space 173 between and defined by the second vessel defining wall 170 of the outer containment vessel 168 and the side wall 108 of the housing 106 of the outer canister 102. The post filter member 188 is at least partially water permeable and outputs therefrom post-filtered water in response to pre-filtered water received thereby flowing through the space 173 between the second vessel defining wall 170 of the outer containment vessel 168 and the side wall 108 of the housing 106 of the outer canister 102, the post-filtered water selectively flowing through the water egress opening 114 of the housing 106 of the outer canister 102.

In still another form of the present invention, the cartridge 104 of the apparatus 100 for detecting the presence of hydrocarbon fluid in runoff water further includes a first bottom plate 190 and a second bottom plate 194. The first bottom plate 190 has a perforated portion 191, the perforated portion 191 having perforations formed through the thickness thereof The post filter member 188 is situated in alignment with the perforated portion 191 of the first bottom plate 190 such that post-filtered water outputted from the post filter member 188 passes through the perforations of the perforated portion 191 of the first bottom plate 190. The second bottom plate 194 is disposed axially with respect to the first bottom plate 190 and spaced apart therefrom to define a channel 193 therebetween for receiving post-filtered water flowing through the perforations of the perforated portion 191 of the first bottom plate 190. The second bottom plate 194 includes an opening 196 formed through the thickness thereof, the opening 196 being in fluid communication with the water egress opening 114 of the housing 106 of the outer canister 102. The channel 193 defined by the first bottom plate 190 and the second bottom plate 194 is in fluid communication with the opening 196 formed in the second bottom plate 194 and directs the flow of post-filtered water to the opening 196 formed in the second bottom plate 194.

The cartridge 104 of the apparatus 100 for detecting the presence of hydrocarbon fluid in runoff water is preferably removable from the interior cavity 103 of the outer canister 102. To effect the removal of the cartridge 104 from the outer canister 102, the cartridge 104 may further include at least one post 124 having opposite axial ends, and at least one lifting member 122 situated on one of the opposite axial ends of the at least one post 124. The at least one post 124 is operatively coupled to at least one of the pre-filter 128 and the at least one containment vessel 162, 168 to facilitate removal of the cartridge 104 from the interior cavity 103 of the housing 106 of the outer canister 102. The at least one post 124 could be coupled to other components of the cartridge 104 to permit the entire cartridge 104 to be lifted free of the outer canister 102.

In yet another form of the present invention, the cartridge 104 of the apparatus 100 for detecting the presence of hydrocarbon fluid in runoff water further includes a rod 180, the rod 180 being situated within the interior cavity 165 of the at least one containment vessel 162. The diffuser/separator member 178 is mounted on the rod 180 and is positionable thereon at various axial locations along at least a portion of the axial length of the rod 180. The cartridge 104 may further include first and second holding plates 184*a*, 184*b*. The first holding plate 184*a* is mounted on the rod 180 and situated on the first axial side 228 of the diffuser/separator member 178, and the second holding plate 184*b* is mounted on the rod 180 and situated on the second axial side 270 of the diffuser/separator member 178.

In a preferred form, the housing 151 of the hydrocarbon fluid accumulator 150 of the cartridge 104 is hub-shaped with concentrically arranged inner and outer radial walls 206, 208, each of the inner and outer walls 206, 208 having a bottom edge 209, and a variably sloping transverse top wall 210 which varies in depth relative to the bottom edge 209 of the inner and outer walls 206, 208 to thereby define the at least one pocket 154 with diametrically opposed first and second pockets 154*a*, 154*b* in which hydrocarbon liquid may accumulate. Also, preferably, the at least one sensor 156 includes a first sensor 156*a* and a second sensor 156*b*. The first sensor 156*a* resides in the first pocket 154*a* and the second sensor 156*b* resides in the second pocket 154*b*. Each of the first sensor 156*a* and the second sensor 156*b* detects the presence of hydrocarbon liquid accumulating within the first pocket 154*a* and the second pocket 154*b*, respectively.

Each of the first sensor 156a and the second sensor 156b generates a sensor signal when a hydrocarbon liquid is detected thereby, the sensor signals of the first sensor 156a and of the second sensor 156b being provided to the electronic circuit 44.

In yet another embodiment, the housing 151 of the hydrocarbon fluid accumulator 150 of the cartridge 104 defines the at least one pocket 154 with a first pocket 154a and a second pocket 154b, the first pocket 154a being disposed diametrically opposite the second pocket 154b. Each of the first pocket 154a and the second pocket 154b is provided for accumulating hydrocarbon liquid therein which has separated from the pre-filtered water. Also, preferably, the at least one sensor 156 includes a first sensor 156a and a second sensor 156b. The first sensor 156a resides in the first pocket 154a and the second sensor 156b resides in the second pocket 154b. The first sensor 156a and the second sensor 156b detect the presence of hydrocarbon liquid accumulating within the first pocket 154a and the second pocket 154b, respectively. The first sensor 156a and the second sensor 156b generate sensor signals when a hydrocarbon liquid is detected thereby, the sensor signals being provided to the electronic circuit 44.

The valve 136 of the apparatus 100 for detecting the presence of hydrocarbon fluid in runoff water is preferably an electronically actuated gate valve. The electronically actuated gate valve 136 includes a sliding plate 202 which is in fluid communication with the water egress opening 114 of the housing 106 of the outer canister 102. The sliding plate 202 is positionable in a first position in which the sliding plate 202 closes the water egress opening 114 to the flow of water therethrough, and a second position in which the sliding plate 202 opens the water egress opening 114 to the flow of water therethrough.

In yet another form, the valve 136 is electronically actuatable and mechanically actuatable to selectively close the water egress opening 114. The valve 136 includes a cable 205 mounted thereto and extending therefrom, the cable 205 including a first end operatively coupled to the valve 136, and a second end situated opposite the first end, and a grab handle 207 situated on the second end of the cable 205. The grab handle 207 is graspable by a person to effect a mechanical closure of the water egress opening 114 by the valve 136.

The present invention is also directed to a cartridge for use in a storm water drainage system. The cartridge detects the presence of hydrocarbon fluid in runoff water flowing into the storm water drainage system and actuates a valve when hydrocarbon fluid in the runoff water is detected. The cartridge is receivable in an outer canister. The outer canister has a housing, the housing having a top axial end and a bottom axial end situated opposite the top axial end and a side wall extending between the top axial end and the bottom axial end. The canister housing defines an interior cavity in which the cartridge is received, and includes a water ingress opening situated in proximity to the top axial end and a water egress opening situated in proximity to the bottom axial end. The canister further has a valve situated in proximity to the bottom axial end, the valve being in communication with the water egress opening and selectively closing the water egress opening in response to a control signal received thereby and generated by the cartridge.

Preferably, the cartridge includes a pre-filter, the pre-filter being in communication with the water ingress opening of the canister housing and receiving therein water flowing through the water ingress opening. The pre-filter is at least partially water permeable and outputs therefrom pre-filtered water in response to water received thereby flowing through the water ingress opening.

The cartridge further preferably includes at least one containment vessel, the at least one containment vessel including a vessel defining wall. The vessel defining wall further defines the at least one containment vessel with an interior cavity, the interior cavity of the at least one containment vessel defining a chamber in which hydrocarbon liquid carried by the flow of pre-filtered water is at least partially separated from the pre-filtered water. The at least one containment vessel includes a first axial end and a second axial end situated opposite the first axial end. The vessel defining wall of the at least one containment vessel has a water input opening situated in proximity to the first axial end thereof to allow the flow of pre-filtered water outputted by the pre-filter to pass therethrough and into the interior cavity of the at least one containment vessel. The vessel defining wall of the at least one containment vessel also has a water output opening formed through the thickness thereof and situated in proximity to the second axial end thereof to allow the flow of pre-filtered water to pass therethrough and out of the interior cavity of the at least one containment vessel.

The cartridge further includes a diffuser/separator member situated within the interior cavity of the at least one containment vessel. The diffuser/separator member is at least partially permeable to the flow of pre-filtered water therethrough. The diffuser/separator member has a first axial side which is in fluid communication with the water input opening of the at least one containment vessel and a second axial side situated opposite the first axial side and which is in fluid communication with the water output opening of the at least one containment vessel. The diffuser/separator member acts to slow the flow of pre-filtered water through the interior cavity of the at least one containment vessel and thereby helps to effect the separation of hydrocarbon liquid from the pre-filtered water, the hydrocarbon liquid rising to the surface of the pre-filtered water situated above the first axial side of the diffuser/separator member.

The cartridge also further includes a hydrocarbon fluid accumulator. The hydrocarbon fluid accumulator is positioned in fluid communication with the pre-filtered water, and any hydrocarbon liquid separated therefrom, and situated above the first axial side of the diffuser/separator member. The hydrocarbon fluid accumulator has a housing defining at least one pocket for accumulating hydrocarbon liquid therein which has separated from the pre-filtered water. The hydrocarbon fluid accumulator further includes at least one sensor, the at least one sensor residing in the at least one pocket and detecting the presence of hydrocarbon liquid accumulating within the at least one pocket. The at least one sensor generates a sensor signal when a hydrocarbon liquid is detected thereby.

The cartridge further includes an electronic circuit, the electronic circuit being in electrical communication with the at least one sensor of the hydrocarbon fluid accumulator. The electronic circuit is responsive to the sensor signal generated by the at least one sensor and generates the control signal in response thereto to cause the valve to selectively close the water egress opening.

In yet another form of the present invention, a cartridge 2 for use in a storm water drainage system detects the presence of hydrocarbon fluid in runoff water flowing into the storm water drainage system and blocks the flow of runoff water thereinto when hydrocarbon fluid in the runoff water is detected. The cartridge 2 preferably includes a housing 4, the housing 4 having a side wall 8, an upper axial wall 12 and a lower axial wall 10 situated opposite the upper axial wall 12. The housing 4 defines an interior cavity 6. At least one of the side wall 8 and the upper axial wall 12 of the housing 4 has a runoff water ingress port 22 formed through the thickness thereof for receiving runoff water flowing into the water drainage system. The interior cavity 6 of the cartridge housing 4 is in fluid communication with the water runoff ingress port 22 and receives therein runoff water passing through the runoff water ingress port 22. At least one of the side wall 8 and the lower axial wall 10 of the housing 4 has a runoff water egress port 48 formed through the thickness thereof, the runoff water egress port 48 being in fluid communication with the interior cavity 6 of the cartridge housing 4 and selectively receiving and passing therethrough runoff water received by the interior cavity 6 of the cartridge housing 4.

The cartridge 2 further preferably includes a debris filter medium 24, the debris filter medium 24 being situated in fluid communication with the runoff water ingress port 22. The debris filter medium 24 is at least partially permeable to runoff water and provides runoff water that is debris filtered to the interior cavity 6 of the cartridge housing 4.

The cartridge 2 also preferably includes a first inner wall 26, the first inner wall 26 being situated within the interior cavity 6 of the cartridge housing 4. The first inner wall 26 has a plurality of slots 28 formed through the thickness thereof, the slots 28 of the plurality of slots being disposed in alignment with the debris filter medium 24 and receiving therethrough debris-filtered runoff water outputted by the debris filter medium 24. The cartridge 2 also includes a second inner wall 30. The second inner wall 30 is situated within the interior cavity 6 of the cartridge housing 4 and is spaced over at least a portion thereof from the first inner wall 26. There are also preferably a plurality of separator walls 32. The separator walls 32 of the plurality of separator walls extend transversely between and are joined to the first inner wall 26 and the second inner wall 30. The separator walls 32, first inner wall 26 and second inner wall 30 together define a plurality of flow through channels 34 extending axially within the interior cavity 6 of the cartridge housing 4 in a direction towards the lower axial wall 10 of the cartridge housing 4. The flow through channels 34 are in fluid communication with the slots 28 formed through the thickness of the first inner wall 26 for receiving the debris-filtered runoff water passing through the slots 28, the flow through channels 34 directing the flow of debris-filtered runoff water towards the lower axial wall 10 of the cartridge housing 4.

Preferably, the cartridge 2 further includes a weir 31. The weir 31 is disposed within the interior cavity 6 of the cartridge housing 4 and is situated therein in proximity to the lower axial wall 10 thereof. The weir 31 is in fluid communication with the flow through channels 34 to receive the debris-filtered runoff water flowing through the channels 34. The weir 31 acts on the flow of debris-filtered runoff water received thereby to slow movement of the flow of debris-filtered runoff water thereby helping to effect a separation of hydrocarbon liquid from the debris-filtered runoff water received by the weir 31. The hydrocarbon liquid rises to the surface of the debris-filtered runoff water slowed by the weir 31.

The cartridge 2 further includes a hydrocarbon fluid accumulator 58. The hydrocarbon fluid accumulator 58 is situated within the interior cavity 6 of the cartridge housing 4 and in proximity to the weir 31. The hydrocarbon fluid accumulator 58 is in fluid communication with the debris-filtered runoff water slowed in movement by the weir 31.

The hydrocarbon fluid accumulator 58 has a housing 62 defining at least one pocket 70 for accumulating hydrocarbon liquid therein which has separated from the debris-filtered runoff water. The hydrocarbon fluid accumulator 58 further includes at least one sensor 74, the at least one sensor 74 residing in the at least one pocket 70 and detecting the presence of hydrocarbon liquid accumulating within the at least one pocket 70. The at least one sensor 74 generates a sensor signal when a hydrocarbon liquid is detected thereby.

The cartridge 2 may also include a valve mechanism 73. The valve mechanism 73 is in fluid communication with the runoff water egress port 48 formed in the cartridge housing 4 and selectively causes the runoff water egress port 48 to be in one of an open state to allow debris-filtered runoff water to flow therethrough and a closed state to prevent debris-filtered runoff water from flowing therethrough in response to a control signal received thereby.

The cartridge 2 of the present invention further preferably includes an electronic circuit 44. The electronic circuit 44 is in electrical communication with the at least one sensor 74 of the hydrocarbon fluid accumulator 58. The electronic circuit 44 is responsive to the sensor signal generated by the at least one sensor 74 and generates the control signal in response thereto to cause the valve mechanism 73 to effect the open state and the closed state of the runoff water egress port 48.

In yet another preferred form of the present invention, a cartridge 2 for use in a storm water drainage system further includes a hydrocarbon absorbent padding 36. The hydrocarbon absorbent padding 36 is disposed within the interior cavity 6 of the cartridge housing 4 and situated therein in proximity to the lower axial wall 10 thereof. The hydrocarbon absorbent padding 36 is in fluid communication with the flow through channels 34 to receive the debris-filtered runoff water flowing through the channels 34.

Preferably, the cartridge 2 of the present invention is mounted in a catch basin of a storm water drainage system. The storm water drainage system, and preferably the catch basin thereof, includes a support bracket. The housing 4 of the cartridge 2 further includes a mounting flange 14 and at least one fastener 21, the mounting flange 14 extending outwardly from the side wall 8 of the cartridge housing 4. The mounting flange 14 has at least one hole 20 folioed through the thickness thereof for receiving the at least one fastener 21 for securing the cartridge 2 to the support bracket of the storm water drainage system. The mounting flange 14, by adjustment of the at least one fastener 21, provides leveling of the cartridge within the storm water drainage system and, particularly, the catch basin thereof.

In a preferred form, the valve mechanism 73 of the cartridge 2 includes a flapper valve 54. The flapper valve 54 is pivotable relative to the runoff water egress port 48. The flapper valve 54 pivots between a first position in which the flapper valve 54 causes the runoff water egress port 48 to be in the open state, and a second position in which the flapper valve 54 causes the runoff water egress port 48 to be in the closed state. The valve mechanism 73 also preferably includes an elongated valve activation member 82, such as a chain. The elongated valve activation member 82 is coupled to the flapper valve 54. There is a first magnet 84 affixed to the elongated valve activation member 82.

The valve mechanism 73 also preferably includes a solenoid 76. The solenoid 76 has a reciprocating plunger 78. The plunger 78 has a free end, and a second magnet 80 mounted on the free end of the plunger 78. The magnet 84 on the elongated valve activation member 82 is selectively magnetically coupled to the magnet 80 on the free end of the plunger 78 of the solenoid 76. The solenoid 76 receives the control signal from the electronic circuit 44 and causes the plunger 78 to move reciprocatingly in response thereto to cause the magnet 84 on the elongated valve activation member 82 to be one of magnetically coupled to the magnet 80 on the free end of the plunger 78 or magnetically decoupled from the magnet 80 on the free end of the plunger 78. When the magnet 84 on the elongated valve activation member 82 is magnetically coupled to the magnet 80 on the free end of the plunger 78 of the solenoid 76, the flapper valve 54 is maintained in the first position to effect the open state of the runoff water egress port 48. However, when the magnet 84 on the elongated valve activation member 82 is magnetically decoupled from the magnet 80 on the free end of the plunger 78 of the solenoid 76, the flapper valve 54 is in the second position to effect the closed state of the runoff water egress port 48.

The cartridge 2 of the present invention may further include at least one float sensor 86. The at least one float sensor 86 is situated within the interior cavity 6 of the cartridge housing 4. The at least one float sensor 86 detects the presence of runoff water within the interior cavity 6 of the cartridge housing 4, the at least one float sensor 86 generating a float sensor signal when runoff water in the interior cavity 6 of the cartridge housing 4 is detected thereby. The at least one float sensor 86 provides the float sensor signal to the electronic circuit 44. The electronic circuit 44 generates the control signal to cause the valve mechanism 73 to effect the closed state of the runoff water egress port 48 when the at least one sensor 74 of the hydrocarbon fluid accumulator 58 detects the presence of hydrocarbon liquid and, simultaneously, when the at least one float sensor 86 detects the presence of runoff water in the interior cavity 6 of the cartridge housing 4.

In yet another preferred form of the present invention, multiple cartridges 2 may communicate wirelessly with one another. To effect such communication, the electronic circuit 44 of the cartridge 2 includes a transmitter 75 and a receiver 77. The transmitter 75 is provided for sending a transmitted signal to another cartridge 2, the transmitted signal, when transmitted, causing the electronic circuit 44 of the other cartridge 2 to generate a control signal in response thereto to effect a closed state of a runoff water egress port 48 of the other cartridge 2. The receiver 77 is provided for receiving a received signal from the other cartridge 2, the received signal, when received, causing the electronic circuit 44 to generate the control signal in response thereto to effect the closed state of the water runoff egress port 48.

Although illustrative embodiments of the present invention have been described herein with reference to the accompanying drawing, it is to be understood that the invention is not limited to those precise embodiments, and that various other changes and modifications may be effected therein by one skilled in the art without departing from the scope or spirit of the invention.

What is claimed is:

1. Apparatus for detecting the presence of hydrocarbon fluid in runoff water, which comprises:
    an outer canister, the outer canister having a housing, the housing having a top axial end and a bottom axial end situated opposite the top axial end and a side wall extending between the top axial end and the bottom axial end, the canister housing defining an interior cavity and including a water ingress opening situated in proximity to the top axial end and a water egress opening situated in proximity to the bottom axial end, the outer canister further having a valve situated in proximity to the bottom axial end, the valve being in communication with the water egress opening and selectively closing the water egress opening in response to a control signal received thereby; and
    a cartridge, the cartridge being situated in the interior cavity of the housing of the outer canister, the cartridge including:
    a pre-filter, the pre-filter being in fluid communication with the water ingress opening of the canister housing and receiving therein water flowing through the water ingress opening, the pre-filter being at least partially water permeable and outputting therefrom pre-filtered water in response to water received thereby flowing through the water ingress opening;
    a water diverter plate, the water diverter plate having an opening formed through the thickness thereof, the water diverter plate being situated in fluid communication with the pre-filter and thereby receiving any pre-filtered water outputted from the pre-filter, the water diverter plate diverting the flow of pre-filtered water from the pre-filter so that the pre-filtered water passes through the opening in the water diverter plate;
    an inner containment vessel and an outer containment vessel, the inner containment vessel and the outer containment vessel including vessel defining walls, the vessel defining walls further defining each of the inner containment vessel and the outer containment vessel with an interior cavity, the inner containment vessel being disposed within the interior cavity of the outer containment vessel, the vessel defining wall of the outer containment vessel being spaced inwardly from the side wall of the housing of the outer canister and defining a space therebetween for receiving the flow of pre-filtered water therethrough, the vessel defining wall of the inner containment vessel being spaced inwardly of the vessel defining wall of the outer containment vessel and defining a space therebetween for receiving the flow of pre-filtered water therethrough, each of the inner containment vessel and the outer containment vessel including an upper axial end and a lower axial end situated opposite the upper axial end, the upper axial end of the inner containment vessel being disposed axially in proximity to the upper axial end of the outer containment vessel, and the lower axial end of the inner containment vessel being disposed axially in proximity to the lower axial end of the outer containment vessel, the vessel defining wall of the inner containment vessel having at least one water flow port formed through the thickness thereof and situated in proximity to the lower axial end thereof to allow the flow of pre-filtered water to pass therethrough and into the space defined by the vessel defining walls of the inner containment vessel and the outer containment vessel, the vessel defining wall of the outer containment vessel having at least one water flow port formed through the thickness thereof and situated in proximity to the upper axial end thereof to allow the flow of pre-filtered water in the space between the vessel defining walls of the inner containment vessel and the outer containment vessel to pass therethrough and into the space defined by the vessel defining wall of the outer containment vessel and the side wall of the housing of the outer canister, the upper axial end of the inner containment vessel having an opening formed therein to allow the flow of pre-filtered water received through the opening of the water diverter plate to pass therethrough and into the interior cavity of the inner containment vessel, the interior cavity of the inner containment vessel defining a chamber in which hydrocarbon liquid carried by the flow of pre-filtered water is at least partially separated from the pre-filtered water;

a diffuser/separator member situated within the interior cavity of the inner containment vessel, the diffuser/separator member being at least partially permeable to the flow of pre-filtered water therethrough, the diffuser/separator member having a first axial side which is in fluid communication with the opening formed in the upper axial end of the inner containment vessel, and a second axial side situated opposite the first axial side and which is in fluid communication with the at least one water flow port of the inner containment vessel, the diffuser/separator member acting to slow the flow of pre-filtered water through the interior cavity of the inner containment vessel and thereby helping to effect the separation of hydrocarbon liquid from the pre-filtered water, the hydrocarbon liquid rising to the surface of the pre-filtered water situated above the first axial side of the diffuser/separator member;

a hydrocarbon fluid accumulator, the hydrocarbon fluid accumulator being positioned in fluid communication with the pre-filtered water, and any hydrocarbon liquid separated therefrom, and situated above the first axial side of the diffuser/separator member, the hydrocarbon fluid accumulator having a housing defining at least one pocket for accumulating hydrocarbon liquid therein which has separated from the pre-filtered water, the hydrocarbon fluid accumulator further including at least one sensor, the at least one sensor residing in the at least one pocket and detecting the presence of hydrocarbon liquid accumulating within the at least one pocket, the at least one sensor generating a sensor signal when a hydrocarbon liquid is detected thereby;

a post filter member, the post filter member being situated in fluid communication with the space between and defined by the vessel defining wall of the outer containment vessel and the side wall of the housing of the outer canister, the post filter member being at least partially water permeable and outputting therefrom post-filtered water in response to pre-filtered water received thereby flowing through the space between the vessel defining wall of the outer containment vessel and the side wall of the housing of the outer canister, the post-filtered water selectively flowing through the water egress opening of the housing of the outer canister; and an electronic circuit, the electronic circuit being in electrical communication with the at least one sensor of the hydrocarbon accumulator, the electronic circuit being responsive to the sensor signal generated by the at least one sensor and generating the control signal in response thereto to cause the valve to selectively close the water egress opening.

2. Apparatus for detecting the presence of hydrocarbon fluid in runoff water, which comprises:

an outer canister, the outer canister having a housing, the housing having a top axial end and a bottom axial end situated opposite the top axial end and a side wall extending between the top axial end and the bottom axial end, the canister housing defining an interior cavity and including a water ingress opening situated in proximity to the top axial end and a water egress opening situated in proximity to the bottom axial end, the outer canister further having a valve situated in proximity to the bottom axial end, the valve being in communication with the water egress opening and selectively closing the water egress opening in response to a control signal received thereby; and a cartridge, the cartridge being situated in the interior cavity of the housing of the outer canister, the cartridge including:

a pre-filter, the pre-filter being in communication with the water ingress opening of the canister housing and receiving therein water flowing through the water ingress opening, the pre-filter being at least partially water permeable and outputting therefrom pre-filtered water in response to water received thereby flowing through the water ingress opening;

at least one containment vessel, the at least one containment vessel including a vessel defining wall, the vessel defining wall further defining the at least one containment vessel with an interior cavity, the interior cavity of the at least one containment vessel defining a chamber in which hydrocarbon liquid carried by the flow of pre-filtered water is at least partially separated from the pre-filtered water, the at least one containment vessel including a first axial end and a second axial end situated opposite the first axial end, the vessel defining wall of the at least one containment vessel having a water input opening situated in proximity to the first axial end thereof to allow the flow of pre-filtered water outputted by the pre-filter to pass therethrough and into the interior cavity of the at least one containment vessel, the vessel defining wall of the at least one containment vessel having a water output opening formed through the thickness thereof and situated in proximity to the second axial end thereof to allow the flow of pre-filtered water to pass therethrough and out of the interior cavity of the at least one containment vessel;

a diffuser/separator member situated within the interior cavity of the at least one containment vessel, the diffuser/separator member being at least partially permeable to the flow of pre-filtered water therethrough, the diffuser/separator member having a first axial side which is in fluid communication with the water input opening of the at least one containment vessel and a second axial side situated opposite the first axial side and which is in fluid communication with the water output opening of the at least one containment vessel, the diffuser/separator member acting to slow the flow of pre-filtered water through the interior cavity of the at least one containment vessel and thereby helping to effect the separation of hydrocarbon liquid from the pre-filtered water, the hydrocarbon liquid rising to the surface of the pre-filtered water situated above the first axial side of the diffuser/separator member;

a hydrocarbon fluid accumulator, the hydrocarbon fluid accumulator being positioned in fluid communication with the pre-filtered water, and any hydrocarbon liquid separated therefrom, and situated above the first axial side of the diffuser/separator member, the hydrocarbon fluid accumulator having a housing defining at least one pocket for accumulating hydrocarbon liquid therein which has separated from the pre-filtered water, the hydrocarbon fluid accumulator further including at least one sensor, the at least one sensor residing in the at least one pocket and detecting the presence of hydrocarbon liquid accumulating within the at least one pocket, the at least one sensor generating a sensor signal when a hydrocarbon liquid is detected thereby; and an electronic circuit, the electronic circuit being in electrical communication with the at least one sensor of the hydrocarbon fluid accumulator, the electronic circuit being responsive to the sensor signal generated by the at least one sensor and generating the control signal in response thereto to cause the valve to selectively close the water egress opening.

3. Apparatus for detecting the presence of hydrocarbon fluid in runoff water as defined by claim 2, wherein the cartridge further includes:
a water diverter plate, the water diverter plate having an opening formed through the thickness thereof, the water diverter plate being situated in fluid communication with the pre-filter and thereby receiving any pre-filtered water outputted by the pre-filter, the water diverter plate diverting the flow of pre-filtered water from the pre-filter so that the pre-filtered water passes through the opening in the water diverter plate, the water input opening of the at least one containment vessel being in fluid communication with the opening in the water diverter plate.

4. Apparatus for detecting the presence of hydrocarbon fluid in runoff water as defined by claim 3, wherein the cartridge further includes:
an upper plate, the upper plate being disposed axially with respect to the water diverter plate and being spaced apart therefrom a predetermined distance, the upper plate and the water diverter plate together defining a space therebetween which is in fluid communication with the water input opening of the at least one containment vessel for directing the flow of pre-filtered water toward the water input opening of the at least one containment vessel.

5. Apparatus for detecting the presence of hydrocarbon fluid in runoff water as defined by claim 2, wherein the at least one containment vessel of the cartridge further includes:
an inner containment vessel and an outer containment vessel, the inner containment vessel and the outer containment vessel including a first vessel defining wall and a second vessel defining wall, respectively, the first and second vessel defining walls further respectively defining the inner containment vessel and the outer containment vessel with a first interior cavity and a second interior cavity, the inner containment vessel being disposed within the second interior cavity of the outer containment vessel, the second vessel defining wall of the outer containment vessel being spaced inwardly from the side wall of the housing of the outer canister and defining a space therebetween for receiving the flow of pre-filtered water therethrough, the first vessel defining wall of the inner containment vessel being spaced inwardly of the second vessel defining wall of the outer containment vessel and defining a space therebetween for receiving the flow of pre-filtered water therethrough, each of the inner containment vessel and the outer containment vessel including an upper axial end and a lower axial end situated opposite the upper axial end, the upper axial end of the inner containment vessel being disposed axially in proximity to the upper axial end of the outer containment vessel, and the lower axial end of the inner containment vessel being disposed axially in proximity to the lower axial end of the outer containment vessel, the water input opening being formed in the upper axial end of the inner containment vessel to allow the flow of pre-filtered water to pass therethrough and into the first interior cavity of the inner containment vessel, the first interior cavity of the inner containment vessel defining the chamber in which hydrocarbon liquid carried by the flow of pre-filtered water is at least partially separated from the pre-filtered water, the water output opening including at least one first water flow port and at least one second water flow port, the at least one first water flow port being formed through the thickness of the first vessel defining wall of the inner containment vessel and situated in proximity to the lower axial end thereof to allow the flow of pre-filtered water to pass therethrough and into the space defined by the first and second vessel defining walls of the inner containment vessel and the outer containment vessel, the at least one second water flow port being formed through the thickness of the second vessel defining wall of the outer containment vessel and situated in proximity to the upper axial end thereof to allow the flow of pre-filtered water in the space between the first and second vessel defining walls of the inner containment vessel and the outer containment vessel to pass therethrough and into the space defined by the second vessel defining wall of the outer containment vessel and the side wall of the housing of the outer canister.

6. Apparatus for detecting the presence of hydrocarbon fluid in runoff water as defined by claim 5, wherein the cartridge further includes:
a post filter member, the post filter member being situated in fluid communication with the space between and defined by the second vessel defining wall of the outer containment vessel and the side wall of the housing of the outer canister, the post filter member being at least partially water permeable and outputting therefrom post-filtered water in response to pre-filtered water received thereby flowing through the space between the second vessel defining wall of the outer containment vessel and the side wall of the housing of the outer canister, the post-filtered water selectively flowing through the water egress opening of the housing of the outer canister.

7. Apparatus for detecting the presence of hydrocarbon fluid in runoff water as defined by claim 6, wherein the cartridge further includes:
a first bottom plate and a second bottom plate, the first bottom plate having a perforated portion, the perforated portion having perforations formed through the thickness thereof, the post filter member being situated in alignment with the perforated portion of the first bottom plate such that post-filtered water outputted from the post filter member passes through the perforations of the perforated portion of the first bottom plate; and
wherein the second bottom plate is disposed axially with respect to the first bottom plate and spaced apart therefrom to define a channel therebetween for receiving post-filtered water flowing through the perforations of the perforated portion of the first bottom plate, the second bottom plate including an opening formed through the thickness thereof, the opening being in fluid communication with the water egress opening of the housing of the outer canister, the channel defined by the first bottom plate and the second bottom plate being in fluid communication with the opening formed in the second bottom plate and directing the flow of post-filtered water to the opening formed in the second bottom plate.

8. Apparatus for detecting the presence of hydrocarbon fluid in runoff water as defined by claim 2, wherein the cartridge is removable from the interior cavity of the outer canister.

9. Apparatus for detecting the presence of hydrocarbon fluid in runoff water as defined by claim 8, wherein the cartridge further includes:
at least one post having opposite axial ends, and at least one lifting member situated on one of the opposite axial ends of the at least one post, the at least one post being operatively coupled to at least one of the pre-filter and the at least one containment vessel to facilitate removal of the cartridge from the interior cavity of the housing of the outer canister.

10. Apparatus for detecting the presence of hydrocarbon fluid in runoff water as defined by claim 2, wherein the cartridge further includes:
a rod, the rod being situated within the interior cavity of the at least one containment vessel, the diffuser/separator member being mounted on the rod and being positionable thereon at various axial locations along at least a portion of the axial length of the rod.

11. Apparatus for detecting the presence of hydrocarbon fluid in runoff water as defined by claim 10, wherein the cartridge further includes:
first and second holding plates, the first holding plate being mounted on the rod and situated on the first axial side of the diffuser/separator member, and the second holding plate being mounted on the rod and situated on the second axial side of the diffuser/separator member.

12. Apparatus for detecting the presence of hydrocarbon fluid in runoff water as defined by claim 2, wherein the housing of the hydrocarbon fluid accumulator of the cartridge is hub-shaped with concentrically arranged inner and outer radial walls, each of the inner and outer walls having a bottom edge, and a variably sloping transverse top wall which varies in depth relative to the bottom edge of the inner and outer walls to thereby define the at least one pocket with diametrically opposed first and second pockets in which hydrocarbon liquid may accumulate; and
wherein the at least one sensor includes a first sensor and a second sensor, the first sensor residing in the first pocket and the second sensor residing in the second pocket, each of the first sensor and the second sensor detecting the presence of hydrocarbon liquid accumulating within the first pocket and the second pocket, respectively, each of the first sensor and the second sensor generating a sensor signal when a hydrocarbon liquid is detected thereby, the sensor signals of the first sensor and of the second sensor being provided to the electronic circuit.

13. Apparatus for detecting the presence of hydrocarbon fluid in runoff water as defined by claim 2, wherein the housing of the hydrocarbon fluid accumulator defines the at least one pocket with a first pocket and a second pocket, the first pocket being disposed diametrically opposite the second pocket, each of the first pocket and the second pocket being provided for accumulating hydrocarbon liquid therein which has separated from the pre-filtered water; and
wherein the at least one sensor includes a first sensor and a second sensor, the first sensor residing in the first pocket and the second sensor residing in the second pocket, the first sensor and the second sensor detecting the presence of hydrocarbon liquid accumulating within the first pocket and the second pocket, respectively, the first sensor and the second sensor generating sensor signals when a hydrocarbon liquid is detected thereby, the sensor signals being provided to the electronic circuit.

14. Apparatus for detecting the presence of hydrocarbon fluid in runoff water as defined by claim 2, wherein the valve is an electronically actuated gate valve, the electronically actuated gate valve including a sliding plate which is in fluid communication with the water egress opening of the housing of the outer canister, the sliding plate being positionable in a first position in which the sliding plate closes the water egress opening to the flow of water therethrough, and a second position in which the sliding plate opens the water egress opening to the flow of water therethrough.

15. Apparatus for detecting the presence of hydrocarbon fluid in runoff water as defined by claim 2, wherein the valve is electronically actuatable and mechanically actuatable to selectively close the water egress opening, the valve including a cable mounted thereto and extending therefrom, the cable including a first end operatively coupled to the valve, and a second end situated opposite the first end, and a grab handle situated on the second end of the cable, the grab handle being graspable by a person to effect a mechanical closure of the water egress opening by the valve.

16. A cartridge for use in a storm water drainage system, the cartridge detecting the presence of hydrocarbon fluid in runoff water flowing into the storm water drainage system and actuating a valve when hydrocarbon fluid in the runoff water is detected, the cartridge being receivable in an outer canister, the outer canister having a housing, the housing having a top axial end and a bottom axial end situated opposite the top axial end and a side wall extending between the top axial end and the bottom axial end, the canister housing defining an interior cavity in which the cartridge is received, and including a water ingress opening situated in proximity to the top axial end and a water egress opening situated in proximity to the bottom axial end, the canister further having a valve situated in proximity to the bottom axial end, the valve being in communication with the water egress opening and selectively closing the water egress opening in response to a control signal received thereby and generated by the cartridge, the cartridge comprising:
a pre-filter, the pre-filter being in communication with the water ingress opening of the canister housing and receiving therein water flowing through the water ingress opening, the pre-filter being at least partially water permeable and outputting therefrom pre-filtered water in response to water received thereby flowing through the water ingress opening;
at least one containment vessel, the at least one containment vessel including a vessel defining wall, the vessel defining wall further defining the at least one containment vessel with an interior cavity, the interior cavity of the at least one containment vessel defining a chamber in which hydrocarbon liquid carried by the flow of pre-filtered water is at least partially separated from the pre-filtered water, the at least one containment vessel including a first axial end and a second axial end situated opposite the first axial end, the vessel defining wall of the at least one containment vessel having a water input opening situated in proximity to the first axial end thereof to allow the flow of pre-filtered water outputted by the pre-filter to pass therethrough and into the interior cavity of the at least one containment vessel, the vessel defining wall of the at least one containment vessel having a water output opening formed through the thickness thereof and situated in proximity to the second axial end thereof to allow the flow of pre-filtered water to pass therethrough and out of the interior cavity of the at least one containment vessel;

a diffuser/separator member situated within the interior cavity of the at least one containment vessel, the diffuser/separator member being at least partially permeable to the flow of pre-filtered water therethrough, the diffuser/separator member having a first axial side which is in fluid communication with the water input opening of the at least one containment vessel and a second axial side situated opposite the first axial side and which is in fluid communication with the water output opening of the at least one containment vessel, the diffuser/separator member acting to slow the flow of pre-filtered water through the interior cavity of the at least one containment vessel and thereby helping to effect the separation of hydrocarbon liquid from the pre-filtered water, the hydrocarbon liquid rising to the surface of the pre-filtered water situated above the first axial side of the diffuser/separator member;

a hydrocarbon fluid accumulator, the hydrocarbon fluid accumulator being positioned in fluid communication with the pre-filtered water, and any hydrocarbon liquid separated therefrom, and situated above the first axial side of the diffuser/separator member, the hydrocarbon fluid accumulator having a housing defining at least one pocket for accumulating hydrocarbon liquid therein which has separated from the pre-filtered water, the hydrocarbon fluid accumulator further including at least one sensor, the at least one sensor residing in the at least one pocket and detecting the presence of hydrocarbon liquid accumulating within the at least one pocket, the at least one sensor generating a sensor signal when a hydrocarbon liquid is detected thereby; and an electronic circuit, the electronic circuit being in electrical communication with the at least one sensor of the hydrocarbon fluid accumulator, the electronic circuit being responsive to the sensor signal generated by the at least one sensor and generating the control signal in response thereto to cause the valve to selectively close the water egress opening.

17. A cartridge for use in a storm water drainage system, the cartridge detecting the presence of hydrocarbon fluid in runoff water flowing into the storm water drainage system and blocking the flow of runoff water thereinto when hydrocarbon fluid in the runoff water is detected, the cartridge comprising:

a housing, the housing having a side wall, an upper axial wall and a lower axial wall situated opposite the upper axial wall, the housing defining an interior cavity, at least one of the side wall and the upper axial wall of the housing having a runoff water ingress port formed through the thickness thereof for receiving runoff water flowing into the water drainage system, the interior cavity of the cartridge housing being in fluid communication with the water runoff ingress port and receiving therein runoff water passing through the runoff water ingress port, at least one of the side wall and the lower axial wall of the housing having a runoff water egress port formed through the thickness thereof, the runoff water egress port being in fluid communication with the interior cavity of the cartridge housing and selectively receiving and passing therethrough runoff water received by the interior cavity of the cartridge housing;

a debris filter medium, the debris filter medium being situated in fluid communication with the runoff water ingress port, the debris filter medium being at least partially permeable to runoff water and providing runoff water that is debris filtered to the interior cavity of the cartridge housing;

a first inner wall, the first inner wall being situated within the interior cavity of the cartridge housing, the first inner wall having a plurality of slots formed through the thickness thereof, the slots of the plurality of slots being disposed in alignment with the debris filter medium and receiving therethrough debris-filtered runoff water outputted by the debris filter medium;

a second inner wall, the second inner wall being situated within the interior cavity of the cartridge housing and being spaced over at least a portion thereof from the first inner wall;

a plurality of separator walls, the separator walls of the plurality of separator walls extending transversely between and being joined to the first inner wall and the second inner wall, the separator walls, first inner wall and second inner wall together defining a plurality of flow through channels extending axially within the interior cavity of the cartridge housing in a direction towards the lower axial wall of the cartridge housing, the flow through channels being in fluid communication with the slots formed through the thickness of the first inner wall for receiving the debris-filtered runoff water passing through the slots, the flow through channels directing the flow of debris-filtered runoff water towards the lower axial wall of the cartridge housing;

a weir, the weir being disposed within the interior cavity of the cartridge housing and situated therein in proximity to the lower axial wall thereof, the weir being in fluid communication with the flow through channels to receive the debris-filtered runoff water flowing through the channels, the weir acting on the flow of debris-filtered runoff water received thereby to slow movement of the flow of debris-filtered runoff water thereby helping to effect a separation of hydrocarbon liquid from the debris-filtered runoff water received by the weir, the hydrocarbon liquid rising to the surface of the debris-filtered runoff water slowed by the weir;

a hydrocarbon fluid accumulator, the hydrocarbon fluid accumulator being situated within the interior cavity of the, cartridge housing and in proximity to the weir, the hydrocarbon fluid accumulator being in fluid communication with the debris-filtered runoff water slowed in movement by the weir, the hydrocarbon fluid accumulator having a housing defining at least one pocket for accumulating hydrocarbon liquid therein which has separated from the debris-filtered runoff water, the hydrocarbon fluid accumulator further including at least one sensor, the at least one sensor residing in the at least one pocket and detecting the presence of hydrocarbon liquid accumulating within the at least one pocket, the at least one sensor generating a sensor signal when a hydrocarbon liquid is detected thereby;

a valve mechanism, the valve mechanism being in fluid communication with the runoff water egress port formed in the cartridge housing and selectively causing the runoff water egress port to be in one of an open state to allow debris-filtered runoff water to flow therethrough and a closed state to prevent debris-filtered runoff water from flowing therethrough in response to a control signal received thereby; and an electronic circuit, the electronic circuit being in electrical communication with the at least one sensor of the hydrocarbon fluid accumulator, the electronic circuit being responsive to the sensor signal generated by the at least one sensor and generating the control signal in response thereto to cause the valve mechanism to effect the open state and the closed state of the runoff water egress port.

18. A cartridge for use in a storm water drainage system as defined by claim 17, which further comprises:

a hydrocarbon absorbent padding, the hydrocarbon absorbent padding being disposed within the interior cavity of the cartridge housing and situated therein in proximity to the lower axial wall thereof, the hydrocarbon absorbent padding being in fluid communication with the flow through channels to receive the debris-filtered runoff water flowing through the channels.

19. A cartridge for use in a storm water drainage system as defined by claim 17, wherein the storm water drainage system includes a support bracket, and wherein the housing of the cartridge further includes a mounting flange and at least one fastener, the mounting flange extending outwardly from the side wall of the cartridge housing, the mounting flange having at least one hole formed through the thickness thereof for receiving the at least one fastener for securing the cartridge to the support bracket of the storm water drainage system, the mounting flange, by adjustment of the at least one fastener, providing leveling of the cartridge within the storm water drainage system.

20. A cartridge for use in a storm water drainage system as defined by claim 17, wherein the valve mechanism includes:

a flapper valve, the flapper valve being pivotable relative to the runoff water egress port, the flapper valve pivoting between a first position in which the flapper valve causes the runoff water egress port to be in the open state, and a second position in which the flapper valve causes the runoff water egress port to be in the closed state;

an elongated valve activation member, the elongated valve activation member being coupled to the flapper valve;

a magnet, the magnet being affixed to the elongated valve activation member; and a solenoid, the solenoid having a reciprocating plunger, the plunger having a free end, and a magnet mounted on the free end of the plunger, the magnet on the elongated valve activation member being selectively magnetically coupled to the magnet on the free end of the plunger of the solenoid, the solenoid receiving the control signal from the electronic circuit and causing the plunger to move reciprocatingly in response thereto to cause the magnet on the elongated valve activation member to be one of magnetically coupled to the magnet on the free end of the plunger or magnetically decoupled from the magnet on the free end of the plunger, wherein when the magnet on the elongated valve activation member is magnetically coupled to the magnet on the free end of the plunger of the solenoid, the flapper valve is maintained in the first position to effect the open state of the runoff water egress port, and wherein when the magnet on the elongated valve activation member is magnetically decoupled from the magnet on the free end of the plunger of the solenoid, the flapper valve is in the second position to effect the closed state of the runoff water egress port.

21. A cartridge for use in a storm water drainage system as defined by claim 17, which further comprises:

at least one float sensor, the at least one float sensor being situated within the interior cavity of the cartridge housing, the at least one float sensor detecting the presence of runoff water within the interior cavity of the cartridge housing, the at least one float sensor generating a float sensor signal when runoff water in the interior cavity of the cartridge housing is detected thereby, the at least one float sensor providing the float sensor signal to the electronic circuit, wherein the electronic circuit generates the control signal to cause the valve mechanism to effect the closed state of the runoff water egress port when the at least one sensor of the hydrocarbon fluid accumulator detects the presence of hydrocarbon liquid and when the at least one float sensor detects the presence of runoff water in the interior cavity of the cartridge housing.

22. A cartridge for use in a storm water drainage system as defined by claim 17, wherein the electronic circuit includes a transmitter and a receiver, the transmitter being provided for sending a transmitted signal to another cartridge, the transmitted signal, when transmitted, causing the electronic circuit of the other cartridge to generate a control signal in response thereto to effect a closed state of a runoff water egress port of the other cartridge, the receiver being provided for receiving a received signal from the other cartridge, the received signal, when received, causing the electronic circuit to generate the control signal in response thereto to effect the closed state of the water runoff egress port.

* * * * *